(12) United States Patent
Fichorova et al.

(10) Patent No.: US 12,370,228 B2
(45) Date of Patent: *Jul. 29, 2025

(54) **MEDICINAL VAGINAL *LACTOBACILLUS* COCKTAIL**

(71) Applicant: THE BRIGHAM AND WOMEN'S HOSPITAL, INC., Boston, MA (US)

(72) Inventors: Raina Fichorova, Chestnut Hill, MA (US); Andrew Onderdonk, Westwood, MA (US); Hidemi Yamamoto, Medford, MA (US); Mary Delaney, Belmont, MA (US); Andrea Dubois, Roslindale, MA (US)

(73) Assignee: THE BRIGHAM AND WOMEN'S HOSPITAL, INC.

( * ) Notice: Subject to any disclaimer, the term of this patent is extended or adjusted under 35 U.S.C. 154(b) by 626 days.

This patent is subject to a terminal disclaimer.

(21) Appl. No.: 17/545,777

(22) Filed: Dec. 8, 2021

(65) Prior Publication Data
US 2022/0184151 A1 Jun. 16, 2022

Related U.S. Application Data

(63) Continuation of application No. 16/307,857, filed as application No. PCT/US2017/041558 on Jul. 11, 2017, now Pat. No. 11,260,086.

(60) Provisional application No. 62/360,535, filed on Jul. 11, 2016.

(51) Int. Cl.
| | |
|---|---|
| *A61K 35/747* | (2015.01) |
| *A61K 9/00* | (2006.01) |
| *A61K 9/06* | (2006.01) |
| *A61K 31/4164* | (2006.01) |
| *A61K 31/7016* | (2006.01) |
| *A61K 31/7056* | (2006.01) |
| *A61K 31/7076* | (2006.01) |
| *A61K 35/00* | (2006.01) |
| *A61K 45/06* | (2006.01) |
| *C12N 1/20* | (2006.01) |
| *C12R 1/225* | (2006.01) |

(52) U.S. Cl.
CPC .......... *A61K 35/747* (2013.01); *A61K 9/0034* (2013.01); *A61K 31/4164* (2013.01); *A61K 31/7016* (2013.01); *A61K 31/7056* (2013.01); *A61K 31/7076* (2013.01); *A61K 45/06* (2013.01); *C12N 1/20* (2013.01); *C12N 1/205* (2021.05); *A61K 9/06* (2013.01); *A61K 2035/115* (2013.01); *C12R 2001/225* (2021.05)

(58) Field of Classification Search
CPC .............. A61K 35/747; A61K 9/0034; A61K 31/4164; A61K 31/7016; A61K 31/7056; A61K 31/7076; A61K 45/06; A61K 9/06; A61K 2035/115; C12N 1/20; C12N 1/205
See application file for complete search history.

(56) References Cited

U.S. PATENT DOCUMENTS

| | | |
|---|---|---|
| 2008/0274162 A1 | 11/2008 | Nessa et al. |
| 2013/0171253 A1 | 7/2013 | Kiss et al. |

FOREIGN PATENT DOCUMENTS

| | | | |
|---|---|---|---|
| WO | 2006065873 A2 | 6/2006 | |
| WO | WO-2012147056 A1 * | 11/2012 | ............ A61K 31/20 |
| WO | 2015067141 A1 | 5/2015 | |
| WO | 2015173693 A1 | 11/2015 | |
| WO | 2016100086 A1 | 6/2016 | |
| WO | 2017035412 A1 | 3/2017 | |

OTHER PUBLICATIONS

Curlin et al. Frontiers in Bioscience, Scholar, 2013, vol. 5, p. 507-515. (Year: 2013).*
ATCC—*Salmonella enterica* subsp. *enterica* (ex Kauffmann and Edwards) Le Minor and Popoff serovar Typhimurium (ATCC(R) 6994(TM)). Website [online]. 2005 (Retrieved on Dec. 1, 2017]. Retrieved from the Internet: <URL: https://www.alcc.org/Products/All/6994.aspx>.
Fichorova et al., "Novel vaginal microflora colonization model providing new insight into microbicide mechanism of action." MBio 2(6):1-10 (2011).
Pavlova et al., "Genetic diversity of vaginal lactobacilli from women in different countries based on 16S rRNA gene sequences." Journal of Applied Microbiology 92(3):451-459 (2002).
Ravel et al. "Vaginal microbiome of reproductive-age women." Proceedings of the National Academy of Sciences 108 (Supplement 1): 4680-4687 (2011).
Sandrini et al., "Deoxyribonucleoside kinases activate nucleoside antibiotics in severely pathogenic bacteria." Antimicrobial Agents and Chemotherapy 51(8):2726-2732 (2007).
Saulnier et al., "Identification of prebiotic fructooligosaccharide metabolism in Lactobacillus plantarum WCFS1 through microarrays." Applied and Environmental Microbiology 73(6):1753-1765 (2007).
Semyonov et al. "Using ultrasonic vacuum spray dryer to produce highly viable dry probiotics." LWT-Food Science and Technology 44(9): 1844-1852 (2011).

* cited by examiner

*Primary Examiner* — Kade Ariani
(74) *Attorney, Agent, or Firm* — NIXON PEABODY LLP; David S. Resnick; Mark J. Fitzgerald

(57) ABSTRACT

Described herein are methods and compositions for the use of treating and/or preventing vaginal bacterial infection and promoting healthy vaginal flora. Aspects of the invention relate to administering to a subject in need thereof a composition comprising a bacterial mixture of *L. crispatus, L. gasseri,* and *L. jensenii.*

18 Claims, 48 Drawing Sheets

Specification includes a Sequence Listing.

FIG. 1

| Manifestation | Number of Proteins Found to be Persistently/Recurrently Elevated Concentrations | | |
|---|---|---|---|
| | 0-1 | 2-4 | 5+ |
| Ventriculomegaly | 1.0 | 1.2 (0.7-2.0) | 3.4 (2.0-5.9) |
| Any cerebral palsy | 1.0 | 1.0 (0.5-1.6) | 2.6 (1.5-4.5) |
| Diparesis | 1.0 | 0.7 (0.2-1.9) | 3.6 (1.6-8.2) |
| Hemiparesis | 1.0 | 0.8 (0.2-3.1) | 4.1 (1.4-12) |
| MDI <55 | 1.0 | 1.4 (0.9-2.2) | 2.6 (1.6-4.2) |
| Microcephaly | 1.0 | 1.7 (1.0-2.8) | 2.4 (1.3-4.3) |
| Attention problem | 1.0 | 2.2 (1.3-3.8) | 2.8 (1.4-5.2) |

FIG. 4

Placental colonization | Systemic newborn inflammation

Acute Phase Reactants | Leukocytosis/Diapedesis | Chemokines/Enzymes | Tissue Damage

| | | CRP | SAA | IL1B | IL6 | ICAM1 | ICAM3 | IL8 | MCP4 | MIP1B | RANTES/ITAC | MMP9 | MPO |
|---|---|---|---|---|---|---|---|---|---|---|---|---|---|
| Lactobacillus | Alone | | | | | | | | | | | | |
| | Alone and Mixed | | | | | | | | | | | | |
| | Mixed | | | | | | | | | | | | |
| BV | Alone | | | | | | | | | | | | |
| | Alone and Mixed | | | | | | | | | | | | |
| | Mixed | | | | | | | | | | | | |
| Mycoplasma | All | | | | | | | | | | | | |

FIG. 8A-8E
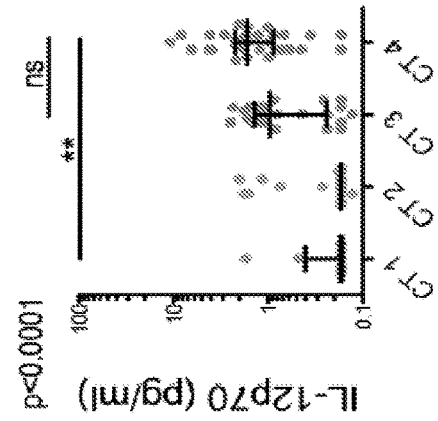
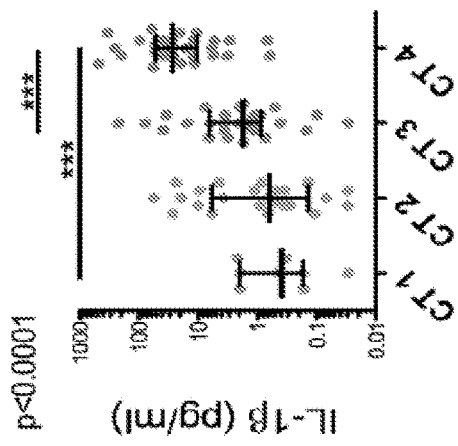
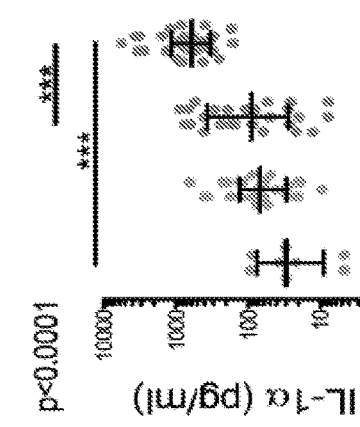
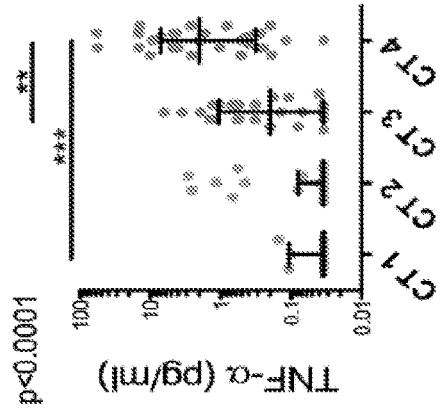
FIG. 8A
FIG. 8B
FIG. 8C
FIG. 8D
FIG. 8E

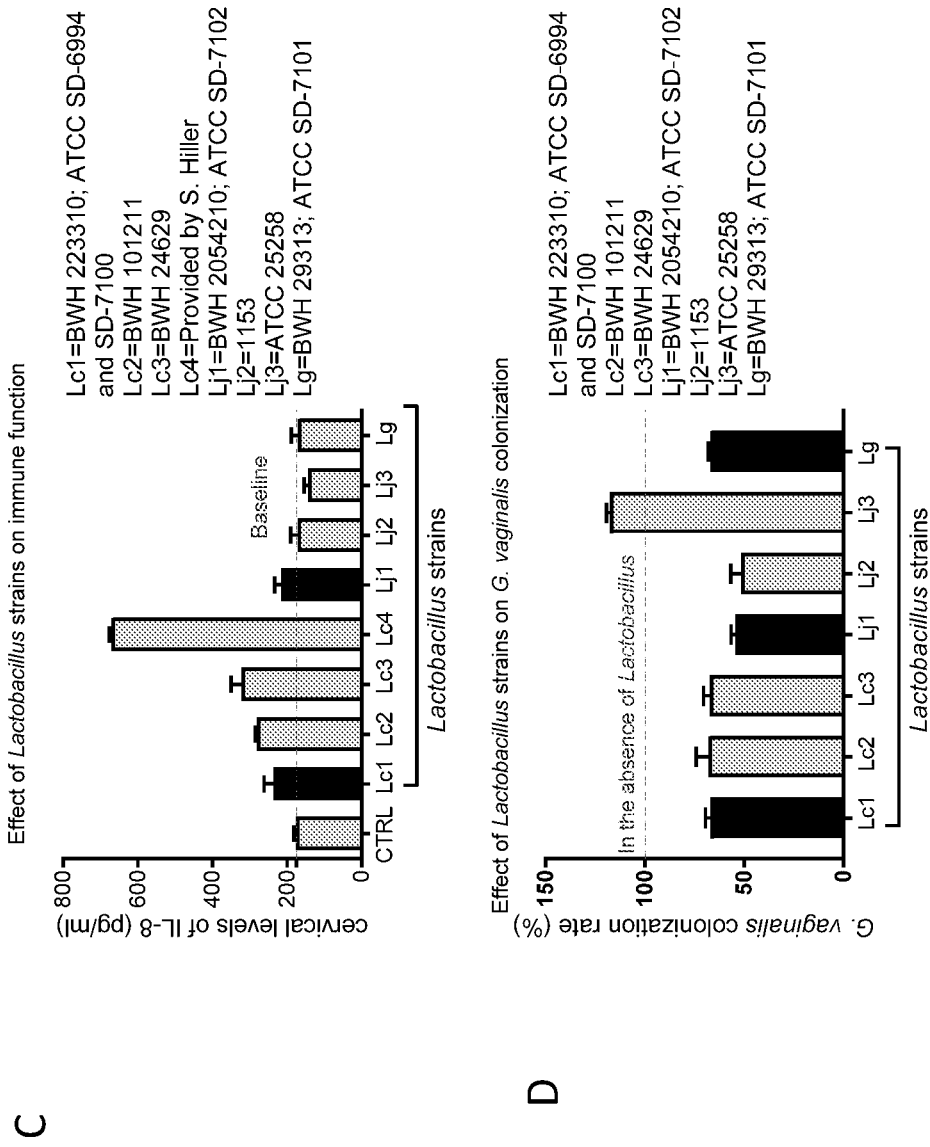
FIG. 13C-D

Reproducible epithelial colonization

Preservation of vaginal epithelial viability

Activities against BV pathogens – *G. vaginalis*

Activities against BV pathogens

Mitigated pathogenic inflammatory responses of BV pathogen

A. Stability of PBV bacteria stored over a period of 2 years at ambient T⁰

B. Preservation of epithelial tissue colonization capacity of PBV bacteria stored over 2 years at ambient T⁰

SEQUENCE LISTING

<160> NUMBER OF SEQ ID NOS: 51

<210> SEQ ID NO 1
<211> LENGTH: 478
<212> TYPE: DNA
<213> ORGANISM: Lactobacillus crispatus

<400> SEQUENCE: 1

```
tgcagtcgag cgagcggaac taacagattt acttcggtaa tgacgttagg aaagcgagcg      60
gcggatgggt gagtaacacg tggggaacct gccccatagt ctgggatacc acttggaaac     120
aggtgctaat accggataag aaagcagatc gcatgatcag cttttaaaag gcggcgtaag     180
ctgtcgctat gggatggccc cgcggtgcat tagctagttg gtaaggtaaa ggcttaccaa     240
ggcgatgatg catagccgag ttgagagact gatcggccac attgggactg agacacggcc     300
caaactccta cgggaggcag cagtagggaa tcttccacaa tggacgcaag tctgatggag     360
caacgccgcg tgagtgaaga aggttttcgg atcgtaaagc tctgttgttg gtgaagaagg     420
atagaggtag taactggcct ttatttgacg gtaatcaacc agaaagtcac ggctaact      478
```

<210> SEQ ID NO 2
<211> LENGTH: 475
<212> TYPE: DNA
<213> ORGANISM: Lactobacillus crispatus

<400> SEQUENCE: 2

```
cgtcaataaa ggccagttac tacctctatc cttcttcacc aacaacagag ctttacgatc      60
cgaaaacctt cttcactcac gcggcgttgc tccatcagac ttgcgtccat tgtggaagat     120
tccctactgc tgcctcccgt aggagtttgg gccgtgtctc agtcccaatg tggccgatca     180
gtctctcaac tcggctatgc atcatcgcct tggtaagcct ttaccttacc aactagctaa     240
tgcaccgcgg ggccatccca tagcgacagc ttacgccgcc ttttaaaagc tgatcatgcg     300
atctgctttc ttatccggta ttagcacctg tttccaagtg gtatcccaga ctatggggca     360
```

```
ggttccccac gtgttactca cccatccgcc gctcgctttc ctaacgtcat taccgaagta    420
aatctgttag ttccgctcgc tcgacttgca tgtattaggc acgccgccag cgttc         475

<210> SEQ ID NO 3
<211> LENGTH: 481
<212> TYPE: DNA
<213> ORGANISM: Lactobacillus jensenii

<400> SEQUENCE: 3
tgcagtcgag cgagcttgcc tattgaaatt cttcggaatg gacatagata caagctagcg     60
gcggatgggt gagtaacgcg tgggtaacct gcccttaagt ctgggatacc atttggaaac    120
agatgctaat accggataaa agctactttc gcatgaaaga agtttaaaag gcggcgtaag    180
ctgtcgctaa aggatggacc tgcgatgcat tagctagttg gtaaggtaac ggcttaccaa    240
ggcgatgatg catagccgag ttgagagact gatcggccac attgggactg agacacggcc    300
caaactccta cggaggcag cagtagggaa tcttccacaa tggacgcaag tctgatggag     360
caacgccgcg tgagtgaaga aggttttcgg atcgtaaagc tctgttgttg gtgaagaagg    420
atagaggtag taactggcct ttatttgacg gtaatcaacc agaaagtcac ggctaactac    480
g                                                                    481

<210> SEQ ID NO 4
<211> LENGTH: 475
<212> TYPE: DNA
<213> ORGANISM: Lactobacillus jensenii

<400> SEQUENCE: 4
cgtcaataaa ggccagttac tacctctatc cttcttcacc aacaacagag ctttacgatc     60
cgaaaacctt cttcactcac gcggcgttgc tccatcagac ttgcgtccat tgtggaagat    120
tccctactgc tgcctcccgt aggagtttgg gccgtgtctc agtcccaatg tggccgatca    180
gtctctcaac tcggctatgc atcatcgcct tggtaagccg ttaccttacc aactagctaa    240
tgcatcgcag gtccatcctt tagcgacagc ttacgccgcc ttttaaactt ctttcatgcg    300
aaagtagctt ttatccggta ttagcatctg tttccaaatg gtatcccaga cttaagggca    360
ggttacccac gcgttactca cccatccgcc gctagcttgt atctatgtcc attccgaaga    420
atttcaatag gcaagctcgc tcgacttgca tgtattaggc acgccgccag cgttc         475

<210> SEQ ID NO 5
<211> LENGTH: 492
<212> TYPE: DNA
<213> ORGANISM: Lactobacillus gasseri

<400> SEQUENCE: 5
tgcagtcgag cgagcttgcc tagatgaatt tggtgcttgc accaaatgaa actagataca     60
agcgagcggc ggacgggtga gtaacacgtg gtaacctgc ccaagagact gggataacac      120
ctggaaacag atgctaatac cggataacaa cactagacgc atgtctagag tttaaaagat    180
ggttctgcta tcactcttgg atggacctgc ggtgcattag ctagttggta aggcaacggc    240
ttaccaaggc aatgatgcat agccgagttg agagactgat cggccacatt gggactgaga    300
cacggcccaa actcctacgg gaggcagcag tagggaatct tccacaatgg acacaagtct    360
gatggagcaa cgccgcgtga gtgaagaagg gttcggctc gtaaagctct gttggtagtg     420
aagaaagata gaggtagtaa ctggcccttta tttgacggta attacttaga aagtcacggc    480
taactacgtg cc                                                        492
```

<210> SEQ ID NO 6
<211> LENGTH: 489
<212> TYPE: DNA
<213> ORGANISM: Lactobacillus gasseri

<400> SEQUENCE: 6

```
tattaccgtc aataaaggcc agttactacc tctatctttc ttcactacca acagagcttt      60
acgagccgaa acccttcttc actcacgcgg cgttgctcca tcagacttgc gtccattgtg     120
gaagattccc tactgctgcc tcccgtagga gtttgggccg tgtctcagtc ccaatgtggc     180
cgatcagtct ctcaactcgg ctatgcatca ttgccttggt aagccgttgc cttaccaact     240
agctaatgca ccgcaggtcc atccaagagt gatagcagaa ccatctttta aactctagac     300
atgcgtctag tgttgttatc cggtattagc atctgtttcc aggtgttatc ccagtctctt     360
gggcaggtta cccacgtgtt actcacccgt ccgccgctcg cttgtatcta gtttcatttg     420
gtgcaagcac caaattcatc taggcaagct cgctcgactt gcatgtatta ggcacgccgc     480
cagcgttcg                                                             489
```

<210> SEQ ID NO 7
<211> LENGTH: 485
<212> TYPE: DNA
<213> ORGANISM: Lactobacillus jensenii

<400> SEQUENCE: 7

```
tgcagtcgag cgagcttgcc tatagaaatt cttcggaatg acatagata caagctagcg       60
gcggatgggt gagtaacgcg tgggtaacct gcccttaagt ctgggatacc atttggaaac     120
agatgctaat accggataaa agctactttc gcatgaaaga gtttaaaag gcggcgtaag     180
ctgtcgctaa aggatggacc tgcgatgcat tagctagttg gtaaggtaac ggcttaccaa     240
ggcgatgatg catagccgag ttgagagact gatcggccac attgggactg agacacggcc     300
caaactccta cgggaggcag cagtagggaa tcttccacaa tggacgaaag tctgatggag     360
caacgccgcg tgagtgaaga aggttttcgg atcgtaaagc tctgttgttg gtgaagaagg     420
atagaggtag taactggcct ttatttgacg gtaatcaacc agaaagtcac ggctaactac     480
gtgcc                                                                  485
```

<210> SEQ ID NO 8
<211> LENGTH: 475
<212> TYPE: DNA
<213> ORGANISM: Lactobacillus jensenii

<400> SEQUENCE: 8

```
cgtcaataaa ggccagttac tacctctatc cttcttcacc aacaacagag ctttacgatc       60
cgaaaacctt cttcactcac gcggcgttgc tccatcagac tttcgtccat tgtggaagat     120
tccctactgc tgcctcccgt aggagtttgg gccgtgtctc agtcccaatg tggccgatca     180
gtctctcaac tcggctatgc atcatcgcct tggtaagccg ttaccttacc aactagctaa     240
tgcatcgcag gtccatccct tagcgacagc ttacgccgcc ttttaaactt ctttcatgcg     300
aaagtagctt ttatccggta ttagcatctg tttccaaatg gtatcccaga cttaagggca     360
ggttacccac gcgttactca cccatccgcc gctagcttgt atctatgtcc attccgaaga     420
atttctatag gcaagctcgc tcgacttgca tgtattaggc acgccgccag cgttc          475
```

<210> SEQ ID NO 9

```
<211> LENGTH: 480
<212> TYPE: DNA
<213> ORGANISM: Lactobacillus jensenii

<400> SEQUENCE: 9
tgcagtcgag cgagcttgcc tattgaaatt cttcggaatg acatagata caagctagcg     60
gcggatgggt gagtaacgcg tgggtaacct gcccttaagt ctgggatacc atttggaaac   120
agatgctaat accggataaa agctactttc gcatgaaaga gtttaaaag gcggcgtaag   180
ctgtcgctaa aggatggacc tgcgatgcat tagctagttg gtaaggtaac ggcttaccaa   240
ggcgatgatg catagccgag ttgagagact gatcggccac attgggactg agacacggcc   300
caaactccta cgggaggcag cagtagggaa tcttccacaa tggacgcaag tctgatggag   360
caacgccgcg tgagtgaaga aggttttcgg atcgtaaagc tctgttgttg gtgaagaagg   420
atagaggtag taactggcct ttatttgacg gtaatcaacc agaaagtcac ggctaactac   480

<210> SEQ ID NO 10
<211> LENGTH: 475
<212> TYPE: DNA
<213> ORGANISM: Lactobacillus jensenii

<400> SEQUENCE: 10
cgtcaataaa ggccagttac tacctctatc cttcttcacc aacaacagag ctttacgatc     60
cgaaaacctt cttcactcac gcggcgttgc tccatcagac ttgcgtccat gtgaagat    120
tccctactgc tgcctcccgt aggagtttgg ccgtgtctc agtcccaatg tggccgatca   180
gtctctcaac tcggctatgc atcatcgcct tggtaagccg ttaccttacc aactagctaa   240
tgcatcgcag gtccatcctt tagcgacagc ttacgccgcc ttttaaactt ctttcatgcg   300
aaagtagctt ttatccggta ttagcatctg tttccaaatg gtatcccaga cttaagggca   360
ggttacccac gcgttactca cccatccgcc gctagcttgt atctatgtcc attccgaaga   420
atttcaatag gcaagctcgc tcgacttgca tgtattaggc acgccgccag cgttc        475

<210> SEQ ID NO 11
<211> LENGTH: 486
<212> TYPE: DNA
<213> ORGANISM: Lactobacillus jensenii

<400> SEQUENCE: 11
tgcagtcgag cgagcttgcc tattgaaatt cttcggaatg acatagata caagctagcg     60
gcggatgggt gagtaacgcg tgggtaacct gcccttaagt ctgggatacc atttggaaac   120
agatgctaat accggataaa agctactttc gcatgaaaga gtttaaaag gcggcgtaag   180
ctgtcgctaa aggatggacc tgcgatgcat tagctagttg gtaaggtaac ggcttaccaa   240
ggcgatgatg catagccgag ttgagagact gatcggccac attgggactg agacacggcc   300
caaactccta cgggaggcag cagtagggaa tcttccacaa tggacgcaag tctgatggag   360
caacgccgcg tgagtgaaga aggttttcgg atcgtaaagc tctgttgttg gtgaagaagg   420
atagaggtag taactggcct ttatttgacg gtaatcaacc agaaagtcac ggctaactac   480
gtgcca                                                              486

<210> SEQ ID NO 12
<211> LENGTH: 474
<212> TYPE: DNA
<213> ORGANISM: Lactobacillus jensenii

<400> SEQUENCE: 12
```

```
cgtcaataaa ggccagttac tacctctatc cttcttcacc aacaacagag ctttacgatc      60
cgaaaacctt cttcactcac gcggcgttgc tccatcagac ttgcgtccat tgtggaagat     120
tccctactgc tgcctcccgt aggagtttgg gccgtgtctc agtcccaatg tggccgatca     180
gtctctcaac tcggctatgc atcatcgcct tggtaagccg ttaccttacc aactagctaa     240
tgcatcgcag gtccatcctt tagcgacagc ttacgccgcc ttttaaactt ctttcatgcg     300
aaagtagctt ttatccggta ttagcatctg tttccaaatg gtatcccaga cttaagggca     360
ggttacccac gcgttactca cccatccgcc gctagcttgt atctatgtcc attccgaaga     420
atttcaatag gcaagctcgc tcgacttgca tgtattaggc acgccgccag cgtt           474
```

<210> SEQ ID NO 13
<211> LENGTH: 253
<212> TYPE: DNA
<213> ORGANISM: Lactobacillus jensenii

<400> SEQUENCE: 13

```
cgagcttgcc tatataattt cttctgaatg acataatac aagctagcgg cggatgggtg      60
agtaacgcgt gagtaacctg cccttaagtc ggggatacca tttggaaaca gatgctaata    120
ccggataaaa gctactttcc catgaaagaa gtttaaaagg cggtgtaagc tgtcgctaaa    180
ggatggacct gcgatgcatt agctagttgg taaggtaacg gcttaccaag gcgatgatgc    240
atacccgagt tga                                                       253
```

<210> SEQ ID NO 14
<211> LENGTH: 343
<212> TYPE: DNA
<213> ORGANISM: Lactobacillus jensenii

<400> SEQUENCE: 14

```
ctttacgatc cgaaagcctt cttcactcac gcggcgtggc tccatcagac ttgcgcccat     60
tgtggaagat tccctactgc tgcctcccgt aggagtttgg gccgtgtctc agtcccaatg    120
tggccgatca gtctctcaaa tcggctatgc atcatcgcct tggtaagccg ttaccttacc    180
aactagctaa tgcatcgcag gtccatccta tagcgacagc ttacgccgtc ttttaaactt    240
ctttcatgcg aatgtagctt ttatgcggta ttagcatctg tttccaaatg gtatcccaga    300
cttaagggca ggttacctac gcgttactca cccatccgcc gct                      343
```

<210> SEQ ID NO 15
<211> LENGTH: 480
<212> TYPE: DNA
<213> ORGANISM: Lactobacillus jensenii

<400> SEQUENCE: 15

```
tgcagtcgag cgagcttgcc tattgaaatt cttcggaatg acatagata caagctagcg      60 gcggatgggt gagtaacgcg tgggtaacct gcccttaagt ctgggatacc atttggaaac    120
agatgctaat accggataaa agctactttc gcatgaaaga agtttaaaag gcggcgtaag    180
ctgtcgctaa aggatggacc tgcgatgcat tagctagttg gtaaggtaac ggcttaccaa    240
ggcgatgatg catagccgag ttgagagact gatcggccac attgggactg agacacggcc    300
caaactccta cgggaggcag cagtagggaa tcttccacaa tggacgcaag tctgatggag    360
caacgccgcg tgagtgaaga aggttttcgg atcgtaaagc tctgttgttg gtgaagaagg    420
atagaggtag taactggcct ttatttgacg gtaatcaacc agaaagtcac ggctaactac    480
```

<210> SEQ ID NO 16
<211> LENGTH: 475
<212> TYPE: DNA
<213> ORGANISM: Lactobacillus jensenii

<400> SEQUENCE: 16

| | | |
|---|---|---|
| cgtcaataaa ggccagttac tacctctatc cttcttcacc aacaacagag ctttacgatc | 60 |
| cgaaaacctt cttcactcac gcggcgttgc tccatcagac ttgcgtccat tgtggaagat | 120 |
| tccctactgc tgcctcccgt aggagtttgg gccgtgtctc agtcccaatg tggccgatca | 180 |
| gtctctcaac tcggctatgc atcatcgcct tggtaagccg ttaccttacc aactagctaa | 240 |
| tgcatcgcag gtccatcctt tagcgacagc ttacgccgcc ttttaaactt ctttcatgcg | 300 |
| aaagtagctt ttatccggta ttagcatctg tttccaaatg gtatcccaga cttaagggca | 360 |
| ggttacccac gcgttactca cccatccgcc gctagcttgt atctatgtcc attccgaaga | 420 |
| atttcaatag gcaagctcgc tcgacttgca tgtattaggc acgccgccag cgttc | 475 |

<210> SEQ ID NO 17
<211> LENGTH: 487
<212> TYPE: DNA
<213> ORGANISM: Lactobacillus jensenii

<400> SEQUENCE: 17

| | | |
|---|---|---|
| tgcagtcgag cgagcttgcc tattgaaatt cttcggaatg acatagata caagctagcg | 60 |
| gcggatgggt gagtaacgcg tgggtaacct gcccttaagt ctgggatacc atttggaaac | 120 |
| agatgctaat accggataaa agctactttc gcatgaaaga gtttaaaag gcggcgtaag | 180 |
| ctgtcgctaa aggatggacc tgcgatgcat tagctagttg gtaaggtaac ggcttaccaa | 240 |
| ggcgatgatg catagccgag ttgagagact gatcggccac attgggactg agacacggcc | 300 |
| caaactccta cgggaggcag cagtagggaa tcttccacaa tggacgcaag tctgatggag | 360 |
| caacgccgcg tgagtgaaga aggttttcgg atcgtaaagc tctgttgttg gtgaagaagg | 420 |
| atagaggtag taactggcct ttatttgacg gtaatcaacc agaaagtcac ggctaactac | 480 |
| gtgccag | 487 |

<210> SEQ ID NO 18
<211> LENGTH: 473
<212> TYPE: DNA
<213> ORGANISM: Lactobacillus jensenii

<400> SEQUENCE: 18

| | | |
|---|---|---|
| cgtcaataaa ggccagttac tacctctatc cttcttcacc aacaacagag ctttacgatc | 60 |
| cgaaaacctt cttcactcac gcggcgttgc tccatcagac ttgcgtccat tgtggaagat | 120 |
| tccctactgc tgcctcccgt aggagtttgg gccgtgtctc agtcccaatg tggccgatca | 180 |
| gtctctcaac tcggctatgc atcatcgcct tggtaagccg ttaccttacc aactagctaa | 240 |
| tgcatcgcag gtccatcctt tagcgacagc ttacgccgcc ttttaaactt ctttcatgcg | 300 |
| aaagtagctt ttatccggta ttagcatctg tttccaaatg gtatcccaga cttaagggca | 360 |
| ggttacccac gcgttactca cccatccgcc gctagcttgt atctatgtcc attccgaaga | 420 |
| atttcaatag gcaagctcgc tcgacttgca tgtattaggc acgccgccag cgt | 473 |

<210> SEQ ID NO 19
<211> LENGTH: 849
<212> TYPE: DNA
<213> ORGANISM: Lactobacillus jensenii

<400> SEQUENCE: 19

```
gcagtcgagc gagcttgcct atagaagttc ttcggaatgg aaatagatac aagctagcgg      60
cggatgggtg agtaacgcgt gggtaacctg cccttaagtc tgggatacca tttggaaaca     120
gatgctaata ccggataaaa gctactttcg catgaaagaa gtttaaaagg cggcgtaagc     180
tgtcgctaaa ggatggacct gcgatgcatt agctagttgg taaggtaacg gcttaccaag     240
gcgatgatgc atagccgagt tgagagactg atcggccaca ttgggactga gacacggccc     300
aaactcctac gggaggcagc agtagggaat cttccacaat ggacgaaagt ctgatggagc     360
aacgccgcgt gagtgaagaa ggttttcgga tcgtaaagct ctgttgttgg tgaagaagga     420
tagaggtagt aactggcctt tatttgacgg taatcaacca gaaagtcacg gctaactacg     480
tgccagcagc cgcggtaata cgtaggtggc aagcgttgtc cggatttatt gggcgtaaag     540
cgagcgcagg cggattgata agtctgatgt gaaagccttc ggctcaaccg aagaactgca     600
tcagaaactg tcaatcttga gtgcagaaga ggagagtgga actccatgtg tagcggtgga     660
atgcgtagat atatggaaga acaccagtgg cgaaggcggc tctctggtct gtaactgacg     720
ctgaggctcg aaagcatggg tagcgaacag gattagatac cctggtagtc catgccgtaa     780
acgatgagtg ctaagtgttg ggaggtttcc gcctctcagt gctgcagcta acgcattaag     840
cactccgcc                                                             849
```

<210> SEQ ID NO 20
<211> LENGTH: 898
<212> TYPE: DNA
<213> ORGANISM: Lactobacillus jensenii

<400> SEQUENCE: 20

```
gcggctggct ccaaggttac ctcaccgact ttgggtgtta caaactctca tggtgtgacg      60
ggcggtgtgt acaaggcccg ggaacgtatt caccgcggcg tgctgatccg cgattactag     120
cgattccagc ttcgtgtagg cgagttgcag cctacagtcc gaactgagaa cagctttaag     180
agatccgctt gccttcacag gttcgcttct cgttgtactg cccattgtag cacgtgtgta     240
gcccaggtca taagggcat gatgacttga cgtcatcccc accttcctcc ggtttgtcac     300
cggcagtctc aatagagtgc ccaacttaat gctggcaact attaacaagg gttgcgctcg     360
ttgcgggact aacccaaca tctcacgaca cgagctgacg acagccatgc accacctgtc     420
tctttgtccc cgaagggaaa acctaatctc ttaggtggtc aaaggatgtc aagacctggt     480
aaggttcttc gcgttgcttc gaattaaacc acatgctcca ccgcttgtgc gggccccgt      540
caattccttt gagtttcaac cttgcggtcg tactccccag gcggagtgct taatgcgtta     600
gctgcagcac tgagaggcgg aaacctccca acacttagca ctcatcgttt acggcatgga     660
ctaccagggt atctaatcct gttcgctacc catgctttcg agcctcagcg tcagttacag     720
accagagagc cgccttcgcc actggtgttc ttccatatat ctacgcattc caccgctaca     780
catggagttc cactctcctc ttctgcactc aagattgaca gtttctgatg cagttcttcg     840
gttgagccga aggctttcac atcagactta tcaatccgcc tgcgctcgct ttacgccc       898
```

<210> SEQ ID NO 21
<211> LENGTH: 496
<212> TYPE: DNA
<213> ORGANISM: Lactobacillus gasseri

<400> SEQUENCE: 21

```
atacctgcag tcgagcgagc ttgcctagat gaatttggtg cttgcaccag atgaaactag    60
atacaagcga gcggcggacg ggtgagtaac acgtgggtaa cctgcccaag agactgggat   120
aacacctgga aacagatgct aataccggat aacaacacta gacgcatgtc tagagtttaa   180
aagatggttc tgctatcact cttggatgga cctgcggtgc attagctagt tggtaaggca   240
acggcttacc aaggcaatga tgcatagccg agttgagaga ctgatcggcc acattgggac   300
tgagacacgg cccaaactcc tacgggaggc agcagtaggg aatcttccac aatggacgca   360
agtctgatgg agcaacgccg cgtgagtgaa gaagggtttc ggctcgtaaa gctctgttgg   420
tagtgaagaa agatagaggt agtaactggc ctttatttga cggtaattac ttagaaagtc   480
acggctaact acgtgc                                                  496

<210> SEQ ID NO 22
<211> LENGTH: 498
<212> TYPE: DNA
<213> ORGANISM: Lactobacillus gasseri

<400> SEQUENCE: 22
tagtattacc gtcaataaag gccagttact acctctatct ttcttcacta ccaacagagc    60
tttacgagcc gaaacccttc ttcactcacg cggcgttgct ccatcagact tgcgtccatt   120
gtggaagatt ccctactgct gcctcccgta ggagtttggg ccgtgtctca gtcccaatgt   180
ggccgatcag tctctcaact cggctatgca tcattgcctt ggtaagccgt tgccttacca   240
actagctaat gcaccgcagg tccatccaag agtgatagca gaaccatctt ttaaactcta   300
gacatgcgtc tagtgttgtt atccggtatt agcatctgtt tccaggtgtt atcccagtct   360
cttgggcagg ttacccacgt gttactcacc cgtccgccgc tcgcttgtat ctagtttcat   420
ctggtgcaag caccaaattc atctaggcaa gctcgctcga cttgcatgta ttaggcacgc   480
cgccagcgtt cgtcctga                                                498

<210> SEQ ID NO 23
<211> LENGTH: 498
<212> TYPE: DNA
<213> ORGANISM: Lactobacillus gasseri

<400> SEQUENCE: 23
atacctgcag tcgagcgagc ttgcctagat gaatttggtg cttgcaccaa atgaaactag    60
atacaagcga gcggcggacg ggtgagtaac acgtgggtaa cctgcccaag agactgggat   120
aacacctgga aacagatgct aataccggat aacaacacta gacgcatgtc tagagtttaa   180
aagatggttc tgctatcact cttggatgga cctgcggtgc attagctagt tggtaaggta   240
acggcttacc aaggcaatga tgcatagccg agttgagaga ctgatcggcc acattgggac   300
tgagacacgg cccaaactcc tacgggaggc agcagtaggg aatcttccac aatggacgca   360
agtctgatgg agcaacgccg cgtgagtgaa gaagggtttc ggctcgtaaa gctctgttgg   420
tagtgaagaa agatagaggt agtaactggc ctttatttga cggtaattac ttagaaagtc   480
acggctaact acgtgcca                                                498

<210> SEQ ID NO 24
<211> LENGTH: 499
<212> TYPE: DNA
<213> ORGANISM: Lactobacillus gasseri

<400> SEQUENCE: 24
ctagtattac cgtcaataaa ggccagttac tacctctatc tttcttcact accaacagag    60
```

```
ctttacgagc cgaaacccctt cttcactcac gcggcgttgc tccatcgac ttgcgtccat     120 tgtggaagat tccctactgc tgcctcccgt aggagtttgg gccgtgtctc agtcccaatg     180
tggccgatca gtctctcaac tcggctatgc atcattgcct tggtaagccg ttaccttacc     240
aactagctaa tgcaccgcag gtccatccaa gagtgataga gaaccatct tttaaactct       300 agacatgcgt ctagtgttgt tatccggtat tagcatctgt ttccaggtgt tatcccagtc     360
tcttgggcag gttacccacg tgttactcac ccgtccgccg ctcgcttgta tctagtttca     420
tttggtgcaa gcaccaaatt catctaggca agctcgctcg acttgcatgt attaggcacg     480
ccgccagcgt tcgtcctga                                                  499

<210> SEQ ID NO 25
<211> LENGTH: 796
<212> TYPE: DNA
<213> ORGANISM: Lactobacillus crispatus

<400> SEQUENCE: 25
gcgagcggac taacagattt acttcggtaa tgacgttagg aaagcgagcg gcggatgggt      60
gagtaacacg tggggaacct gcccccatagt ctgggatacc acttggaaac aggtgctaat    120
accggataag aaagcagatc gcatgatcag cttttaaaag gcggcgtaag ctgtcgctat     180
gggatggccc cgcggtgcat tagctagttg gtaaggtaaa ggcttaccaa ggcgatgatg     240
catagccgag ttgagagact gatcggccac attgggactg agacacggcc caaactccta     300
cgggaggcag cagtagggaa tcttccacaa tggacgcaag tctgatggag caacgccgcg     360
tgagtgaaga aggttttcgg atcgtaaagc tctgttgttg gtgaagaagg atagaggtag     420
taactggcct ttatttgacg gtaatcaacc agaaagtcac ggctaactac gtgccagcag     480
ccgcggtaat acgtaggtgg caagcgttgt ccggatttat tgggcgtaaa gcgagcgcag     540
gcggaagaat aagtctgatg tgaaagccct cggcttaacc gaggaactgc atcggaaact     600 gttttttcttg agtgcagaag acgagagtgg aactccatgt gtagcggtgg aatgcgtaga     660 tatatgaag aacaccagtg gcgaaggcgg ctctctggtc tgcaactgac gctgaggctc       720
gaaagcatgg gtagcgaaca ggattagata ccctggtagt ccatgccgta aacgatgagt      780
gctaagtgtt gggagg                                                     796

<210> SEQ ID NO 26
<211> LENGTH: 895
<212> TYPE: DNA
<213> ORGANISM: Lactobacillus crispatus

<400> SEQUENCE: 26
ggttaggcca ccggctttgg gcattgcaga ctcccatggt gtgacgggcg gtgtgtacaa      60
ggcccgggaa cgtattcacc gcggcgtgct gatccgcgat tactagcgat tccagcttcg    120
tgcagtcgat tgcagactg cagtccgaac tgagaacagc tttcagagat tcgcttgcct      180
tcgcaggctc gcttctcgtt gtactgccca ttgtagcacg tgtgtagccc aggtcataag    240
gggcatgatg acttgacgtc atccccacct tcctccggtt tgtcaccggc agtctcatta    300
gagtgcccaa cttaatgctg gcaactaata acaagggttg cgctcgttgc gggacttaac    360
ccaacatctc acgacacgag ctgacgacag ccatgcacca cctgtcttag cgtccccgaa    420
gggaactttg tatctctaca aatggcacta gatgtcaaga cctggtaagg ttcttcgcgt    480
tgcttcgaat taaaccacat gctccaccgc ttgtgcgggc ccccgtcaat tcctttgagt    540
```

| | |
|---|---|
| ttcaaccttg cggtcgtact ccccaggcgg agtgcttaat gcgttagctg cagcactgag | 600 |
| aggcggaaac ctcccaacac ttagcactca tcgtttacgg catgcactac cagggtatct | 660 |
| aatcctgttc gctacccatg ctttcgagcc tcagcgtcag ttgcagacca gagagccgcc | 720 |
| ttcgccactg gtgttcttcc atatatctac gcattccacg ctacacatgg agttccactc | 780 |
| tcctcttctg cactcaagaa aaacagtttc cgatgcagtt cctcggttaa gccgagggct | 840 |
| ttcacatcaa acttattctt ccgcctgcgc tcgctttacg cccaataaat ccgga | 895 |

<210> SEQ ID NO 27
<211> LENGTH: 814
<212> TYPE: DNA
<213> ORGANISM: Lactobacillus crispatus

<400> SEQUENCE: 27

| | |
|---|---|
| tgcagtcgag cgagcggact aacagattta cttcggtaat gacgttagga aagcgagcgg | 60 |
| cggatgggtg agtaacacgt ggggaacctg ccccatagtc tgggatacca cttggaaaca | 120 |
| ggtgctaata ccgdataaga aagcagatcg catgatcagc ttttaaaagg cggcgtaagc | 180 |
| tgtcgctatg ggatggcccc gcggtgcatt agctagttgg taaggtaaag cttaccaag | 240 |
| gcgatgatgc atagccgagt tgagagactg atcggccaca ttgggactga cacggcca | 300 |
| aactcctacg ggaggcagca gtagggaatc ttccacaatg gacgcaagtc tgatggagca | 360 |
| acgccgcgtg agtgaagaag gttttcggat cgtaaagctc tgttgttggt gaagaaggat | 420 |
| agaggtagta actggccttt atttgacggt aatcaaccag aaagtcacgg ctaactacgt | 480 |
| gccagcagcc gcggtaatac gtaggtgcaa agcgttgtcc ggatttattg ggcgtaaagc | 540 |
| gagcgcaggc ggaagaataa gtctgatgtg aaagccctcg gcttaaccga gaactgcat | 600 |
| cggaaactgt ttttcttgag tgcagaagag gagagtggaa ctccatgtgc tctctggtct | 660 |
| gcaactgacg ctgaggctcg aaagcatggg tagcgaacag gatagatacc ctggtagtcc | 720 |
| atgccgtaaa cgatgagtgc taagtgttgg gaggtttccg cctctcagtg ctgcagctaa | 780 |
| cgcattaagc actccgccgg gggagtacga ccgc | 814 |

<210> SEQ ID NO 28
<211> LENGTH: 853
<212> TYPE: DNA
<213> ORGANISM: Lactobacillus crispatus

<400> SEQUENCE: 28

| | |
|---|---|
| aaggttaggc caccggcttt gggcattgca gactcccatg gtgtgacggg cggtgtgtac | 60 |
| aaggcccggg aacgtattca ccgcggcgtg ctgatccgcg attactagcg attccagctt | 120 |
| cgtgcagtcg agttgcagac tgcagtccga actgagaaca gctttcagag attcgcttgc | 180 |
| cttcgcaggc tcgcttctcg ttgtactgcc cattgtagca cgtgtgtagc ccaggtcata | 240 |
| aggggcatga tgacttgacg tcatccccac cttcctccgg tttgtcaccg gcagtctcat | 300 |
| tagagtgccc aacttaatgc tggcaactaa taacaaggg tgcgctcgtt gcgctgtctt | 360 |
| agcgtccccg aagggaactt tgtatctcta caaatggcac tagatgtcaa gacctggtaa | 420 |
| ggttcttcgc gttgcttcga attaaaccac atgctccacc gcttgtgcgg gccccgtca | 480 |
| attcctttga gtttcaacct tgcggtcgta ctccccaggc ggagtgctta atgcgttagc | 540 |
| tgcagcactg agaggcggaa acctcccaac acttagcact catcgtttac ggcatggact | 600 |
| accagggtat ctaatcctgt tcgctaccca tgctttcgag cctcagcgtc agttgcagac | 660 |
| cagagagccg ccttcgccac tggtgttctt ccatatatct acgcattcca ccgctacaca | 720 |

```
tggagttcca ctctcctctt ctgcactcaa gaaaaacagt ttccgatgca gttcctcggt    780
taagccgagg gctttcacat cagacttatt cttccgcctg cgctcgcttt acgcccaata    840
aatccggaca acg                                                      853

<210> SEQ ID NO 29
<211> LENGTH: 561
<212> TYPE: DNA
<213> ORGANISM: Lactobacillus crispatus

<400> SEQUENCE: 29
tatgggatgg ccccgcggtg cattaactag ttggtaaggt aaaggcttac caaggcgatg     60
atgcatagcc gagttgagag actgatcggc cacattggga ctgagacacg gcccaaactc    120
ctacgggagg cagcagtagg gaatcttcca caatggacgc aagtctgatg gagcaacgcc    180
gcgtgagtga agaaggtttt cggatcgtaa agctctgttg ttggtgaaga aggatagagg    240
tagtaactgg cctttatttg acggtaatca accagaaagt cacggctaac tacgtgccag    300
cagccgcggt aatacgtagg tggcaagcgt tgtccggatt tattgggcgt aaagcgagcg    360
caggcggaag aataagtctg atgtgaaagc cctcggctta accgaggaac tgcatcggaa    420
actgtttttc ttgagtgcag aagaggagag tggaactcca tgtgtagcgg tggaatgcgt    480
agatatatgg aagaacacca gtggcgaagg cggctctctg gtctgcaact gacgctgagg    540
ctcgaaagca tgggtagcga a                                             561

<210> SEQ ID NO 30
<211> LENGTH: 384
<212> TYPE: DNA
<213> ORGANISM: Lactobacillus crispatus

<400> SEQUENCE: 30
gacttgatgt catccccacc ttcctccggt ttgtcaccgg cagtctcatt agagtgccca     60
acttaatgct ggcaactaat aacaagggtt gcgctcgttg cgggacttaa cccaacatct    120
cacgacacga gctgacgaca gccatgcacc acctgtctta gcgtcccgaa gggaactttt    180
gtatctctac aaatggcact agatgtcaag acctggtaag gttcttcgcg ttgcttcgaa    240
ttaaaccaca tgctccaccg cttgtgcggg ccccgtcaa ttcctttgag tttcaacctt    300
gcggtcgtac tccccaggcg gagtgcttaa tgcgttagct gcagcactga gaggcggaaa    360
cctcccaaca cttagcactc atcg                                          384

<210> SEQ ID NO 31
<211> LENGTH: 620
<212> TYPE: DNA
<213> ORGANISM: Lactobacillus crispatus

<400> SEQUENCE: 31
atcgcatgat caggttttaa aaagaagcgt aagctgtcgc tatgggatgg ccccgcggtg     60
cattaactag ttggtaaggt aaaggcttac caaggcgatg atgcatagcc gagttgagag    120
actgatcggc cacattggga ctgagacacg gcccaaactc ctacgggagg cagcagtagg    180
gaatcttcca caatggacgc aagtctgatg gagcaacgcc gcgtgagtga agaaggtttt    240
cggatcgtaa agctctgttg ttggtgaaga aggatagagg tagtaactgg cctttatttg    300
acggtaatca accagaaagt cacggctaac tacgtgccag cagccgcggt aatacgtagg    360
tggcaagcgt tgtccggatt tattgggcgt aaagcgagcg caggcggaag aataagtctg    420
```

```
atgtgaaagc cctcggctta accgaggaac tgcatcggaa actgtttttc ttgagtgcag    480
aagaagagag tggaactcca tgtgtagcgg tggaatgcgt agatatatgg aagaacacca    540
gtggcgaaag gcggctctct ggtctgcaac tgacgctgag gctcgaaagc atgggtagcg    600
aacaggatta aataccctgg                                                620

<210> SEQ ID NO 32
<211> LENGTH: 608
<212> TYPE: DNA
<213> ORGANISM: Lactobacillus crispatus

<400> SEQUENCE: 32
gatgacttgt cgtcatcccc accttcctcc ggtttgacac cggcagtctc attagagtgc     60
ccaacttaat gctggcaact aataacaagg gttgcgctcg ttgcgggact aacccaaca    120 tctcacgaca cgagctgacg acagccatgc accacctgtc ttagcgtccc cgaagggaac   180
tttgtatctc tacaaatggc actagatgtc aagacctggt aaggttcttc gcgttgcttc    240
gaattaaacc acatgctcca ccgcttgtgc gggccccgt caattccttt gagttttcaac    300 cttgcggtcg tactccccag gcggagtgct taatgcgtta gctgcagcac tgagaggcgg    360
aaacctccca acacttagca ctcatcgttt acggcatgga ctaccagggt atctaatcct    420
gttcgctacc catgctttcg agcctcagcg tcagttgcag accagagagc cgccttcgcc    480
actggtgttc ttccatatat ctacgcattc caccgctaca catggagttc cactctcctc    540
ttctgcactc aaaaaaaaca gtttccgatg cagttcctcg gttaacccaa gggctttcac    600
atcaaact                                                             608

<210> SEQ ID NO 33
<211> LENGTH: 486
<212> TYPE: DNA
<213> ORGANISM: Lactobacillus jensenii

<400> SEQUENCE: 33
tgcagtcgag cgagcttgcc tattgaaatt cttcggaatg acatagata caagctagcg     60 gcggatgggt gagtaacgcg tgggtaacct gcccttaagt ctgggatacc atttggaaac    120
agatgctaat accggataaa agctactttc gcatgaaaga agtttaaaag gcggcgtaag    180
ctgtcgctaa aggatggacc tgcgatgcat tagctagttg gtaaggtaac ggcttaccaa    240
ggcgatgatg catagccgag ttgagagact gatcggccac attgggactg agacacggcc    300
caaactccta cgggaggcag cagtagggaa tcttccacaa tggacgcaag tctgatggag    360
caacgccgcg tgagtgaaga aggttttcgg atcgtaaagc tctgttgttg gtgaagaagg    420
atagaggtag taactggcct ttatttgacg gtaatcaacc agaaagtcac ggctaactac    480
gtgcca                                                               486

<210> SEQ ID NO 34
<211> LENGTH: 482
<212> TYPE: DNA
<213> ORGANISM: Lactobacillus jensenii

<400> SEQUENCE: 34
cgtcaataaa ggccagttac tacctctatc cttcttcacc aacaacagag ctttacgatc     60 cgaaaaccctt cttcactcac gcggcgttgc tccatcagac ttgcgtccat tgtggaagat    120
tccctactgc tgcctcccgt aggagtttgg gccgtgtctc agtcccaatg tggccgatca    180
gtctctcaac tcggctatgc atcatcgcct tggtaagccg ttaccttacc aactagctaa    240
```

```
tgcatcgcag gtccatcctt tagcgacagc ttacgccgcc ttttaaactt ctttcatgcg      300
aaagtagctt ttatccggta ttagcatctg tttccaaatg gtatcccaga cttaagggca      360
ggttacccac gcgttactca cccatccgcc gctagcttgt atctatgtcc attccgaaga      420
atttcaatag gcaagctcgc tcgacttgca tgtattaggc acgccgccag cgttcgtcct      480
ga                                                                    482
```

<210> SEQ ID NO 35
<211> LENGTH: 480
<212> TYPE: DNA
<213> ORGANISM: Lactobacillus jensenii

<400> SEQUENCE: 35

```
tgcagtcgag cgagcttgcc tatagaagtt cttcggaatg gacatagata caagctagcg       60
gcggatgggt gagtaacgcg tgggtaacct gcccttaagt ctgggatacc atttggaaac      120
agatgctaat accggataaa agctactttc gcatgaaaga gtttaaaag  gcggcgtaag      180 ctgtcgctaa aggatggacc tgcgatgcat tagctagttg gtaaggtaac ggcttaccaa      240
ggcgatgatg catagccgag ttgagagact gatcggccac attgggactg agacacggcc      300
caaactccta cgggaggcag cagtagggaa tcttccacaa tggacgaaag tctgatggag      360
caacgccgcg tgagtgaaga aggttttcgg atcgtaaagc tctgttgttg gtgaagaagg      420
atagaggtag taactggcct ttatttgacg gtaatcaacc agaaagtcac ggctaactac      480
```

<210> SEQ ID NO 36
<211> LENGTH: 475
<212> TYPE: DNA
<213> ORGANISM: Lactobacillus jensenii

<400> SEQUENCE: 36

```
cgtcaataaa ggccagttac tacctctatc cttcttcacc aacaacagag ctttacgatc       60
cgaaaacctt cttcactcac gcggcgttgc tccatcagac tttcgtccat tgtggaagat      120
tccctactgc tgcctcccgt aggagtttgg gccgtgtctc agtcccaatg tggccgatca      180
gtctctcaac tcggctatgc atcatcgcct tggtaagccg ttaccttacc aactagctaa      240
tgcatcgcag gtccatcctt tagcgacagc ttacgccgcc ttttaaactt ctttcatgcg      300
aaagtagctt ttatccggta ttagcatctg tttccaaatg gtatcccaga cttaagggca      360
ggttacccac gcgttactca cccatccgcc gctagcttgt atctatgtcc attccgaaga      420
acttctatag gcaagctcgc tcgacttgca tgtattaggc acgccgccag cgttc           475
```

<210> SEQ ID NO 37
<211> LENGTH: 472
<212> TYPE: DNA
<213> ORGANISM: Lactobacillus jensenii

<400> SEQUENCE: 37

```
gcttgcctat agaagttctt cggaatggac atagatacaa gctagcggcg gatgggtgag       60
taacgcgtgg gtaacctgcc cttaagtctg ggataccatt tggaaacaga tgctaatacc      120
ggataaaagc tactttcgca tgaaagaagt ttaaaaggcg cgtaagctg  tcgctaaagg      180 atggacctgc gatgcattag ctagttggta aggtaacggc ttaccaaggc gatgatgcat      240
agctgagttg agagactgat cggccacatt gggactgaga cacggcccaa actcctacgg      300
gaggcagcag tagggaatct tccacaatgg acgaaagtct gatggagcaa cgccgcgtga      360
```

```
gtgaagaagg ttttcggatc gtaaagctct gttgttggtg aagaaggata gaggtagtaa      420
ctggccttta tttgacggta atcaaccaga aagtcacggc taactacgtg cc              472
```

<210> SEQ ID NO 38
<211> LENGTH: 479
<212> TYPE: DNA
<213> ORGANISM: Lactobacillus jensenii

<400> SEQUENCE: 38

```
ataaaggcca gttactacct ctatccttct tcaccaacaa cagagcttta cgatccgaaa      60
accttcttca ctcacgcggc gttgctccat cagactttcg tccattgtgg aagattccct    120
actgctgcct cccgtaggag tttgggccgt gtctcagtcc caatgtggcc gatcagtctc    180
tcaactcagc tatgcatcat cgccttggta agccgttacc ttaccaacta gctaatgcat    240
cgcaggtcca tcctttagcg acagcttacg ccgcctttta aacttctttc atgcgaaagt    300 agctttatc cggtattagc atctgttttc aaatggtatc ccagacttaa gggcaggtta    360
cccacgcgtt actcacccat ccgccgctag cttgtatcta tgtccattcc gaagaacttc    420
tataggcaag ctcgctcgac ttgcatgtat taggcacgcc gccagcgttc gtcctgagc    479
```

<210> SEQ ID NO 39
<211> LENGTH: 486
<212> TYPE: DNA
<213> ORGANISM: Lactobacillus jensenii

<400> SEQUENCE: 39

```
tgcagtcgag cgagcttgcc tattgaaatt cttcggaatg acatagata caagctagcg      60 gcggatgggt gagtaacgcg tgggtaacct gcccttaagt ctgggatacc atttggaaac    120
agatgctaat accggataaa agctactttc gcatgaaaga agtttaaaag gcggcgtaag    180
ctgtcgctaa aggatggacc tgcgatgcat tagctagttg gtaaggtaac ggcttaccaa    240
ggcgatgatg catagccgag ttgagagact gatcggccac attgggactg agacacggcc    300
caaactccta cgggaggcag cagtagggaa tcttccacaa tggacgcaag tctgatggag    360
caacgccgcg tgagtgaaga aggttttcgg atcgtaaagc tctgttgttg gtgaagaagg    420
atagaggtag taactggcct ttatttgacg gtaatcaacc agaaagtcac ggctaactac    480
gtgcca                                                              486
```

<210> SEQ ID NO 40
<211> LENGTH: 485
<212> TYPE: DNA
<213> ORGANISM: Lactobacillus jensenii

<400> SEQUENCE: 40

```
cgtcaataaa ggccagttac tacctctatc cttcttcacc aacaacagag ctttacgatc      60
cgaaaacctt cttcactcac gcggcgttgc tccatcagac ttgcgtccat tgtggaagat    120
tccctactgc tgcctcccgt aggagtttgg gccgtgtctc agtcccaatg tggccgatca    180
gtctctcaac tcggctatgc atcatcgcct tggtaagccg ttaccttacc aactagctaa    240
tgcatcgcag gtccatcctt tagcgacagc ttacgccgcc ttttaaactt ctttcatgcg    300
aaagtagctt ttatccggta ttagcatctg tttccaaatg gtatcccaga cttaagggca    360
ggttacccac gcgttactca cccatccgcc gctagcttgt atctatgtcc attccgaaga    420
atttcaatag gcaagctcgc tcgacttgca tgtattaggc acgccgccag cgttcgtcct    480
gagcc                                                              485
```

<210> SEQ ID NO 41
<211> LENGTH: 480
<212> TYPE: DNA
<213> ORGANISM: Lactobacillus jensenii

<400> SEQUENCE: 41

```
tgcagtcgag cgagcttgcc tattgaaatt cttcggaatg gacatagata caagctagcg      60
gcggatgggt gagtaacgcg tgggtaacct gcccttaagt ctgggatacc atttggaaac     120
agatgctaat accggataaa agctactttc gcatgaaaga gtttaaaag gcggcgtaag      180
ctgtcgctaa aggatggacc tgcgatgcat tagctagttg gtaaggtaac ggcttaccaa     240
ggcgatgatg catagccgag ttgagagact gatcggccac attgggactg agacacggcc     300
caaactccta cgggaggcag cagtagggaa tcttccacaa tggacgcaag tctgatggag     360
caacgccgcg tgagtgaaga aggttttcgg atcgtaaagc tctgttgttg gtgaagaagg     420
atagaggtag taactggcct ttatttgacg gtaatcaacc agaaagtcac ggctaactac     480
```

<210> SEQ ID NO 42
<211> LENGTH: 482
<212> TYPE: DNA
<213> ORGANISM: Lactobacillus jensenii

<400> SEQUENCE: 42

```
cgtcaataaa ggccagttac tacctctatc cttcttcacc aacaacagag ctttacgatc      60
cgaaaacctt cttcactcac gcggcgttgc tccatcagac ttgcgtccat tgtggaagat     120
tccctactgc tgcctcccgt aggagtttgg gccgtgtctc agtcccaatg tggccgatca     180
gtctctcaac tcggctatgc atcatcgcct tggtaagccg ttaccttacc aactagctaa     240
tgcatcgcag gtccatcctt tagcgacagc ttacgccgcc ttttaaactt ctttcatgcg     300
aaagtagctt ttatccggta ttagcatctg tttccaaatg gtatcccaga cttaagggca     360
ggttacccac gcgttactca cccatccgcc gctagcttgt atctatgtcc attccgaaga     420
atttcaatag gcaagctcgc tcgacttgca tgtattaggc acgccgccag cgttcgtcct     480
ga                                                                   482
```

<210> SEQ ID NO 43
<211> LENGTH: 490
<212> TYPE: DNA
<213> ORGANISM: Lactobacillus jensenii

<400> SEQUENCE: 43

```
tgcagtcgag cgagcttgcc tatagaaatt cttcggaatg gacatagata caagctagcg      60
gcggatgggt gagtaacgcg tgggtaacct gcccttaagt ctgggatacc atttggaaac     120
agatgctaat accggataaa agctactttc gcatgaaaga gtttaaaag gcggcgtaag      180
ctgtcgctaa aggatggacc tgcgatgcat tagctagttg gtaaggtaac ggcttaccaa     240
ggcgatgatg catagccgag ttgagagact gatcggccac attgggactg agacacggcc     300
caaactccta cgggaggcag cagtagggaa tcttccacaa tggacgaaag tctgatggag     360
caacgccgcg tgagtgaaga aggttttcgg atcgtaaagc tctgttgttg gtgaagaagg     420
atagaggtag taactggcct ttatttgacg gtaatcaacc agaaagtcac ggctaactac     480
gtgccagcag                                                           490
```

<210> SEQ ID NO 44

<211> LENGTH: 473
<212> TYPE: DNA
<213> ORGANISM: Lactobacillus jensenii

<400> SEQUENCE: 44

| | | | | | |
|---|---|---|---|---|---|
| cgtcaataaa | ggccagttac | tacctctatc | cttcttcacc | aacaacagag | ctttacgatc | 60 |
| cgaaaacctt | cttcactcac | gcggcgttgc | tccatcagac | tttcgtccat | tgtggaagat | 120 |
| tccctactgc | tgcctcccgt | aggagtttgg | gccgtgtctc | agtcccaatg | tggccgatca | 180 |
| gtctctcaac | tcggctatgc | atcatcgcct | tggtaagccg | ttaccttacc | aactagctaa | 240 |
| tgcatcgcag | gtccatcctt | tagcgacagc | ttacgccgcc | ttttaaactt | ctttcatgcg | 300 |
| aaagtagctt | ttatccggta | ttagcatctg | tttccaaatg | gtatcccaga | cttaagggca | 360 |
| ggttacccac | gcgttactca | cccatccgcc | gctagcttgt | atctatgtcc | attccgaaga | 420 |
| atttctatag | gcaagctcgc | tcgacttgca | tgtattaggc | acgccgccag | cgt | 473 |

<210> SEQ ID NO 45
<211> LENGTH: 482
<212> TYPE: DNA
<213> ORGANISM: Lactobacillus gasseri

<400> SEQUENCE: 45

| | | | | | |
|---|---|---|---|---|---|
| gagcttgcct | agatgaattt | ggtgcttgca | ccaaatgaaa | ctagatacaa | gcgagcggcg | 60 |
| gacgggtgag | taacacgtgg | gtaacctgcc | caagagactg | ggataacacc | tggaaacaga | 120 |
| tgctaatacc | ggataacaac | actagacgca | tgtctagagt | ttaaaagatg | gttctgctat | 180 |
| cactcttgga | tggacctgcg | gtgcattagc | tagttggtaa | ggtaacggct | taccaaggca | 240 |
| atgatgcata | gccgagttga | gagactgatc | ggccacattg | ggactgagac | acggcccaaa | 300 |
| ctcctacggg | aggcagcagt | agggaatctt | ccacaatgga | cgcaagtctg | atggagcaac | 360 |
| gccgcgtgag | tgaagaaggg | tttcggctcg | taaagctctg | ttggtagtga | agaaagatag | 420 |
| aggtagtaac | tggcctttat | ttgacggtaa | ttacttagaa | ggtcacggct | aactacgtgc | 480 |
| ca | | | | | | 482 |

<210> SEQ ID NO 46
<211> LENGTH: 477
<212> TYPE: DNA
<213> ORGANISM: Lactobacillus gasseri
<220> FEATURE:
<221> NAME/KEY: modified_base
<222> LOCATION: (7)..(7)
<223> OTHER INFORMATION: a, c, t, g, unknown or other

<400> SEQUENCE: 46

| | | | | | |
|---|---|---|---|---|---|
| accgtcnata | aaggccagtt | actacctcta | tctttcttca | ctaccaacag | agctttacga | 60 |
| gccgaaaccc | ttcttcactc | acgcggcgtt | gctccatcag | acttgcgtcc | attgtggaag | 120 |
| attccctact | gctgcctccc | gtaggagttt | gggccgtgtc | tcagtcccaa | tgtggccgat | 180 |
| cagtctctca | actcggctat | gcatcattgc | cttggtaagc | cgttaccta | ccaactagct | 240 |
| aatgcaccgc | aggtccatcc | aagagtgata | gcagaaccat | cttttaaact | ctagacatgc | 300 |
| gtctagtgtt | gttatccggt | attagcatct | gtttccaggt | gttatcccag | tctcttgggc | 360 |
| aggttaccca | cgtgttactc | acccgtccgc | cgctcgcttg | tatctagttt | catttggtgc | 420 |
| aagcaccaaa | ttcatctagg | caagctcgct | cgacttgcat | gtattaggca | cgccgcc | 477 |

<210> SEQ ID NO 47
<211> LENGTH: 499

```
<212> TYPE: DNA
<213> ORGANISM: Lactobacillus gasseri

<400> SEQUENCE: 47
tgcagtcgag cgagcttgcc tagatgaatt tggtgcttgc accaaatgaa actagataca      60
agcgagcggc ggacgggtga gtaacacgtg ggtaacctgc ccaagagact gggataacac     120
ctggaaacag atgctaatac cggataacaa cactagacgc atgtctagag tttaaaagat     180
ggttctgcta tcactcttgg atggacctgc ggtgcattag ctagttggta aggcaacggc     240
ttaccaaggc aatgatgcat agccgagttg agagactgat cggccacatt gggactgaga     300
cacggcccaa actcctacgg gaggcagcag tagggaatct tccacaatgg acgcaagtct     360
gatggagcaa cgccgcgtga gtgaagaagg gtttcggctc gtaaagctct gttggtagtg     420
aagaaagata gaggtagtaa ctggccttta tttgacggta attacttaga aagtcacggc     480
taactacgtg ccagcagcc                                                  499

<210> SEQ ID NO 48
<211> LENGTH: 480
<212> TYPE: DNA
<213> ORGANISM: Lactobacillus gasseri

<400> SEQUENCE: 48
tattaccgtc aataaggcca gttactacct ctatctttct tcactaccaa cagagcttta      60
cgagccgaaa cccttcttca ctcacgcggc gttgctccat cagacttgcg tccattgtgg     120
aagattccct actgctgcct cccgtaggag tttgggccgt gtctcagtcc caatgtggcc     180
gatcagtctc tcaactcggc tatgcatcat tgccttggta agccgttgcc ttaccaacta     240
gctaatgcac cgcaggtcca tccaagagtg atagcagaac catcttttaa actctagaca     300
tgcgtctagt gttgttatcc ggtattagca tctgtttcca ggtgttatcc cagtctcttg     360
ggcaggttac ccacgtgtta ctcacccgtc cgccgctcgc ttgtatctag tttcatttgg     420
tgcaagcacc aaattcatct aggcaagctc gctcgacttg catgtattag gcacgccgcc     480

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agagtttgat cmtggctcag                                                  20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cggttacctt gttacgactt                                                  20

<210> SEQ ID NO 51
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 51
cgcggctgct ggcac                                                    15
```

MEDICINAL VAGINAL *LACTOBACILLUS* COCKTAIL

CROSS-REFERENCE TO RELATED APPLICATION

This Application is a Continuation Application of U.S. application Ser. No. 16/307,857 filed Dec. 6, 2018, which is a 35 U.S.C. § 371 National Phase Entry Application of International Application No. PCT/US2017/041558 filed Jul. 11, 2017, which designates the U.S. and claims benefit under 35 U.S.C. § 119(e) of the U.S. Provisional Application No. 62/360,535 filed Jul. 11, 2016, the contents of which are incorporated herein by reference in their entireties.

GOVERNMENT SUPPORT

This invention was made with Government support under Grant Nos. R33 AI094508 awarded by the National Institutes of Health. The Government has certain rights in the invention.

FIELD OF THE INVENTION

The field of the invention relates to the establishment or promotion of a healthy flora.

SEQUENCE LISTING

The instant application contains a Sequence Listing which has been submitted electronically in ASCII format and is hereby incorporated by reference in its entirety. Said ASCII copy, created on Dec. 6, 2018, is named 043214-089901-PCT_SL.txt and is 39,330 bytes in size.

BACKGROUND

An overwhelming body of epidemiologic evidence demonstrates that the resident vaginal bacteria are tightly interwoven into the fabric of innate immunity in the female genital tract, with major consequences for women's and infants' health. It is well supported by culture-based and genomic-based studies that Lactobacilli are the resident vaginotropic bacteria dominating the healthy vaginal microbiome. The state of bacteriome disturbance (vaginal dysbiosis) can lead to vaginitis, bacterial translocation or bacterial vaginosis (BV), which is the most common morbid microbiological syndrome among women of childbearing age, characterized by a shift from a *Lactobacillus*-dominated bacteriome to more diverse polymicrobial states with abundant *Prevotella, Atopobium, Gardnerella* and other less characterized anaerobes (Onderdonk et al., 2016). BV is associated with adverse pregnancy outcome, e.g. preterm birth, sexually transmitted infections and higher risk of HIV acquisition, cervicovaginal viral shedding and transmission (Onderdonk et al., 2016, Buve et al., 2014). Antibiotic treatment is often ineffective to cure and prevent frequent relapses of BV, and even capable of worsening reproductive outcome.

SUMMARY

The compositions and methods described herein are based, in part, on the discovery that a bacterial mixture comprising viable *Lactobacillus* species results in synergistic effects that are effective in treating and/or preventing BV and promoting a healthy vaginal flora. The species that result in this synergistic effect include *Lactobacillus* species, *Lactobacillus* crispatus (*L. crispatus*), *Lactobacillus* gasseri (*L. gasseri*), and *Lactobacillus* jensenii (*L. jensenii*). The selected species are isolated from human subjects and are not proinflammatory. It was also discovered in the course of this work that the proportions of *Lactobacillus* species in the bacterial mixture used to treat and/or prevent BV are important for the efficacy of the treatment.

In one aspect, provided herein is a cocktail comprising *Lactobacillus* species including *L. crispatus, L. jensenii* and *L. gasseri*. In some embodiments, the only *Lactobacillus* species in the cocktail are *L. crispatus, L. jensenii* and *L. gasseri*. In some embodiments, the *L. crispatus* strain in the composition is 223310. In some embodiments, the *L. jensenii* strain in the composition is 2054210. In some embodiments, the *L. gasseri* strain in the composition is 29313. In some embodiments, the Lactobacilli in the composition are *L. crispatus* strain 223310, *L. jensenii* strain 2054210, and *L. gasseri* strain 29313.

In some embodiments, *L. crispatus* comprises 50-73.3% of the bacterial mixture, *L. jensenii* comprises 6.67-33.4% of the bacterial mixture, and *L. gasseri* comprises 16.7-33.4% of the bacterial mixture.

In some embodiments, the bacterial mixture is comprised of 66.7% *L. crispatus*, 16.7% *L. jensenii*, and 16.7% *L. gasseri*.

In some embodiments, the bacterial mixture is comprised of 50% *L. crispatus*, 33.4% *L. jensenii*, and 16.7% *L. gasseri*.

In some embodiments, the bacterial mixture is comprised of 50% *L. crispatus*, 16.7% *L. jensenii*, and 33.4% *L. gasseri*.

In one embodiment, the bacterial mixture further comprises an agent that promotes bacterial growth. Non-limiting example of an agent that promotes bacterial growth include boric acid, a prebiotic, lactic acid, ascorbic acid or another low pH buffering agent.

In one embodiment, the bacterial mixture further comprises an anti-microbial agent or preparation. Non-limiting examples of an anti-microbial agent or preparation include recombinant proteins e.g. human soluble serine leukocyte protease inhibitor (SLPI), which is significantly reduced by BV bacteria and *Trichomonas vaginalis* and deficient in the vaginal secretions of women with BV and trichomoniasis (Huppert et al., 2013), synthetic small molecules e.g. purine analogs e.g. 9-(2-deoxy-2-fluoro-β-Darabinofuranosyl) adenine.

In one embodiment, the bacterial mixture further comprises an antibiotic. In another embodiment, the bacterial mixture further comprises an antibiotic against sexually transmitted and reproductive tract infections including but not limited to bacterial vaginosis, *Chlamydia*, *Candida* and *Trichomonas vaginalis*.

In one embodiment, the antibiotic is metronidazole. In another one embodiment, the antibiotic is clindamycin.

In some embodiments, the bacterial mixture does not elicit an inflammatory response in the subject receiving the treatment.

In some embodiments, the bacterial mixture does not comprise *Lactobacillus rhamnosus*.

In one embodiment, the bacterial mixture is formulated for vaginal delivery.

In another embodiment, the bacteria are in a dried form.

In another embodiment, the bacteria mixture further comprises one or more protective excipients. Non-limiting examples of a protective excipient includes a nonreducing monosaccharide, sugar alcohol, oligosaccharide, amino acid, polyvinylpyrrolodone, polyethylene glycol, branched hydrophilic polysaccharide, inulin, albumin, gelatin, whey proteins, and a polaxomer.

In one embodiment, the bacteria mixture is in a glassy matrix.

In one embodiment, the bacterial mixture is stable at room temperature for at least one year.

Another aspect of the invention relates to the method for treating vaginal dysbiosis by administering the bacterial mixture disclosed herein by administering the mixture to a subject having, or at risk of having, a vaginal bacterial infection.

In one embodiment, the vaginal infection is caused by the vaginal pathogen *Trichomonas vaginalis*.

In one embodiment, the vaginal bacterial infection is caused by the vaginal pathogen *Gardnerella vaginalis*.

In one embodiment, the vaginal bacterial infection is caused by the vaginal pathogen *Prevotella bivia*.

In one embodiment, the vaginal bacterial infection is caused by the vaginal pathogen *Atopobium vaginae*.

In one embodiment the subject is not pregnant. In another embodiment, the subject is pregnant.

In one embodiment the bacterial mixture is delivered to a subject vaginally.

In another embodiment, the bacterial mixture is delivered to a subject as vulvo-vestibular cream.

In another embodiment, the bacterial mixture is delivered to a subject orally.

In another embodiment, the bacterial mixture is delivered to a subject rectally.

In one embodiment, the bacterial mixture restores a healthy vaginal flora.

Another aspect described herein relates to a method of isolating a bacterial strain useful in the treatment of a vaginal bacterial infection. The method comprises (i) isolating bacteria from the vagina of a healthy woman; (ii) isolating *Lactobacillus* species from the bacteria isolated in step (i) via phenotypic and genetic analysis; (iii) verifying stable colonization of *Lactobacillus* species isolated in step (ii) in human vaginal epithelium; (iv) verifying that isolated *Lactobacillus* species isolated in step (ii) do not elicit an immune response (v) verifying minimal mutual antagonism with isolated *Lactobacillus* species isolated in step (ii); and (vi) verifying colonization of *Lactobacillus* species isolated in step (ii) in human vaginal epithelium in the presence of a vaginal pathogen; (viii) generating synergistic formulas comprising of select organisms that past selection criteria in all of the above steps.

In one embodiment, the method further comprises assessing in vitro antimicrobial properties of isolated *Lactobacillus* species.

In one embodiment, the bacteria are isolated from a healthy pregnant woman. In another embodiment, the healthy pregnant woman gives birth at 38-40 weeks of gestation.

Definitions

As referred to herein, the term "healthy human vaginal microbiota balance" refers to the population of different microbial species colonizing or inhabiting the human vagina or vaginal epithelium that together provide an environment that discourages the growth of pathogenic microbes and is not proinflammatory. A healthy human vaginal microbiota balance includes a variety of microbial species in which the relative numbers of each species are in homeostasis. In one embodiment, homeostasis, when used in this context, means that the relative abundance of each species in a population remains generally static, e.g. detectable in the same quartile of multiple logarithmically transformed counts taken over a period of time (for example over several menstrual cycles in a reproductive age women or over a pregnancy trimester), relative to other species in the population. Among healthy reproductive age women the frequency of detection of *Lactobacillus* species across a menstrual cycle varied by less than 2SD (<3%) and the colony forming counts varied also by less than 2SD (~one $\log_{10}$ CFU per gram) (Onderdonk et al., 1987). In one embodiment, "homeostatic", when used in this context, refers to resistant to perturbations caused by vaginal pathogens, e.g. persistence of the colony forming units of healthy bacteria associated with the vaginal epithelium at the time of or after infection by vaginal pathogens.

The healthy human vaginal microbiota is dominated by specific homeostatic *Lactobacillus* species (can be about 95%) *L. crispatus, L. gasseri* and *L. jensenii*, which play an essential role in maintaining an environment that discourages urogenital infection. Species of Lactobacilli adapted to the healthy vaginal environment (but not all *Lactobacillus* species) have the ability to adhere to vaginal epithelia, to inhibit the adhesion and growth of pathogens and to deplete nutrients that otherwise permit the growth of pathogens. Such species also modulate the host's immune response, generally maintaining or promoting a non-proinflammatory status. A critical function of vaginal Lactobacilli is to metabolize glycogen produced by vaginal epithelial cells to produce lactic acid. In a healthy vagina, pH-values of 4.0-4.5 are reached; at this pH, many pathogens cannot flourish. The production of $H_2O_2$ is another feature distinguishing mostly beneficial from mostly non-beneficial *Lactobacillus* species and essential for anti-viral properties such as anti-HIV activity of vaginal lactobacilli (Klebanoff and Coombs, 1991). $H_2O_2$ producing lactobacilli are present in the vagina of most normal healthy women, but they are absent from most women with BV (Klebanoff and Coombs, 1991). Therefore we included $H_2O_2$ production in our *Lactobacillus* strain selection algorithm.

By contrast, a "dysbiotic" human vaginal microbiota balance refers to a population of vaginal microbes that promotes inflammation of a tissue of the vagina and/or that contributes to or establishes an environment that permits or promotes the colonization or growth of one or more pathogenic microbes. A dysbiotic vaginal microbiota will generally result in increased pH relative to a healthy microbiota, e.g., a pH above 5.0, e.g, a pH of 5.5, 5.7, 6.0, 6.2, 6.5, 6.7, 7.0 or higher. In one embodiment, "dysbiosis" when used in this context, refers to a perturbation of the vaginal homeostasis where *Lactobacillus* species colony forming units are displaced from the vaginal epithelium or reduced after infection by vaginal pathogens compared to colony forming units enumerated before infection.

The term "probiotic" as used herein refers to "live microorganisms, which when administered in adequate amounts confer a health benefit on a host" (FAO 2001: see the website at isapp.net/docs/ProbioticDefinition.pdf).

As used herein, the term "proinflammatory" refers to a status in which expression or accumulation of one or more markers or mediators of inflammation, e.g., inflammatory chemokines e.g., IL-8, MIP-1α, MIP-2α, MIP-1β, or inflammatory cytokines, e.g., TNF-α, IL-1 and/or IL-6, are induced in host tissue (Fichorova, 2004, Doncel et al., 2004, Fichorova et al., 2004). A proinflammatory status is also evidenced by the accumulation of inflammatory cells such as polynuclear neutrophils (PNN) and/or eosinophils, among others, in host tissues (Doncel et al., 2004, Fichorova et al., 2004).

As used herein, the term "full term pregnancy," for humans, refers to a pregnancy in which delivery of a healthy infant occurs at 38-40 weeks of gestation. The American College of Obstetricians and Gynecologists applies the following definitions as of 2013: 1) Early Term is between 37 weeks and 38 weeks 6 days; 2) Full Term, between 39 weeks and 40 weeks 6 days; 3) Late Term, the 41st week; 4) Post Term, after 42 weeks.

As used herein, the term "stable colonization" refers to the colonization of an environment, e.g., the vagina or vaginal epithelium, by a microbe, e.g., a bacterium, such that the viable population of that microbe continues over time. A stably colonizing population will generally remain substantially static once colonization is complete, e.g. logarithmically transformed colony forming units associated with the vaginal epithelial tissue will remain in the same quartile after the initial period of colonization (complete in 4 h at the cellular level) when followed within the lifespan of the vaginal epithelial cells (24-48 h).

As used herein, the term "does not elicit an immune response," and equivalent terms "does not induce an immune response" and "does not promote an immune response" or similar variations thereof mean that a given microbial species, e.g., a bacterial species, does not substantially induce inflammatory response by the host immune system. A microbe that does not induce an immune response will not, when administered to human vaginal cells, the vagina of a human or a test animal, promote an expression or accumulation of inflammatory chemokines or cytokines, to significantly increase levels above those of a the healthy unperturbed baseline or the recruitment or accumulation of inflammatory host cells.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "statistically significant" or "significantly" refer to statistical significance and generally means a two standard deviation (2SD) or greater difference.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox or wolf. In some embodiments, the subject is a mammal, e.g., a primate, e.g., a human. The terms, "individual," "patient" and "subject" are used interchangeably herein. Mammals other than humans can be advantageously used as subjects that provide animal models of the vaginal environment. A subject as the term is used herein is generally female.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder, for example vaginal infection, e.g., bacterial vaginosis or fungal vaginitis. Treatment is generally "effective" if one or more symptoms or clinical markers are reduced. Alternatively, treatment is "effective" if the progression of a disease is reduced or halted. That is, "treatment" includes not just the improvement of symptoms or markers, but can also include a cessation or at least slowing of progress or worsening of symptoms that would be expected in absence of treatment. Beneficial or desired clinical results include, but are not limited to, alleviation of one or more symptom(s) of a disease or disorder, diminishment of extent of a disease or disorder, stabilized (i.e., not worsening) state of a disease or disorder, delay or slowing of progression of a disease or disorder, amelioration or palliation of the disease or disorder state, and remission (whether partial or total), whether detectable or undetectable. The term "treatment" of a disease or disorder also includes providing relief from the symptoms or side-effects of the disease (including palliative treatment). Treatment for an infection can, but does not necessarily, include 100% eradication of the pathogen—a treatment that reduces the level of a pathogen to one which is kept in check by the immune system or by the state established by a healthy vaginal micorbiota is considered effective as the term is used herein.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, film, ointment and/or vaginal device e.g. vaginal ring. In some embodiments of any of the aspects, a pharmaceutically acceptable carrier can be an artificial or engineered carrier, e.g., a carrier that the active ingredient would not be found to occur in nature.

The phrase "pharmaceutically acceptable carrier" as used herein means a pharmaceutically acceptable material, composition or vehicle, such as a liquid or solid filler, diluent, excipient, solvent or encapsulating material that maintains a drug or other agent in a form for delivery to a subject. Each carrier must be "acceptable" in the sense of being compatible with the other ingredients of the formulation, for example the carrier does not decrease the impact of an active ingredient or agent upon the treatment. In other words, a carrier is pharmaceutically inert. The terms "physiologically tolerable carriers" and "biocompatible delivery vehicles" are used interchangeably.

The terms "administered" and "subjected" are used interchangeably in the context of treatment of a disease or disorder. Both terms refer to a subject being treated with an effective dose of pharmaceutical composition comprising a composition as described herein by methods that deliver the composition, e.g., a probiotic cocktail, to the vagina.

The term "optional" or "optionally" means that the subsequent described event, circumstance or substituent may or may not occur, and that the description includes instances where the event or circumstance occurs and instances where it does not.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention.

BRIEF DESCRIPTION OF THE DRAWINGS

FIG. 1 shows that the manisfestation of the indicated diseases increases with the number of elevated inflammatory proteins present in the infant at birth (odd ratios >1).

FIG. 4 shows the presence of inflammation mediators found to be increased in the systemic circulation of infants born to mothers with the indicate microorganism present in the placenta.

(FIG. 7A) Next generation sequencing data show the most abundant bacteria clustered in 4 cervicovaginal community types (CT) (FIG. 7B) Comparing a NextGen-derived community state type dominated by *L. crispatus* (CT1) to that dominated by *L. iners* (CT2) and to that of BV-dominant bacteria e.g. *A. vaginae* and *G. vaginalis* (CT3) or *A. vaginae, G. vaginalis* and *P. bivia* (CT4) clearly showed that in African women just as in Caucasian women (FIG. 6) (see e.g. Kyongo J K, Jespers V, Goovaerts O, et al. PloS one. 2012) *L. crispatus* is superior to *L. iners* since CT2 was associated with a tendency of higher levels of inflammatory cytokines compared to CT1, and similar to CT3 and CT4.

FIGS. 8A-8E shows inflammatory proteins from groups in FIG. 7B. The level of (FIG. 8A) IL-1α, (FIG. 8B) IL-1β, (FIG. 8C) TNF-α, (FIG. 8D) INF-γ, and (FIG. 8E) IL-12p70 were measured.

(FIGS. 9A-9D) Transmission electron microscopy image showing *L. crispatus* (FIGS. 9A and 9B) and *P. bivia* (FIGS. 9C and 9D) bacteria, visualized as electron-dense bodies, adherent to the surface of vaginal epithelial cells (Vk2/E6E7A) which exhibit intact morphology after 24 h of colonization. The bars and images represent 500 nm and ×4,800 magnification (FIG. 9A), 500 nm and ×6,800 magnification (FIG. 9B), 2 μm and ×1,900 magnification (FIG. 9C), and 500 nm and ×13,000 magnification (FIG. 9D), respectively. (FIG. 9E) Caspase-3 cleavage is presented as percentages of cleaved from total caspase-3 measured in vaginal epithelial cell lysates at 24 h after bacterial colonization or treatment with 1 μM staurosporine, Bars represent means and standard errors of the means (SEM) of the results determined with duplicate cultures used in two experiments. (FIG. 9F) Viability of vaginal epithelial cells assessed by trypan blue inclusion tests at 5 days postcolonization. Bars represent manes and SEM of the results from triplicate culture experiments. (FIG. 9G) CFU counts per square centimeter of epithelial cell surface at 24 h and 48 h postcolonization of Vk2/E6E7 cells. Bars represent means and SEM of the results determined with triplicate cultures used in three experiments. (FIG. 9H) Parallel assessment of CFU counts associated with primary polarized (VEC-100) and immortalized monolayer (Ect1/E6E7) ectocervical epithelial cells at 48 h postcolonization.

FIGS. 13A-13D. Shows differences between *Lactobacillus* strains indicated by the activity of the indicated inflammation mediator with the indicated strains and activity against *G. vaginalis*. Individual vaginal *Lactobacillus* strains differed in their immune profiles assessed by cytokines and chemokine production by human vaginal and cervical epithelial cells 24 h after bacterial colonization (FIGS. 13A-13C) and also differed by then anti-BV activities assessed by *G. vaginalis* colonization rates (FIG. 131)). Among 5 BWH strains selected based on favorable pregnancy outcome, three representing *L. crispatus* (Lc1), *L. jensenii* (Lj1) and *L. gasseri* (Lg) (bars in black) were further selected based on: 1) their best homeostatic properties e.g. cytokine levels (exemplified by IL-8, FIG. 13C) closest to the epithelial baseline (CTRL); 2) activity against *G. vaginalis* (FIG. 13D). The Lc strains obtained from S. Hiller (Lc4) failed due to highest pro-inflammatory activity compared to the others and the ATCC prototype (Lj3) failed due to lack of anti-*G. vaginalis* activity (FIG. 13B).

(FIG. 22A) numbers of epithelial cell associated *G. vaginalis* CFUs following simultaneous infection with *G. vaginalis* and vaginal lactobacilli alone or in Mix 1 (1:1:1 ratio of Lg:Lc:Lj) (FIG. 22B) Numbers of epithelial cell associated *G. vaginalis* CFU following colonization with the indicated combination of Lg, Lc, Lj, or Mix 1 (1:1:1 ratio of Lg:Lc:Lj), Mix 5 (1:3:2 ratio of Lg:Lc:Lj), Mix 6 (2:3:1 ratio of Lg:Lc:Lj), and Mix 7. (Lc=*L. crispatus* 223310, Lj=*L. jensenii* 2054210, and Lg:=*L. gasseri* 29313).

(FIG. 25A) Stability of PBV bacteria stored over a 2 year period at indicated temperatures. (FIG. 25B) Preservation of epithelial tissue colonization capacity of PBV stored over a 2 year period at indicated temperatures. (FIG. 25C) Vaginal epithelial colonization by individual and mixed PBV bacteria (Lc=*L. crispatus* 223310, LJ=*L. jensenii* 2054210, and Lg=*L. gasseri* 29313) stored over 1 year at ambient RT (>25° C.) after PBV preservation and compared to bacterial stocks stored frozen. Bars are means and SEM from biological duplicates in four experiments.

DETAILED DESCRIPTION

Figure 2:
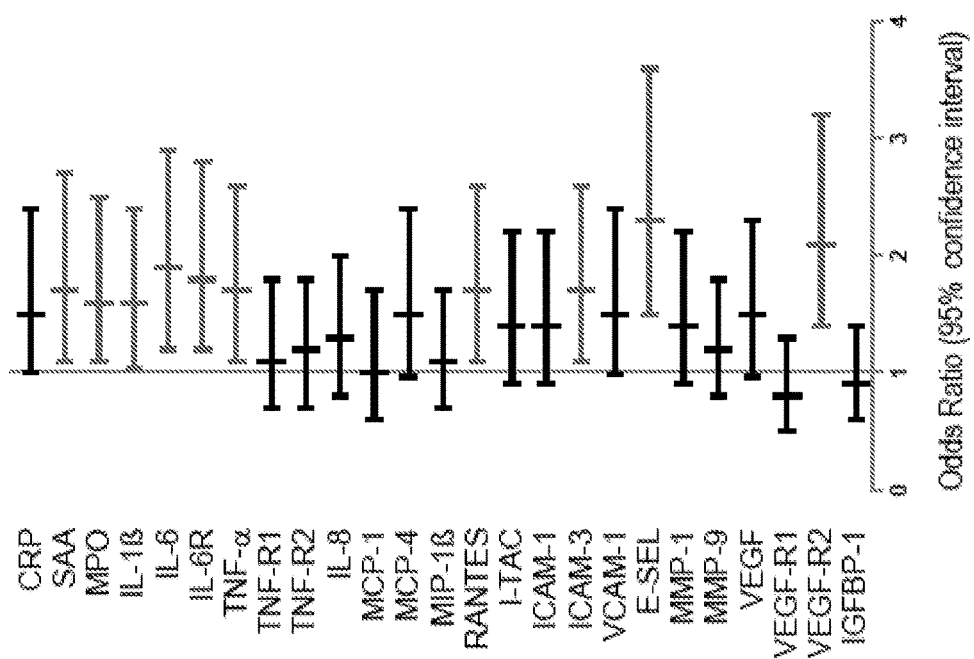
FIG. 2 shows the mediators of inflammation found to be increased (odds ratios >1) in the systemic circulation of infants born to mothers with cervicitis and vaginitis.

The compositions and methods described herein are based, in part, on the discovery that a bacterial mixture comprising a limited number of viable *Lactobacillus* species is effective in treating and preventing vaginal dysbiosis, and promoting a healthy vaginal flora. It was discovered that the combination of *L. crispatus, L. gasseri,* and *L. jensenii* results in a synergistic effect that promotes the growth of the community within the bacterial mixture, as well as the capacity for the bacterial mixture to combat *T. vaginalis* and *B. gardneri* vaginal colonization. This effect was particularly prominent with *L. crispatus* strain 223310, *L. jensenii* strain 2054210, and *L. gasseri* strain 29313. The selected strains are derived from healthy reproductive age women, or healthy pregnant women who went on to give birth after at 38-40 weeks of gestation. In vivo assays established that the selected strains do not elicit a proinflammatory response. It was also found that the proportions of the members of the consortium or cocktail influence the efficacy of the formulation. Described herein are proportions of the *Lactobacillus* species within the bacterial mixture that are particularly effective when using this combination of Lactobacilli to treat vaginal bacterial infection and/or promote a healthy vaginal flora.

Various considerations useful for the practice of the compositions and methods disclosed herein are set out in the following.

Maintaining a Healthy Vaginal Microbiota Balance

While exact species and proportions can vary among healthy women, the healthy resident vaginal microbiome is dominated by Gram positive, non-spore-forming, lactic acid-producing bacteria of the *Lactobacillus* genus. In a healthy woman, *Lactobacillus* species represent upwards of 95% of the resident vaginal bacteria. Among other things, the production of lactic acid as a product of normal *Lactobacillus* metabolism functions to maintain an acidic pH in the vagina (generally pH 3.8-4.5), which provides an environment that discourages the growth of most vaginal pathogens. Species of Lactobacilli adapted to the vaginal environment have the ability to adhere to vaginal epithelia, to inhibit the adhesion and growth of pathogens and to deplete nutrients that otherwise permit the growth of pathogens. Such species also modulate the host's immune response, generally maintaining or promoting a non-proinflammatory status. A large body of epidemiologic evidence demonstrates that the resident vaginal bacteria are intimately involved in innate immunity in the female genital tract, with major consequences for women's and infants' health if disrupted.

Vaginal dysbiosis is a disruption of the balance of *Lactobacillus*-dominated resident vaginal bacteria of the healthy vagina, and involves or permits the establishment, growth or expansion of one or more species of non-*Lactobacillus* species of microbe. Vaginal dysbiosis can be initiated, for example, by iatrogenic interventions, sexual behavior or hormonal change, infections, systemic stress, malnutrition or illness. Vaginal dysbiosis can lead to vaginitis, bacterial translocation or bacterial vaginosis (BV), which is the most common morbid microbiological syndrome among women of childbearing age, characterized by a shift from a *Lactobacillus*-dominated bacteriome to more diverse polymicrobial states with abundant *Prevotella, Atopobium, Gardnerella* and other less characterized anaerobes. BV is associated with adverse pregnancy outcome, e.g. preterm birth, sexually transmitted infections and higher risk of HIV acquisition, cervicovaginal viral shedding and transmission. Antibiotic treatment is often ineffective to cure and prevent the frequent relapses of BV, and even capable of worsening reproductive outcome.

Compositions and methods are described herein for maintaining, establishing and/or restoring a healthy vaginal microbiota balance. The compositions and methods are based, in part, upon the identification of a consortium of three probiotic *Lactobacillus* species that act synergistically to affect a healthy vaginal microbiota balance. More specifically, strains of *L. crispatus, L. jensenii* and *L. gasseri* have been isolated from healthy pregnant human vaginal samples and, together, promote or maintain a healthy human vaginal microbiota balance. Indeed, as demonstrated in the Examples provided herein, the strains identified can not only discourage growth of pathogenic microbes common in bacterial vaginosis or in fungal vaginitis, but can actually treat such conditions. The strains identified grow better in combination than singly, both in vitro and in vivo, meaning that one or more of the species produces or modifies a metabolite that promotes the growth or viability of one or more of the others. In addition, it was also found that not just the presence of the identified strains, but the ratios in which they are introduced relative to each other are important for establishing and maintaining a healthy vaginal microbiota balance. These aspects and others are described further in the following.

*Lactobacillus* Species

By "*Lactobacillus*" is meant any bacteria from the genus *Lactobacillus*, including *L. crispatus, L. jensenii,* and *L. gasseri,* among others. Numerous other species are outlined by Wood et al. (Holzapfel and Wood, eds. (1995) The Genera of Lactic Acid Bacteria, Vol. 2., Springer, N.Y.). Lactobacilli are members of a larger group of lactic acid bacteria, all of which are Gram positive, non-spore-forming cocci, coccobacilli or rods. Lactobacilli have a DNA base composition with less than 50% G+C, do not express catalase and rely upon a fermentable carbohydrate for growth. They are members of the phylum Firmicutes, class Bacilli, order Lactobacillales and family Lactobacillaceae. Species of Lactobacilli can be identified phenotypically, as well as genetically, e.g., on the basis of 16S rRNA sequence (or more often in practice, the DNA encoding the 16S rRNA, generally referred to as 16S rDNA).

*Lactobacillus* species *L. crispatus, L. jensenii* and *L. gasseri* described herein were isolated from healthy pregnant women using a selective approach described herein below. It is noted that where one focus of the work described herein was to identify species that promote or maintain a healthy vaginal microbiota or healthy vaginal microbiota balance in pregnant women, e.g., to reduce risk of pre-term birth or other complications associated with vaginal dysbiosis during pregnancy, the methods and compositions described herein are equally applicable to non-pregnant women and girls.

By focusing on the healthy vaginal microbiome it is much more likely that identified species of microbes will be non-pathogenic, non-proinflammatory and well adapted to the healthy vaginal environment. Apart from being isolated from a healthy woman, e.g., a healthy pregnant or non-pregnant woman, characteristics of *Lactobacillus* species or strains appropriate for the compositions and methods described herein include, for example, stable colonization of human vaginal epithelium in a culture model as described herein in the Examples, and not provoking a local or systemic inflammatory or immune response as evidenced, for example, by assays using gnotobiotic mice and measuring proinflammatory cytokines such as IL-1$\beta$ and TNF-$\alpha$, or the downstream effector chemokine GRO/KC. Additional characteristics include, for example, maintenance of the balance of anti-inflammatory and proinflammatory mediators in vaginal epithelial cells colonized by the species or strain, and not altering the ability of the vaginal epithelium to mount innate responses to pathogenic determinants, e.g., as measured by the ability to respond to synthetic ligands for TLR2/6 (mimetic of bacterial lipoprotein) and TLR3 (mimetic for viral dsRNA).

Appendix A includes additional 16S rRNA gene sequences for the inactive or less active strains of *L. crispatus, L. jensenii*, and *L. gasseri*. Appendix A discloses SEQ ID NOS 49-51 and 7-30 in order as they appear.

Appendix B includes additional 16S rRNA gene sequences of *L. crispatus, L. jensenii*, and *L. gasseri* strains that were less optimal by one or more criteria but showed beneficial clinical phenotype. Appendix B discloses SEQ ID NOS 49-51 and 31-48 in order as they appear.

Appendix C includes phenotypic characteristics of *L. crispatus, L. jensenii*, and *L. gasseri* strains.

In one embodiment, the *Lactobacillus* crispatus strain is 223310 (BWH invention reference #23158; ATCC Deposit PTA-127090, deposited Jul. 9, 2021). The deposit was made at American Tissue Culture Collection (ATCC), having a mailing address of 10801 University Boulevard, Manassas, VA 20110 USA. The 16S rDNA sequence of *L. crispatus* strain 223310 is as follows

*L. crispatus* strain 223310 ATCC PTA-127090 16S rRNA gene sequence generated with 27F forward primer as follows (SEQ ID NO: 1):

TGCAGTCGAGCGAGCGGAACTAACAGATTTACTTCGGTAATGACGTTAGG

AAAGCGAGCGGCGGATGGGTGAGTAACACGTGGGGAACCTGCCCCATAGT

CTGGGATACCACTTGGAAACAGGTGCTAATACCGGATAAGAAAGCAgATC

GCATGATCAGCTTTTAAAAGGCGGCGTAAGCTGTCGCTATGGGATGCCC

CGCGGTGCATTAGCTAGTTGGTAAGGTAAAGGCTTACCAAGGCGATGATG

CATAGCCgAgtTGAGAGACTGATCGGCCACATTGGGACTGAGACACGGCC

CAAACTCCTACGGGAGGCAGCAGTAGGGAATCTTCCACAATGGACGCAAG

TCTGATGGAGCAACGCCGCGTGAGTGAAGAAGGTTTTCGGATCGTAAAGC

TCTGTTGTTGGTGAAGAAGGATAGAGGTAGTAACTGGCCTTTATTTGACG

GTAATCAACCAGAAAGTCACGGCTAACT

*L. crispatus* strain 223310 ATCC PTA-127090 16S rRNA gene sequence generated with 529R reverse primer as follows (SEQ ID NO: 2):

CGTCAATAAAGGCCAGTTACTACCTCTATCCTTCTTCACCAACAACAGAG

CTTTACGATCCGAAAACCTTCTTCACTCACGCGGCGTTGCTCCATCAGAC

TTGCGTCCATTGTGGAAGATTCCCTACTGCTGCCTCCCGTAGGAGTTTGG

GCCGTGTCTCAGTCCCAATGTGGCCGATCAGTCTCTCAACTCGGCTATGC

ATCATCGCCTTGGTAAGCCTTTACCTTACCAACTAGCTAATGCACCGCGG

GGCCATCCCATAGCGACAGCTTACGCCGCCTTTTAAAAGCTGATCATGCG

ATCTGCTTTCTTATCCGGTATTAGCACCTGTTTCCAAGTGGTATCCAGA

CTATGGGGCAGGTTCCCCACGTGTTACTCACCCATCCGCCGCTCGCTTTC

CTAACGTCATTACCGAAGTAAATCTGTTAGTTCCGCTCGCTCGACTTGCA

TGTATTAGGCACGCCGCCAGCGTTC

Strains in addition to *L. crispatus* strain 223310, including *L. crispatus* ATCC 3820, a H$_2$O$_2$ producing strain of *L. crispatus* received from Dr. Sharon Hillier, and Brigham and Women's Hospital (BWH) *L. crispatus* strains 101211 and 24629 were investigated for activity in the assays described herein in the Examples, but found to be inactive or less active in one or more criteria examined than *L. crispatus* strain 223310. Appendix A includes additional 16S rRNA gene sequences for the inactive or less active strains are set out herein. Appendix B includes additional 16S rRNA gene sequences of strains that were less optimal by one or more criteria but showed beneficial clinical phenotype. Appendix C includes phenotypic characteristics of *L. crispatus* strain 223310.

In one embodiment, the *Lactobacillus jensenii* strain is 2054210 (BWH invention reference #23379; ATCC Deposit #PTA-127092, deposited Jul. 9, 2021). The deposit was made at American Tissue Culture Collection (ATCC), having a mailing address of 10801 University Boulevard, Manassas, VA 20110 USA.

The *L. jensenii* strain 2054210 ATCC PTA-127092 16S rRNA gene sequence generated with 27F forward primer is as follows (SEQ ID NO: 3):

TGCAGTCGAGCGAGCTTGCCTATTGAAATTCTTCGGAATGGACATAGATA

CAAGCTAGCGGCGGATGGGTGAGTAACGCGTGGGTAACCTGCCCTTAAGT

CTGGGATACCATTTGGAAACAGATGCTAATACCGGATAAAAGCTACTTTC

GCATGAAAGAAGTTTAAAAGGCGGCGTAAGCTGTCGCTAAAGGATGGACC

TGCGATGCATTAGCTAGTTGGTAAGGTAACGGCTTACCAAGGCGATGATG

CATAGCCGAGTTGAGAGACTGATCGGCCACATTGGGACTGAGACACGGCC

CAAACTCCTACGGGAGGCAGCAGTAGGGAATCTTCCACAATGGACGCAAG

TCTGATGGAGCAACGCCGCGTGAGTGAAGAAGGTTTTCGGATCGTAAAGC

TCTGTTGTTGGTGAAGAAGGATAGAGGTAGTAACTGGCCTTTATTTGACG

GTAATCAACCAGAAAGTCACGGCTAACTACG

The *L. jensenii* strain 2054210 ATCC PTA-127092 16S rRNA gene sequence generated with 529R reverse primer as follows (SEQ ID NO: 4):

CGTCAATAAAGGCCAGTTACTACCTCTATCCTTCTTCACCAACAACAGAG

CTTTACGATCCGAAAACCTTCTTCACTCACGCGGCGTTGCTCCATCAGAC

TTGCGTCCATTGTGGAAGATTCCCTACTGCTGCCTCCCGTAGGAGTTTGG

GCCGTGTCTCAGTCCCAATGTGGCCGATCAGTCTCTCAACTCGGCTATGC

ATCATCGCCTTGGTAAGCCGTTACCTTACCAACTAGCTAATGCATCGCAG

GTCCATCCTTTAGCGACAGCTTACGCCGCCTTTTAAACTTCTTTCATGCG

AAAGTAGCTTTTATCCGGTATTAGCATCTGTTTCCAAATGGTATCCCAGA

CTTAAGGGCAGGTTACCCACGCGTTACTCACCCATCCGCCGCTAGCTTGT

ATCTATGTCCATTCCGAAGAATTTCAATAGGCAAGCTCGCTCGACTTGCA

TGTATTAGGCACGCCGCCAGCGTTC

Strains in addition to *L. jensenii* strain 2054210, including *L. jensenii* ATCC 25258, *L. jensenii* 1153 and several others listed in were investigated for activity in the assays described herein in the Examples, 16S rRNA gene sequences strains are set out herein in Appendix A. 16S rRNA gene sequences of strains that were less optimal by one or more criteria but showed beneficial clinical phenotype are included in Appendix B. Phenotypic characteristics of *L. jensenii* strain 2054210 are included in Appendix C.

In one embodiment, the *Lactobacillus* gasseri strain is 29313 (BWH invention reference #23380; ATCC Deposit #PTA-127091, deposited 7/9/2021), also known as *L. acidophilus* 239-13. The deposit was made at American Tissue Culture Collection (ATCC), having a mailing address of 10801 University Boulevard, Manassas, VA 20110 USA.

The *L. gasseri* strain 29313 ATCC PTA-127091 16S rRNA gene sequence generated with 27F forward primer as follows (SEQ ID NO: 5):

```
TGCAGTCGAGCGAGCTTGCCTAGATGAATTTGGTGCTTGCACCAaATGAA

ACTAGATACAAGCGAGCGGCGGACGGGTGAGTAACACGTGGGTAACCTGC

CCAAGAGACTGGGATAACACCTGGAAACAGATGCTAATACCGGATAACAA

CACTAGACGCATGTCTAGAGTTTAAAAGATGGTTCTGCTATCACTCTTGG

ATGGACCTGCGGTGCATTAGCTAGTTGGTAAGGCAACGGCTTACCAAGGC

AATGATGCATAGCCGAGTTGAGAGACTGATCGGCCACATTGGGACTGAGA

CACGGCCCAAACTCCTACGGGAGGCAGCAGTAGGGAATCTTCCACAATGG

ACaCAAGTCTGATGGAGCAACGCCGCGTGAGTGAAGAAGGGTTTCGGCTC

GTAAAGCTCTGTTGGTAGTGAAGAAAGATAGAGGTAGTAACTGGCCTTTA

TTTGACGGTAATTACTTAGAAAGTCACGGCTAACTACGTGCC
```

The *L. gasseri* strain 29313 ATCC PTA-127091 16S rRNA gene sequence generated with 529R reverse primer as follows (SEQ ID NO: 6):

```
TATTACCGTCAATAAAGGCCAGTTACTACCTCTATCTTTCTTCACTACCA

ACAGAGCTTTACGAGCCGAAACCCTTCTTCACTCACGCGGCGTTGCTCCA

TCAGACTTGCGTCCATTGTGGAAGATTCCCTACTGCTGCCTCCCGTAGGA

GTTTGGGCCGTGTCTCAGTCCCAATGTGGCCGATCAGTCTCTCAACTCGG

CTATGCATCATTGCCTTGGTAAGCCGTTGCCTTACCAACTAGCTAATGCA

CCGCAGGTCCATCCAAGAGTGATAGCAGAACCATCTTTTAAACTCTAGAC

ATGCGTCTAGTGTTGTTATCCGGTATTAGCATCTGTTTCCAGGTGTTATC

CCAGTCTCTTGGGCAGGTTACCCACGTGTTACTCACCCGTCCGCCGCTCG

CTTGTATCTAGTTTCATtTGGTGCAAGCACCAAATTCATCTAGGCAAGCT

CGCTCGACTTGCATGTATTAGGCACGCCGCCAGCGTTCG
```

Strains in addition to *L. gasseri* strain 29313, including Brigham and Women's Hospital (BWH) *L. gasseri* strains 117427 and 217213 were investigated for activity in the assays described herein in the Examples, but failed to meet criteria based on clinical phenotype. 16S rRNA gene sequences for these strains are set out herein in Appendix A. 16S rRNA gene sequences of strains that were less optimal by one or more criteria but showed a promising clinical phenotype are included in Appendix B. Phenotypic characteristics of *L. gasseri* 29313 are included in Appendix C.

The above lactic acid bacteria include, for example but not limited to, viable bacteria, wet bacteria, dry viable bacteria (e.g., preparations including viable spray-dried cells, freeze-dried cells, vacuum-dried cells, drum-dried cells, vitrified etc.), and the like. Preparations of *Lactobacillus* species described herein can include, for example, suspensions of *Lactobacillus* bacteria, cultured cells of *Lactobacillus* bacteria (including bacterial cells, supernatant, and medium ingredients), and cultured media containing *Lactobacillus* bacteria (obtained by removing solid contents from the cultured cells of bacteria). While viable *Lactobacillus* bacteria are used in most applications considered herein, it is contemplated that in some embodiments, processed cells of *Lactobacillus* bacteria can include, for example, ground cells, crushed cells, liquefied cells (extracts etc.), concentrates, paste-like cells, dried preparations thereof, and the like.

Vaginal Pathogens

By maintaining a healthy vaginal pH and otherwise affecting the vaginal mucosal and epithelial environment, methods and compositions described herein can provide a vaginal environment that discourages or inhibits the establishment or growth of pathogenic organisms in the female reproductive tract. In this manner, the compositions and methods described herein can provide protection from or treatment for, any of a number of vaginal pathogens. Non-limiting examples of vaginal pathogens known or contemplated to be influenced in this manner include *Chlamydia trachomatis, Candida albicans, Candida galbrata, Candida parapsilosis, Candida tropicalis, Candida kefir, Candida krusei, Candida pseudotropicalis, Candida lusitaniae, Candida rugosa, Trichomonas vaginalis*, and *Gardnerella vaginalis*. Susceptibility to viral infection can also be affected by vaginal dysbiosis, including, but not limited to susceptibility to infection with HIV, HPV and Herpesviruses; it is contemplated that *Lactobacillus* species or strains as described herein can reduce the likelihood or provide a degree of protective effect against these and other viral infections of the female reproductive tract.

Antibiotics

It is contemplated that compositions and methods described herein can be administered in combination with, or in conjunction with, antibiotic treatments aimed at killing or halting the growth of vaginal pathogens. Antibiotic treatments are often indiscriminate in the species they kill, such that the pathogen is killed along with the majority of the probiotic or commensal microbes of the vagina or female reproductive tract. In one embodiment, then, an infection can be treated by administering an antibiotic, and a *Lactobacillus* preparation or cocktail as described herein can be administered following the antibiotic to promote the restoration of a healthy vaginal microbiota or healthy vaginal microbiota balance. In other embodiments, it is contemplated that antibiotic treatment can be administered at the same time as a *Lactobacillus* cocktail as described herein. It is recognized that where a broad spectrum antibiotic is administered, it is likely to kill at least a portion of the Lactobacilli administered; however, at sufficiently high doses of the *Lactobacillus* cocktail, a benefit of co-administration with an antibiotic is contemplated. Alternatively, where an anti-fungal, such as fluconazole is administered to treat, e.g., a *Candida* infection, the antifungal would not be expected to have a strong effect on the Lactobacilli in the cocktails described herein, and either or both of co-administration and post-antifungal administration of a *Lactobacillus* cocktail as described herein may be indicated.

Any antibiotic effective against a vaginal pathogen can be used according to such embodiments. However, non-limiting examples include metronidazole, and other antibiotics from the nitroimidazole class e.g. tinidazole and secnidazole, clindamycin, nystatin, azithromycin, erythromycin, ofloxacin, doxycycline, levofloxacin, amoxicillin, or fluconazole at doses non-inhibiting the *Lactobacillus* vaginal colonization or not bactericidal for the *lactobacillus* strains.

It is additionally contemplated that compositions and methods described herein can be administered in combination with, or in conjunction with, antiseptics aimed at killing or halting the growth of vaginal pathogens. Examples include but are not limited to essential oils from medicinal plants that have strong antiseptic activities such as thymol (a natural monoterpene phenol found in thyme effective against *Gardnerella* biofilms) and eugenol (phenylpropene extracted from clove oil) can be used according to such embodiments. Other antiseptics such as glycerol monolaurate which is compatible with *Lactobacillus* growth and octenidine hydrochloride/phenoxyethanol can also be used according to such embodiments Modified *Lactobacillus* Species It is contemplated that one or more of the *Lactobacillus* species comprising a cocktail as described herein can be modified, e.g., genetically modified to express a beneficial product or a marker or indicator not normally expressed by that species. The beneficial effect can be on the host, or even, for example, on one or more of the other *Lactobacillus* members of the cocktail. Methods for genetically modifying bacteria are known to those of ordinary skill in the art.

In one embodiment, a *Lactobacillus* species member of a cocktail as described herein can be modified to express one or more anti-microbial peptides (AMPs) or bacteriocins, e.g., an AMP or bacteriocin that targets microbial (bacterial, fungal or even viral) species other than Lactobacilli. AMPs have been identified in species ranging from bacteria, amphibians to mammals, including humans. AMPs form a first line of host defense against pathogenic infections and are a key component of the ancient innate immune system. Most antimicrobial peptides comprise 6-50 amino acid residues, and carry a net positive charge. While not wishing to be bound by theory, it is generally thought that such cationic peptides selectively interact with anionic bacterial membranes, although different mechanisms may be used by some AMPs. A large collection of AMPs and their activities are described, for example, in the Antimicrobial Peptide Database (APD)—see, e.g., Wang et al., Nucleic Acids Res. 32 (Database issue): D590-D592 (2004), and Collection of Anti-Microbial Peptides (CAMP$_{R3}$; at www.camp3.bicnirrh.res.in).

Compositions for Establishing or Maintaining a Healthy Vaginal Flora.

One aspect of the technology described herein is a composition comprising a mixture of viable *Lactobacillus* bacteria consisting of *L. crispatus*, *L. gasseri*, and *L. jensenii*, for the treatment and/or prevention of vaginal dysbiosis. In one embodiment of the aspect described herein, the ratio of viable bacteria in the composition is important for its efficacy.

In one aspect of the invention disclosed herein, the composition comprises a mixture of viable bacteria consisting of *L. crispatus* strain 223310, *L. jensenii* strain 2054210, and *L. gasseri* strain 29313.

In one embodiment, *L. crispatus* strain 223310 comprises 50-73.3% of the bacterial mixture, *L. jensenii* strain 2054210 comprises 6.67-33.4% of the bacterial mixture, and *L. gasseri* strain 29313 comprises 16.7-33.4% of the bacterial mixture.

In one embodiment, the bacterial mixture is comprised of 66.7% *L. crispatus*, 16.7% *L. jensenii*, and 16.7% *L. gasseri*.

In one embodiment, the bacterial mixture is comprised of 50% *L. crispatus*, 33.4% *L. jensenii*, and 16.7% *L. gasseri*.

In another embodiment, the bacterial mixture is comprised of 50% *L. crispatus*, 16.7% *L. jensenii*, and 33.4% *L. gasseri*.

In another embodiment, the bacterial mixture is comprised of 73.3% *L. crispatus*, 6.7% *L. jensenii*, and 20% *L. gasseri*.

In one embodiment, the total of *L. crispatus*, *L. jensenii*, and *L. gasseri* in the bacterial mixture is comprised of 66.7% *L. crispatus*, 16.7% *L. jensenii*, and 16.7% *L. gasseri*.

In one embodiment, the total of *L. crispatus*, *L. jensenii*, and Lactob *L. gasseri* in the bacterial mixture is comprised of 50% *L. crispatus*, 33.4% *L. jensenii*, and 16.7% *L. gasseri*.

In one embodiment, the total of *L. crispatus*, *L. jensenii*, and *L. gasseri* in the bacterial mixture is comprised of 50% *L. crispatus*, 16.7% *L. jensenii*, and 33.4% *L. gasseri*.

In another aspect of the invention disclosed herein, the composition comprises a mixture of viable bacteria wherein *L. crispatus* comprises 50-73.3% of the bacterial mixture, *L. jensenii* comprises 6.67-33.4% of the bacterial mixture, and *L. gasseri* comprises 16.7-33.4% of the bacterial mixture.

In one embodiment, the bacterial mixture is comprised of 66.7% *L. crispatus*, 16.7% *L. jensenii*, and 16.7% *L. gasseri*.

In one embodiment, the bacterial mixture is comprised of 50% *L. crispatus*, 33.4% *L. jensenii*, and 16.7% *L. gasseri*.

In another embodiment, the bacterial mixture is comprised of 50% *L. crispatus*, 16.7% *L. jensenii*, and 33.4% *L. gasseri*.

In another embodiment, the bacterial mixture is comprised of 73.3% *L. crispatus*, 6.7% *L. jensenii*, and 20% *L. gasseri*.

In one embodiment, the total of *L. crispatus*, *L. jensenii*, and *L. gasseri* in the bacterial mixture is comprised of 66.7% *L. crispatus*, 16.7% *L. jensenii*, and 16.7% *L. gasseri*.

In one embodiment, the total of *L. crispatus*, *L. jensenii*, and Lactob *L. gasseri* in the bacterial mixture is comprised of 50% *L. crispatus*, 33.4% *L. jensenii*, and 16.7% *L. gasseri*.

In one embodiment, the total of *L. crispatus*, *L. jensenii*, and *L. gasseri* in the bacterial mixture is comprised of 50% *L. crispatus*, 16.7% *L. jensenii*, and 33.4% *L. gasseri*.

In one embodiment, the composition comprises *L. crispatus* strain 223310, *L. jensenii* strain 2054210, and *L. gasseri* strain 29313.

In some embodiments, the combination of *Lactobacillus* species in the composition results in a beneficial synergistic effect that assists *Lactobacillus* survival and competition against vaginal pathogens. For example, *L. crispatus* did not maintain viable colony forming units in the presence of *A. vaginae*, or suppress epithelial colonization by *A. vaginae*. When in combination with *L. gasseri* and *L. jensenii*, *L. crispatus* does maintain viable colony forming units in the presence of *A. vaginae*, and suppressed epithelial colonization by *A. vaginae*. Additionally, *L. jensenii* is thought to promote a more strong suppression of the protozoan parasite, *T. vaginalis*.

In some embodiments, the compositions described herein further comprise one or more agents that promote bacterial growth. Non-limiting examples of agents that promote bacterial growth include boric acid, a prebiotic, and low pH buffering agents as sodium bicarbonate and agents that can act as both acidifying and prebiotics, such as ascorbic acid (vitamin C).

Boric acid is used in vaginal douches to treat bacterial vaginosis due to its high alkalinity, which confers its antimicrobial property. Boric acid, in various forms, is additionally used as an antimicrobial for the treatment of acne, athlete's foot, and for certain ear infections.

Prebiotics promote the growth, survival, and activity of beneficial microorganisms, for example *Bifidobacteria* and

*Lactobacillus*. Prebiotics have been shown to alter the compositions of microorganisms (microflora) in the gut microbiome, and are contemplated for assisting in the maintenance of a healthy vaginal flora, alone or in combination with *Lactobacillus* cocktail compositions described herein. In addition, prebiotics have been shown to increase calcium and magnesium absorption in the gut, increase bone density, enhance the immune system, reduce blood triglyceride levels, and control hormone levels. Prebiotics include any of a number of compositions that are generally not directly digestible by humans, but that are readily digestible by and promote the growth or establishment of probiotic microbes. Topical vaginal application of the prebiotic sucrose is an effective therapeutic in patients with symptomatic BV. Non-limiting examples of other prebiotics include but are not limited to inulin, fructooligosaccharides, galactooligosaccharides, hemicelluloses (e.g., arabinoxylan, xylan, xyloglucan, and glucomannan), chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

The vaginal pH ranges from 3.8 to 4.5 in a healthy subject. This acidic pH promotes the growth of beneficial bacterial (for example *Lactobacillus*) and prevents the overgrowth of vaginal pathogens that cause odor, irritation, and infection. Buffering agents are weak acids or bases that maintain the acidity at a chosen level and prevent a rapid change in acidity. A non-limiting example of a low pH buffering agents are lactic acid and sodium bicarbonate.

In one embodiment, the composition further comprises at least one excipient. Excipients are substances added to an active ingredient for the purpose of long-term stabilization, bulking up solid formulations that contain active ingredients (known as "bulking agents"), or to enhance or protect the therapeutic benefit of an active ingredient by facilitating drug absorption, reducing viscosity, or increasing solubility or reconstitution from a dry state. Non-limiting examples of protective excipients include a nonreducing monosaccharide, sugar alcohol, oligosaccharide, amino acid, polyvinylpyrrolodone, polyethylene glycol, branched hydrophilic polysaccharide (Ficol™), inulin, albumin, gelatin, whey proteins, and/or a polaxomer. In some embodiments, the composition further comprises at least one, at least two, at least three, at least four, or at least five or more protective excipients.

In one embodiment, the bacteria comprised by the composition are lyophilized, or freeze-dried in a manner that preserves bacterial viability. Methods of preserving viable bacteria by lyophilization can promote long-term preservation of the microorganism. One skilled in the art will be able to lyophilize bacteria using standard techniques. Briefly, microbes are cultured and suspended in lyophilizing buffer or medium. The microbes are rapidly frozen and then subjected to a primary and secondary drying phase to remove all readily available water and residual water, respectively. Storage at 4° C. or lower is recommended, with no moisture present. Standard bacterial lyophilizing techniques can be found in Perry, S. F., *Cryopreservation and freeze-drying protocols*. Volume 38, pg 21-30.

In some embodiments, the composition is formulated for vaginal delivery for treatment and/or prevention of vaginal dysbiosis. Non-limiting examples of vaginal delivery methods include vaginal tablets, capsules, suppositories, creams, and douches. In one embodiment, the composition will be preserved by drying on film, for example preservation by vaporization (PBV).

PBV, as disclosed in U.S. Pat. No. 9,469,835, incorporated herein by reference, allows biological to be stable at higher temperatures for an extended period of time. Using PBV, the composition disclosed herein maintained its viability and capacity to colonize vaginal epithelium up to 2 year at room temperature (approximately 23° C.), and up to 9 months at 37° C. In one embodiment, the composition disclosed herein maintained its viability and capacity to colonize vaginal epithelium at least 2 weeks, at least 3 weeks, at least 1 month, at least 2 months, at least 3 month, at least 4 months, at least 5 month, at least 6 months, at least 7 month, at least 8 months, at least 9 month, at least 10 months, at least 11 month, at least 12 months, at least 13 month, at least 14 months, at least 15 month, at least 16 months, at least 17 months, at least 18 months, at least 19 month, at least 20 months, at least 21 month, at least 22 months, at least 23 month, at least 24 months or longer.

In one embodiment, the bacterial mixture preserved by PBV will comprise 50-73.3% *L. crispatus*, 6.67-33.4% *L. jensenii*, and 16.7-33.4% *L. gasseri*. In one embodiment, the bacterial mixture used preserved by PBV will comprise 66.7% *L. crispatus*, 16.7% *L. jensenii*, and 16.7% *L. gasseri*. In one embodiment, the bacterial mixture preserved by PBV will comprise 50% *L. crispatus*, 33.4% *L. jensenii*, and 16.7% *L. gasseri*. In one embodiment, the bacterial mixture preserved by PBV will comprise 50% *L. crispatus*, 16.7% *L. jensenii*, and 33.4% *L. gasseri*. In one embodiment, the bacterial mixture preserved by PBV will comprise 73.3% *L. crispatus*, 6.7% *L. jensenii*, and 20% *L. gasseri*.

In one embodiment, the composition can be formulated for controlled- or extended-release. Controlled-release pharmaceutical products have a common goal of improving drug therapy over that achieved by their non-controlled release counterparts. Ideally, the use of an optimally designed controlled-release preparation in medical treatment is characterized by a minimum of drug or active substance being employed to cure or control the condition in a minimum amount of time. Advantages of controlled-release formulations include: 1) extended activity of the drug or active substance; 2) reduced dosage frequency; 3) increased patient compliance; 4) usage of less total drug or active substance; 5) reduction in local or systemic side effects; 6) reduction in blood level fluctuations, where appropriate; 7) improvement in efficacy of treatment; 8) reduction of potentiation or loss of drug activity; and 9) improvement in speed of control of diseases or conditions. Kim, Chemg-ju, Controlled Release Dosage Form Design, 2 (Technomic Publishing, Lancaster, Pa.: 2000).

Most controlled-release formulations are designed to initially release an amount of drug or active ingredient that promptly produces the desired therapeutic effect, and gradually and continually release other amounts of drug or active ingredient to maintain this level of therapeutic or prophylactic effect over an extended period of time. In order to maintain this constant level, the drug or active ingredient must be released from the dosage form at a rate that will replace the amount of drug or active ingredient being metabolized or otherwise lost from the body. Controlled-release of an active ingredient can be stimulated by various conditions including, but not limited to, pH, ionic strength, osmotic pressure, temperature, enzymes, water, and other physiological conditions or compounds.

A variety of known extended-release dosage forms, formulations, and devices can be adapted for use with viable bacterial compositions described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In another embodiment, delivery methods and compositions can include encapsulation technology, including, but not limited to a gel composition or gelator. See, e.g., US2011/0229565, US2013-0280334, and US2017/0100342, which describe self-assembling gel compositions that can solidify to encapsulate one or more agents. Each of these references is incorporated herein by reference. Gelators liquefy at a certain pH, releasing the one or more agents they encapsulated.

Methods for Identifying Microbial Strains that Promote Vaginal Health.

One aspect of the invention disclosed herein relates to a method of identifying bacterial strains that are beneficial in treating and/or preventing vaginal dysbiosis. The methods comprise isolating bacteria from the vagina of a healthy woman. Optionally, the healthy woman can be a healthy pregnant woman who will give birth after at 38-40 weeks of gestation (samples can be collected during pregnancy, and patient delivery outcomes followed to correlate those samples taken from patients who carried to full term). One skilled in the art of collecting and culturing bacteria will be able to isolate bacteria from the vagina using standard techniques for isolating the bacteria (for example vaginal swabs).

The methods further comprise isolating and verifying *Lactobacillus* species from the bacteria recovered from the vagina of a healthy woman via phenotypic and genetic analysis. One skilled in the art will be able to phenotypically identify *Lactobacillus* species using standard techniques. For example, one can phenotypically identify *Lactobacillus* species by using a combination of established microbiological techniques including: Vaginal pH, Nugent Score, Whiff Test, API 20E system (BioMerieux, Inc. Durham, NC), API 20 C AUX system (BioMerieux, Inc. Durham, NC), Rapid ANA II system (REMEL Inc., Norcross, GA), Microbial Identification System (Microbial ID Inc., Newark, DE), Gas liquid chromatographic analysis of glucose fermentation products, Total anaerobe concentrations, Total aerobe concentrations, Enzymatic activity (Lipase, phospholipase A2 and phospholipase C, Hydrogen peroxide production. Genetic analysis can be performed using standard techniques, for example genome sequencing analysis. Phylogenetic Investigation of Communities by Reconstruction of Unobserved States (PICRUSt) bioinformatics software can be used to functionally profile a microbial community based on markers, including, but not limited to the 16S ribosomal RNA (or 16S rDNA). This software can be used for genetic analysis of isolated strains.

The method further comprises verifying stable colonization of the isolated and verified *Lactobacillus* species in human vaginal epithelium, verifying that the isolated and verified *Lactobacillus* species do not elicit an immune response, verifying minimal mutual antagonism with the isolated and verified *Lactobacillus*, and verifying colonization of the isolated and verified *Lactobacillus* species in human vaginal epithelium in the presence of a vaginal pathogen.

These methods can be assessed using the in vivo model disclosed in Fichorova, R., et al. 2011. *Mbio*. 2(6), incorporated herein by reference. Briefly, healthy cervicovaginal epithelial cells are grown to confluence, and microorganisms are co-cultured with the confluent cervicovaginal epithelial cells. Colonization of the isolated and verified *Lactobacillus* species is assessed by using transmission electron microscopy (TEM) to observe constant epithelial-associated CFU without inducing cytotoxicity or apoptosis of the epithelial cells. Cytotoxicity and apoptosis of the cervicovaginal epithelial cells can be assessed using standard techniques known to one skilled in the art, for example an MTT assay (Catalog #M6494, Thermo Fisher Scientific, Waltham, MA).

To determine if the isolated and verified *Lactobacillus* species elicit an immune response, the confluent epithelium is collected, lysed, and the cellular supernatant is assessed for mediators of inflammation (e.g., IL-8, IL-$\gamma$, IL-$\beta$, and IL-$\alpha$) using, e.g. western blot analysis or other immunoassay. See for e.g., Fichorova, 2004, Fichorova et al., 2011, Yamamoto et al., 2013).

To determine if there is minimal mutual antagonism, or competition between two or more isolated and verified *Lactobacillus* species, two or more species are co-cultured with cervicovaginal epithelial cells as described above. CFU for each species is assessed using TEM. Minimal mutual antagonism is achieved when at least 90% or more of a given bacterial species survives and proliferates when co-cultured with another bacterial species. In some embodiments, minimal mutual antagonism is evident when at least 95%, 96%, 97%, 98%, 99% or even 100% of a given species survives in the presence of another.

To determine if the isolated and verified *Lactobacillus* species can colonized on cervicovaginal epithelial cells in the presence of vaginal pathogens, the colonization assay described above is used, with the assay further comprising co-culturing the isolated and verified *Lactobacillus* species with a vaginal pathogen. Colonization of the *Lactobacillus* species is assessed as described above.

Dosages Forms and Administration

The dosages of compositions comprising a bacterial mixture that treat and or prevent vaginal dysbiosis can be determined by one of ordinary skill in the art depending on the clinical severity of the disorder (e.g., BV), the age and weight of the patient, and other pharmacokinetic factors generally understood in the art. The interrelationship of dosages for animals of various sizes and species and humans based on $mg/m^3$ of surface area is described by E. J. Freireich et al., "Quantitative Comparison of Toxicity of Anticancer Agents in Mouse, Rat, Hamster, Dog, Monkey and Man," Cancer Chemother. Rep. 50: 219-244 (1966). Adjustments in the dosage regimen can be made to optimize the therapeutic response. Doses can be divided and administered on a daily basis or the dose can be reduced proportionally depending on the therapeutic situation.

In some embodiments, the composition comprising a bacterial mixture for the treatment of vaginal dysbiosis are administered to a subject who has been diagnosed with, or at risk of developing, vaginal dysbiosis or bacterial infection. Microorganisms and/or spores can be separated and selected, using any one of a number of methods that are well known to those of ordinary skill in the art, for their bioactive properties to help ensure and improve the rate pathogen clearance. An effective amount of microorganisms and/or their spores is an amount sufficient to clear pathogens present in the vagina and restore a healthy vaginal flora. In accordance with these embodiments, an effective amount of microorganisms is from 100 thousand to 500 thousand, from 500 thousand to 1 million, from 1 million to 50 million, from 50 million to 100 million, from 100 million to 500 million, from 500 million to 1 billion, from 1 billion to 50 billion, from 50 billion to 100 billion, from 100 billion to 500 billion, from 500 billion to 600 billion CFU per dose, where the dose is administered, for example, daily, one or more times per week, or as often as about one to three times daily.

The dosage range depends upon the potency, and includes amounts large enough to produce the desired effect, e.g., a decrease in pathogens present in the vagina. The dosage should not be so large as to cause unacceptable adverse side effects. Generally, the dosage will vary with the type of agent (e.g., bacteria, an antimicrobial, boric acid, or a low pH buffering agent), and with the age, and condition of the patient. The dosage can be determined by one of skill in the art and can also be adjusted by the individual physician in the event of any complication. Typically, the dosage will range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

The means by which the composition comprising the bacterial mixture described herein should be administered should be appropriate for the given composition. In one embodiment the composition will be administered orally. Microorganisms can be administered in a suspension in liquid form, in a slurry, in a capsule, or, for example, in dried form in a capsule. Methods for maintaining viability of microorganisms throughout the drying process are known to those of skill in the art. Microorganisms, including, but not limited to dried preparations, can also be formulated in enteric-coated or other forms such that when administered orally the microorganisms avoid killing in the harsh acidic conditions of the stomach and are only released to re-hydrate/reactivate in the relatively safer environment of the intestine. Microorganisms can also be administered in admixture with a food or beverage product, including, but not limited to a yogurt, kefir or other dairy product, or as dried microbes in, for example, a bar of cereal, granola, etc. Microorganisms useful in the methods and compositions described herein can also be prepared and/or administered in admixture with one or more prebiotic compositions that promote the maintenance, establishment and/or growth of the probiotic.

In another embodiment, the composition will be administered locally. In one embodiment, the composition is administered vaginally. Microorganisms can be formulated as a cream for topical administration. Microorganisms can be formulated as a vulvo-vestibular cream. Microorganisms can be administered in a suspension in liquid form for use in a douche, in a capsule or vaginal tablet, or, for example, in dried form in a capsule or vaginal tablet. Microorganisms can be dried on film, for example preservation by vaporization (PBV), for vaginal administration in which the microorganisms will re-hydrate/reactivate in the vaginal environment. In one embodiment, the composition is administered rectally.

Therapeutic compositions containing the composition comprising a bacterial mixture for the treatment of vaginal dysbiosis can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

A therapeutically effective amount is an amount of composition comprising a bacterial mixture for the treatment of vaginal dysbiosis sufficient to produce a statistically significant, measurable change in e.g., reversal of damage, etc. (see "Efficacy Measurement" below). Such effective amounts can be gauged in clinical trials as well as animal studies for a given reduction agent.

Efficacy Measurement

The efficacy of a given treatment or prevention of vaginal dysbiosis can be determined by the skilled clinician. However, a treatment is considered "effective treatment," as the term is used herein, if any one or all of the signs or symptoms of, as but one example, vaginal discharge and itching, or other clinically accepted symptoms or markers of disease are improved or ameliorated, e.g., by at least 10% following treatment with a composition comprising a bacterial mixture that treats or prevents vaginal dysbiosis described herein. Efficacy can also be measured by failure of an individual to worsen as assessed by need for medical interventions (e.g., progression of infection is halted or at least slowed). Methods of measuring these indicators are known to those of skill in the art and/or described herein. Example methods include whiff test, wet mount sample to assess the presence of bacteria, and a vaginal pH test. Treatment includes any treatment of a disease in an individual or an animal (some non-limiting examples include a human, or a mammal) and includes: (1) inhibiting the infection, e.g., arresting, or slowing symptoms of the infection, for example vaginal itching and burning; or (2) relieving the infection, e.g., causing regression of symptoms, reducing the symptoms by at least 10%; and (3) restoring healthy vaginal flora, thus preventing future vaginal dysbiosis.

An effective amount for the treatment of vaginal bacterial infection means that amount which, when administered to a mammal in need thereof, is sufficient to result in effective treatment as that term is defined herein, for that disease. Efficacy of the composition can be determined by a physician by assessing physical indicators of vaginal dysbiosis or infection, such as e.g., vaginal discharge and vaginal itching and burning.

The term "effective amount" as used herein refers to the amount of a probiotic or agent that reduces reactive oxygen species described herein needed to alleviate at least one or more symptom of a vaginal infection or dysbiosis, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disorder, alter the course of a symptom (for example but not limited to, slowing the progression of a symptom of the disorder), or reverse a symptom of the disorder. Thus, it is not generally practicable to specify an exact "effective amount." However, for any given case, an appropriate "effective amount" can be determined by one of ordinary skill in the art using only routine experimentation. The term "effective amount" is used interchangeably with the term "therapeutically effective amount" and refers to the amount of at least one agent, e.g., microbe or microbe-containing formulation that treats vaginal dysbiosis or infection, at dosages and for periods of time necessary to achieve the desired therapeutic result, for example, to reduce or stop at least one symptom of such vaginal dysbiosis or infection, in the subject.

Effective amounts, toxicity, and therapeutic efficacy of drug agents, e.g., for formulations or treatments using antibiotics in addition to microbes, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from in vivo assays. Also, a dose can be formulated in animal models to achieve a circulating plasma concentration range that includes the $IC_{50}$ (i.e., the concentration of the active ingredient, which achieves a half-maximal inhibition of symptoms). Levels in plasma can be measured, for example, by high performance liquid chromatography or other appropriate technique. It is contemplated that the relevant level for an agent that reduced reactive oxygen species may also be the level achieved in the lumen of the gut, as opposed to a circulating level. The effects of any particular dosage can be monitored by a suitable bioassay. The dosage can be determined by a physician and adjusted, as necessary, to suit observed effects of the treatment.

Combination Therapies

In one embodiment, the method for treating vaginal dysbiosis described herein further comprises administering standard of care antibiotics for vaginal dysbiosis. Current standard of care antibiotics includes, but are not limited to administering subject who has been diagnosed with a vaginal bacterial infection tinidazole and secnidazole, clindamycin, nystatin, azithromycin, erythromycin, ofloxacin, doxycycline, levofloxacin, or amoxicillin, or an antifungal, fluconazole. Metronidazole is administered orally as a pill, or topically as a gel, clindamycin is administered topically as a cream, and tinidazole is administered orally as a pill. The use combination therapies should be assessed to determine that the standard of care treatment does not interfere or kill the bacterial mixture. Standard antibiotic sensitivity testing, for example a disc test, should be used to assess if the composition and a standard of care therapeutic should be combined. If the antibiotics interfere with the composition, it is contemplated that increasing the amount of composition administered would overcome this interference.

The composition for treatment of vaginal bacterial infection and antibiotics for the same treatment can be combined in the same formulation. Alternatively, the composition and antibiotics can be separate but administered at substantially the same time. The composition and antibiotic can also be administered consecutively, for example the administration of the antibiotic can occur one day after administration of the composition.

In another embodiment, the bacterial mixture further comprises an antiparasitic compounds with activities against *Trichomonas vaginalis* (Adams et al., 2013, Dornbush et al., 2010, Shokar et al., 2012).

It should be understood that antibiotics or other agents that are contraindicated during pregnancy should not be administered to a subject who is pregnant.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Examples

Why Intervention to Correct Vaginal Bacteriome is Needed.

The state of bacteriome disturbance (vaginal dysbiosis) can lead to vaginitis, bacterial translocation or bacterial vaginosis (BV), which is the most common morbid microbiological syndrome among women of childbearing age, characterized by a shift from a *Lactobacillus*-dominated bacteriome to more diverse polymicrobial states with abundant *Prevotella, Atopobium, Gardnerella* and other less characterized anaerobes[1]. Vaginal dysbiosis comprises conditions where the balance between the resident vaginal bacteria dominating the healthy vagina is disturbed by iatrogenic interventions, sexual behavior or hormonal change, infections, systemic stress, malnutrition or illness. Antibiotic treatment vaginal dysbiosis is ineffective, and thus alternative treatments are needed.

The Role of Maternal Microbes in Neonatal Inflammation and Morbidity

Figure 3:
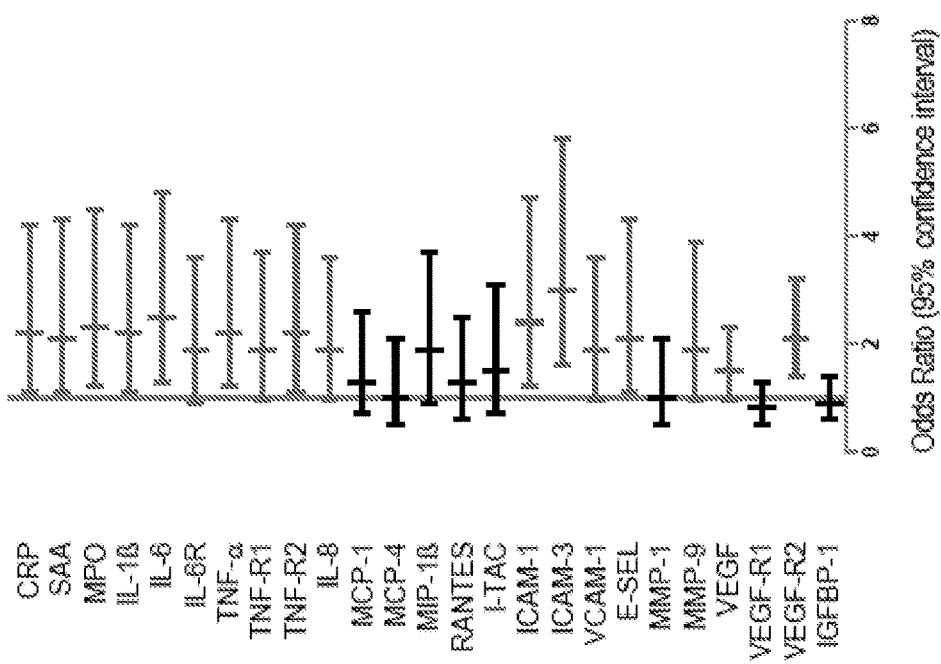
FIG. 3 shows the mediators of inflammation found to be increased (odds ratios >1) in the systemic circulation of infants born to mothers with bacterial vaginosis.

Especially worrisome is the association between BV and preterm birth. Preterm birth occurs in ~10% of all pregnancies (>13% among African Americans), with devastating consequences for newborns, families, and societies[5]. 15 million children are born prematurely every year, and even if all countries with very high development index achieved the best standard of care recorded to date, the world would still experience a reduction of only <5%[6]. In the United States alone, the cost of preterm birth is over $50,000 per infant. While more preterm babies survive due to improved clinical care, the prospects for life quality remain poor for many, due to our lack of therapeutic targeting of fundamental preventable mechanisms of neonatal mortality and morbidity. The perinatal inflammation associated with vaginitis and ascendance of vaginal pathogens to the placenta[7,8] is linked in turn to intrauterine growth retardation[9,10] and brain damage in the preterm born, as well as learning disabilities, attention deficit/hyperactivity, and developmental delay in newborns who survive[11-19] Among the life-long disabilities are cerebral palsy[20,21], asthma[22], schizophrenia[23,24], autism[23], epilepsy[20,25], and low IQ[26]. Research has shown that preterm infants with levels of inflammatory proteins in the top quartile for their age-matched peers population, especially when having 5 or more inflammation proteins increased, have much higher risk of developing ventriculomegaly, cerebral palsy, diparesis, hemiparesis, metal development delay (MDI<50), microcephaly and attention problems[8,11,12,14,27-50] (FIG. 1). As many as 16 or 25 measured mediators of inflammation are increased in the systemic circulation of infants born to mothers with cervicitis and vaginitis[8] (FIG. 2). Maternal microbes ascend in the placenta at high rate and in preterm infants are associated with higher risk of inflammation. In particular BV bacteria ascendance and colonization of the placenta is associated with increased levels of[9] of the inflammatory markers associated with developmental delays and severe neurologic disorders[49] (FIGS. 3 and 4)

Conclusions: Medicinal vaginal probiotics must target cervicovaginal inflammation and ascendance of BV bacteria to the placenta. Ascendance of lactobacilli to the placenta is beneficial.

Choice of *Lactobacillus* Species

Figure 5A:
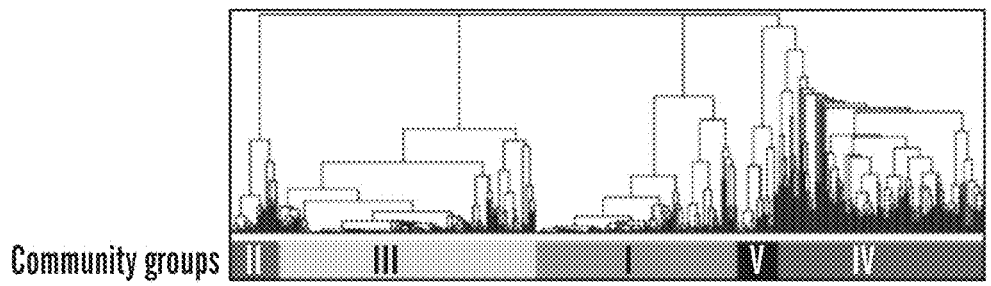
FIGS. 5A and 5B show genomic studies of the vaginal microbiota typically associated with non-BV Nugent score and those typically associated with a BV Nugent score.
Figure 5B:
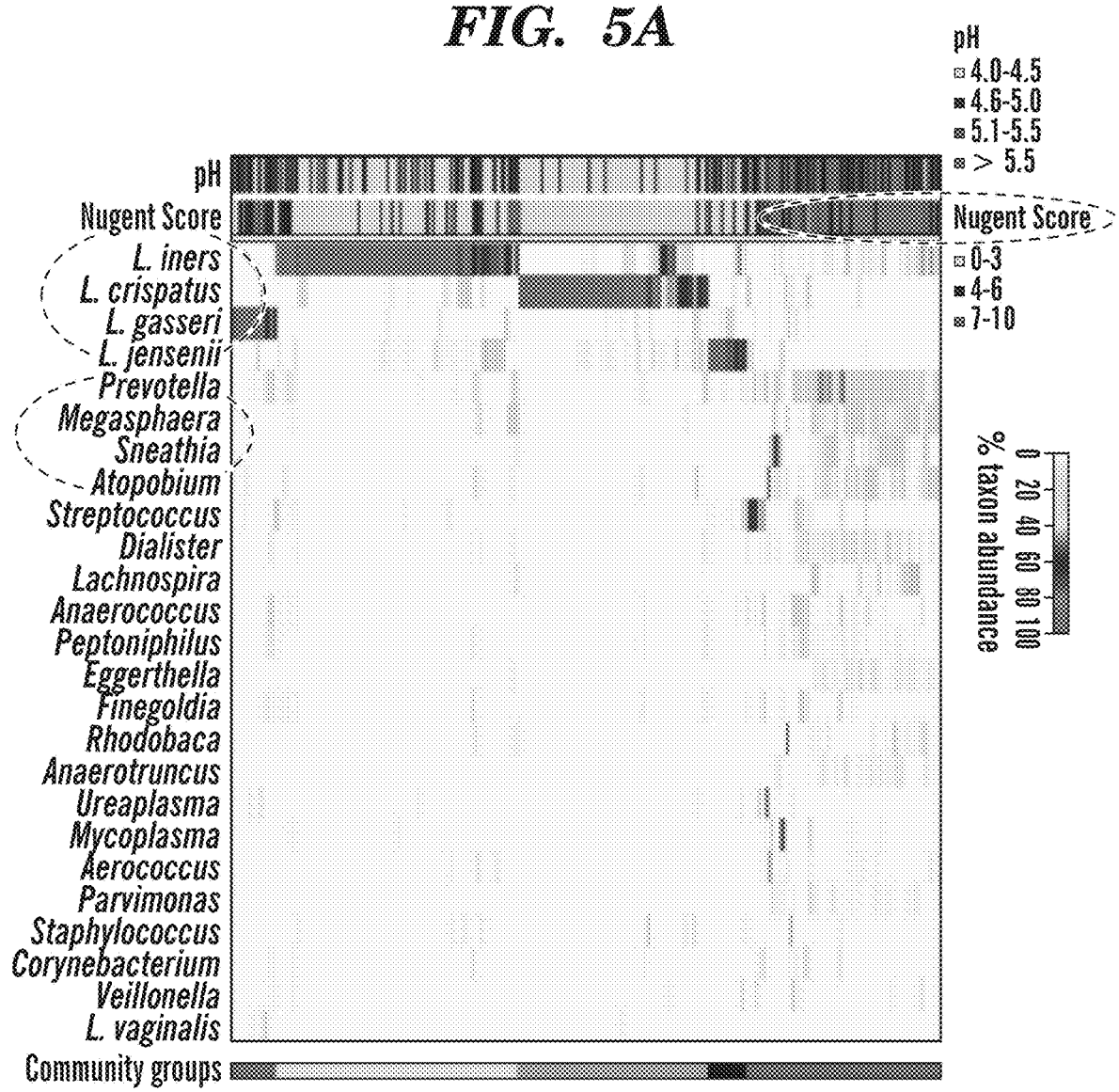
Figure 6:
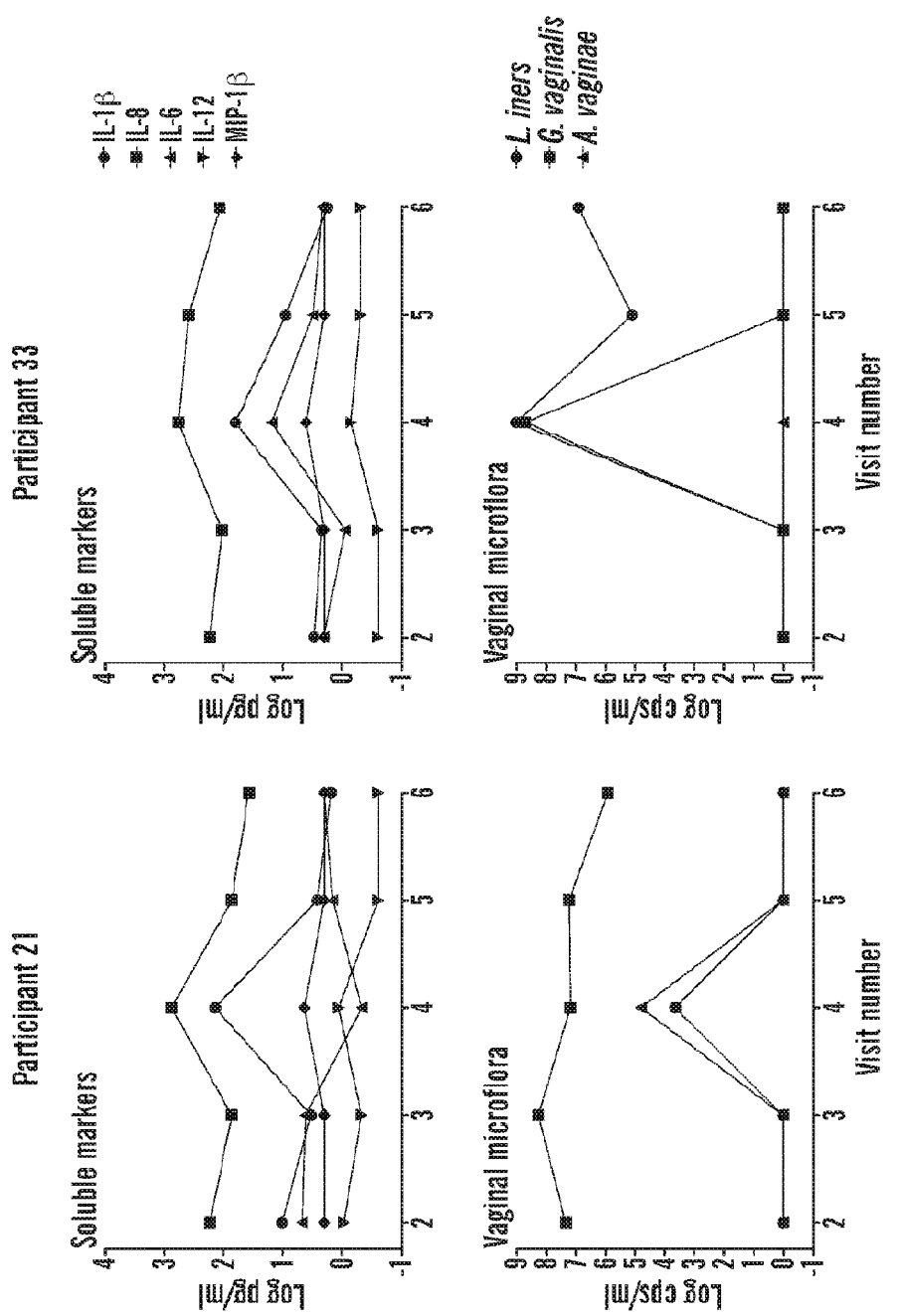
FIG. 6 illustrates the relationship between dysbiotic vaginal bacteria and mediators of inflammation. In Caucasian women with unstable vaginal microbiota followed in 4 weekly intervals, increased counts of a non-homeostatic *Lactobacillus* species (*L. iners*) coincide with peaks in numbers of the BV bacteria *A. vaginae* and *G. vaginalis* and when that happens proinflammatory cytokines and chemokines are also at a peak.
Figure 7A:
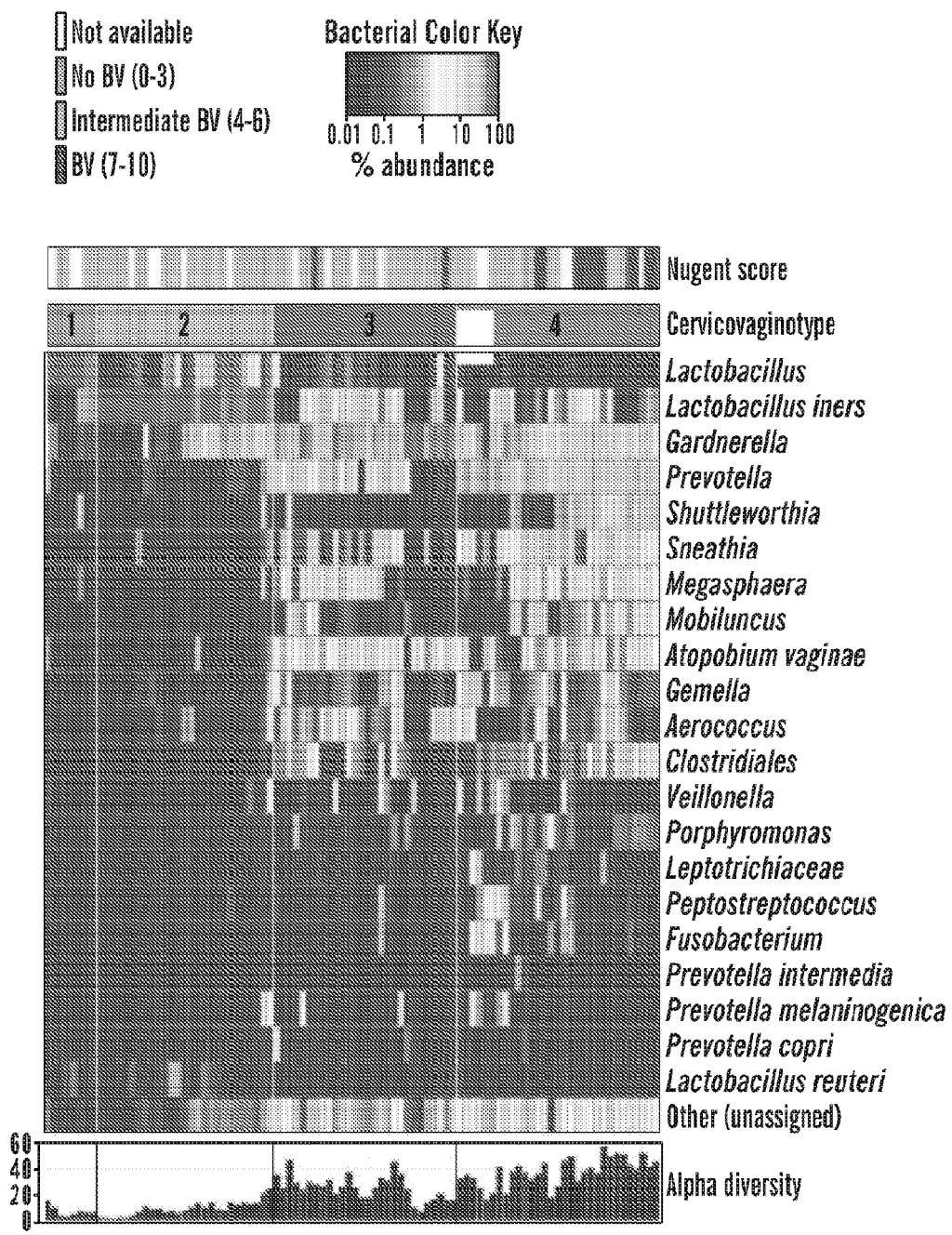
FIGS. 7A and 7B show the vaginal micobiota community states from reproductive age African women.
Figure 7B:
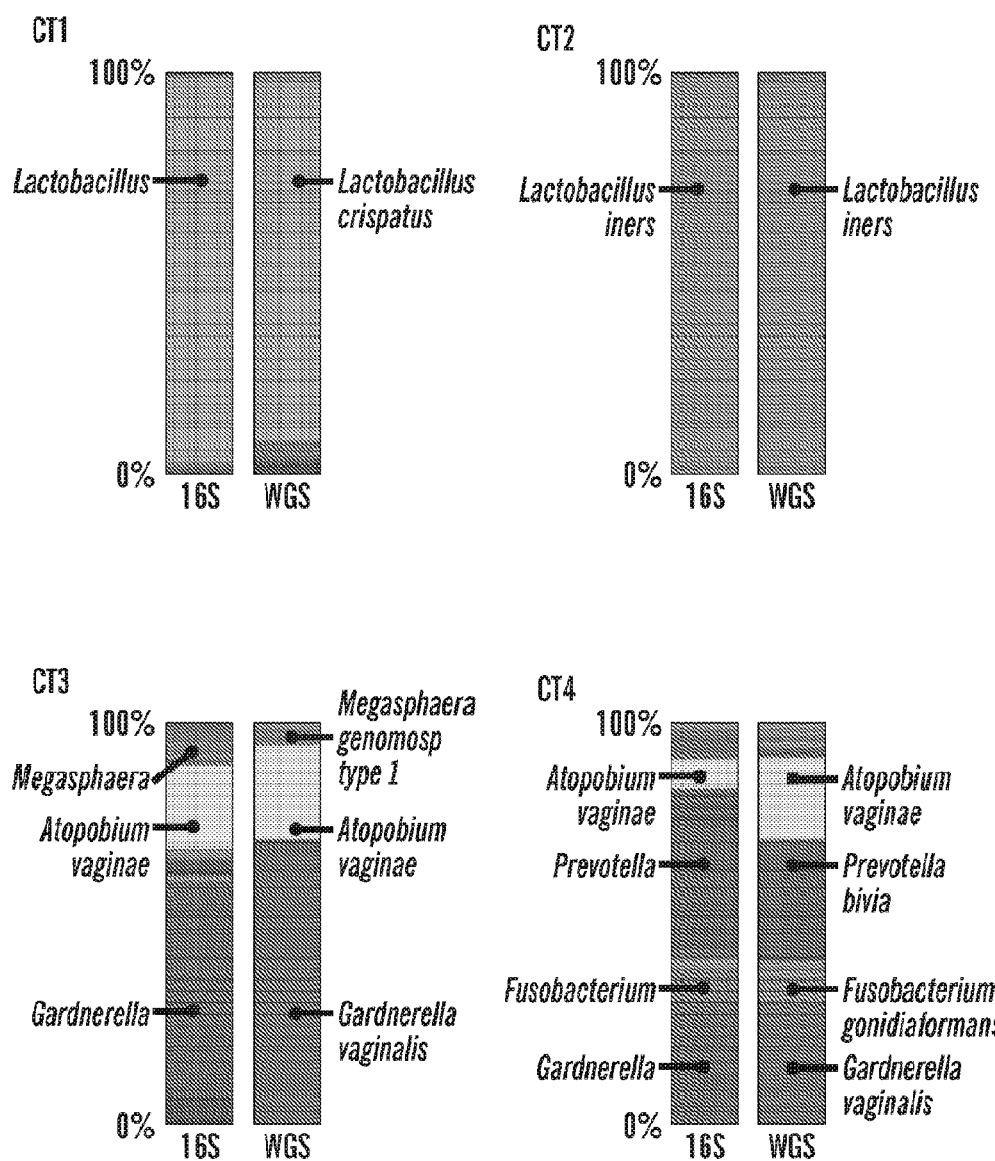
Figure 9A:
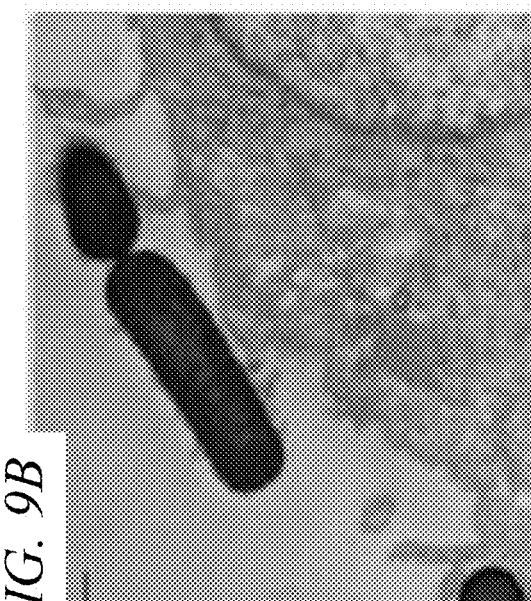
FIGS. 9A-9H show colonization of human vaginal and cervical epithelial cells by vaginal bacteria characterized by a consistent bacterial association with epithelial cells in the absence of apoptosis and cell toxicity.
Figure 9B:
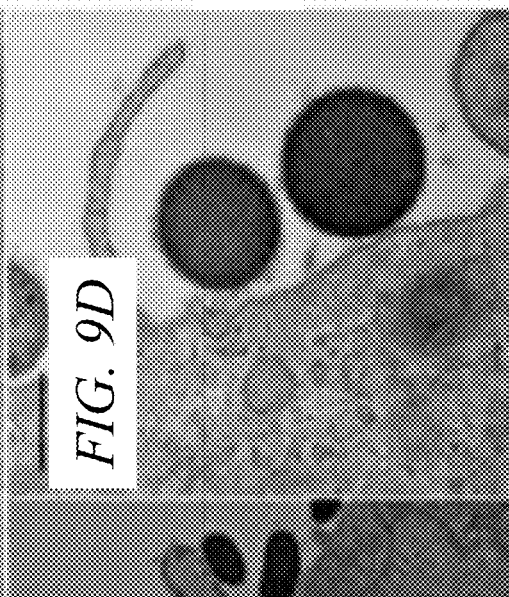
Figure 9C:
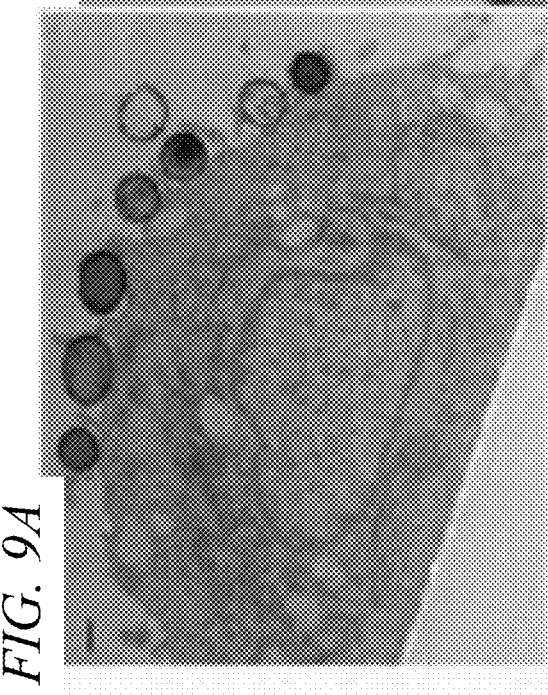
Figure 9D:
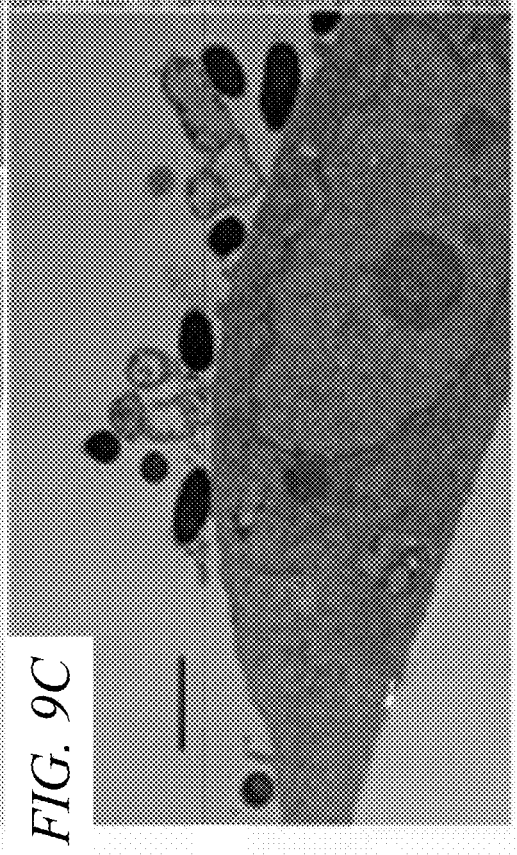
Figure 9E:
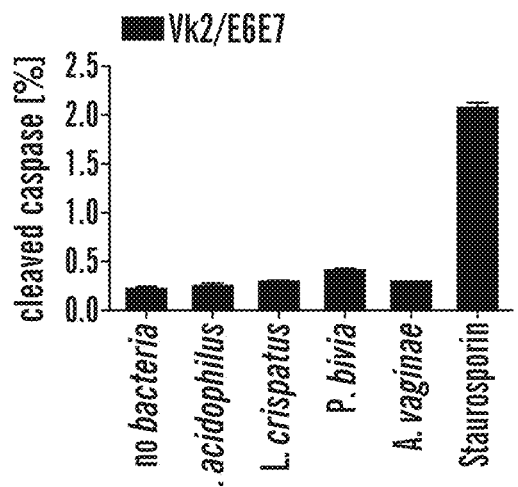
Figure 9F:
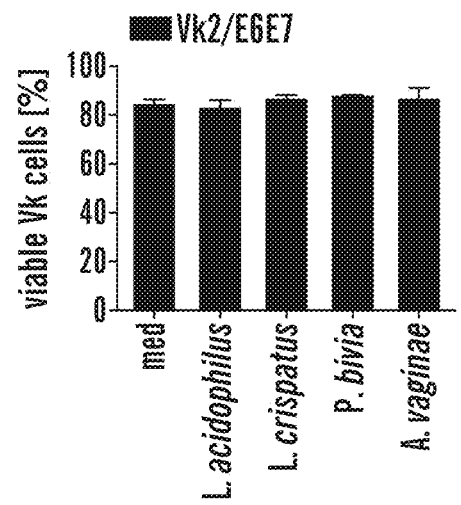
Figure 9G:
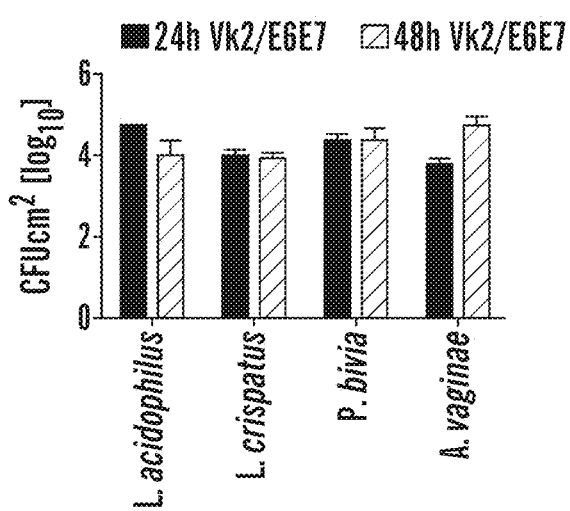
Figure 9H:
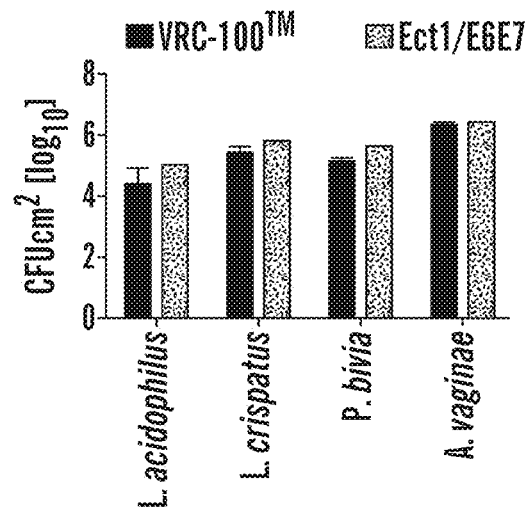

Various *Lactobacillus* species are not equal in their impact on the vaginal immunobiome. Most abundant in the vaginal environment are *L. inners, L. cristatus, L. gasseri* and *L. jensenii*. Details of *L. gasseri* isolation and genomic analysis are known in the art, see e.g., Fashemi B., et al. (2013) Microbial Ecology in Health and Disease; Fichorova R N, et al. (2011) mBio; Fichorova R N, Buck O R, Yamamoto H S, et al. (2013) Sex Transm Infect.; Yamamoto H S, Xu Q, and Fichorova R N. (2013) BMC Microbiology, which are incorporated herein by reference in their entireties. Genomic studies have associated them with microbiome community state types that are typically associated with non-BV Nugent scores (the classic microbiological measure of vaginal health[1] (FIG. 5). However, *L. inners* has turned out to be associated with increased levels of inflammatory cytokines and other signs of unwanted immune activation indicative of inflammatory state in women in contrast to the other abundant *Lactobacillus* species that are associated with lower cervicovaginal levels of inflammation[51] (FIGS. 6, 7A-7B, and 8A-8E). Comparing a NextGen derived community state type dominated by *L. crispatus* (CT1) to that dominated by *L. iners* (CT2) and to that of BV-dominate bacteria e.g. *A. vaginae* and *G. vaginalis* (CT3) or *A. vaginae, G. vaginalis* and *P. bivia* (CT4) in African women clearly showed that the *L. crispatus* is superior to *L. iners* since CT2 was associated with a tendency of higher levels of inflammatory cytokines compared to CT1, and similar to CT3 and CT4 (FIGS. 7A, 7B, and 8A-8E). The causative nature of these relationships was proven in our in vitro model[51]. Work described herein and other studies[52-57] have provided clinical validation of our well-characterized in-vitro model (FIGS. 9A-9H) used in this invention for the assessment of our medical probiotic cocktail. Higher levels of inflammation and inflammatory mediators have been linked to lower anti-microbial activity of the cervicovaginal secretions of women with BV[53].

Conclusions: The population of the vaginal environment with *Lactobacillus* bacteria that maintain a low inflammatory state is highly desirable. Among the most abundant and most affected by BV vaginotropic, Lactobacilli, *L. crispatus, L. gasseri* and *L. jensenii* are better candidates for medicinal vaginal probiotic products compared to *L. iners*. The in-vitro model described herein is well suited for testing candidate products as it is well established and predicts clinical findings.

Why a Bacterial Cocktail?

Because healthy women appear to have a microbiome dominated by either one of different *Lactobacillus* species, having a mix of the most common non-inflammatory species provides a sound clinical approach to a medicinal probiotic product targeted to diverse human populations.

Based on results described herein and published evidence described the following combination of *L. crispatus, L. jensenii* and *L. gasseri* was selected from a well-characterized pool of vaginal isolates generated at Brigham and Women's Hospital under IRB approved protocols with no tracking back to the human research subjects.

Figure 10:
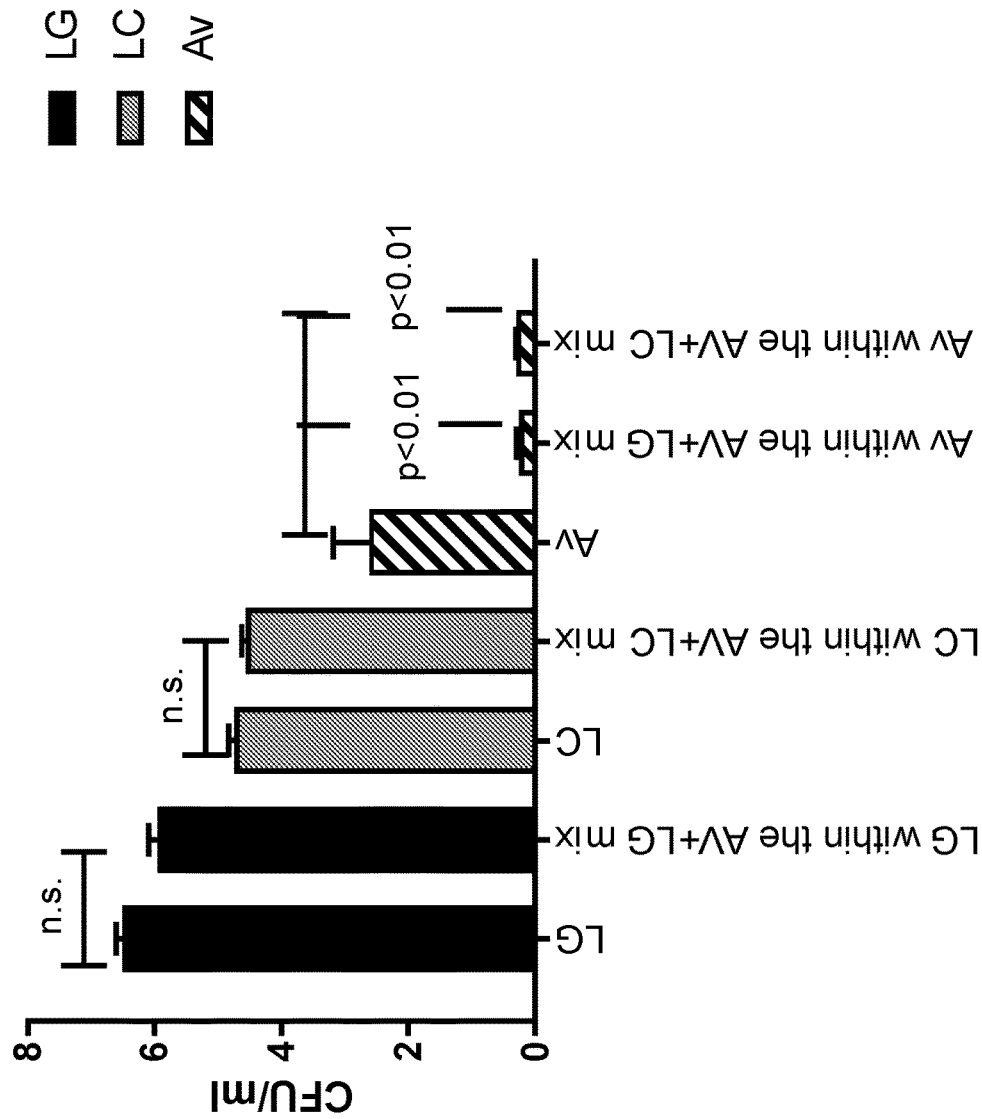
FIG. 10 shows the colonization rate on agar for the microbes alone or in combination. When seeded alone on agar, the individual lactobacilli grew comparably in the presence or absence of BV-signature bacterium *A. vaginae* and even suppressed the growth of *A. vaginae* on agar. LG=*L. gasseri*, LC=*L. crispatus*, and AV=*A. vaginae*.
Figure 11:
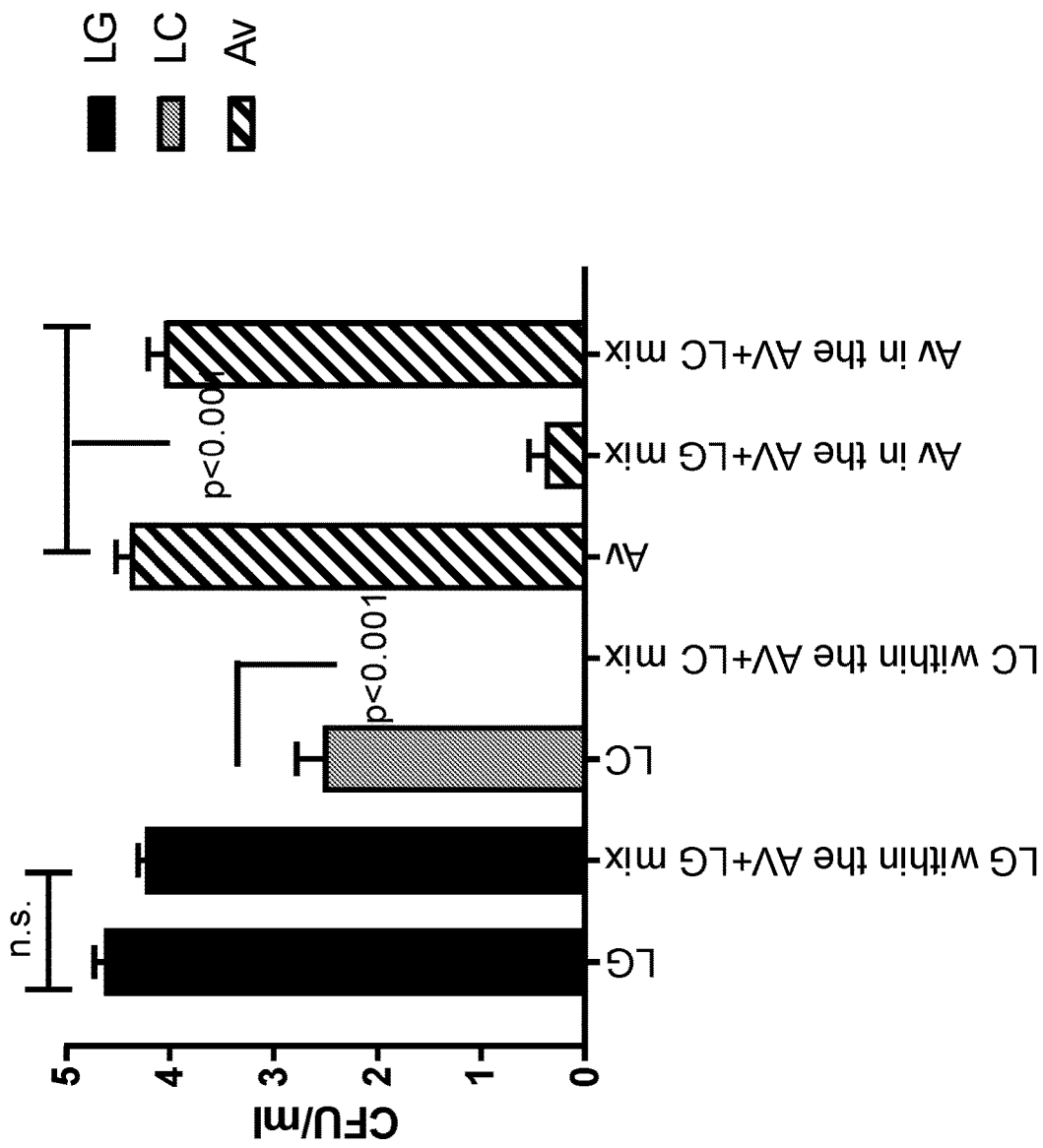
FIG. 11 shows the colonization rate on epithelial cells for the microbes alone or in combination. When allowed to colonize epithelial cells, *L. gasseri* but not *L. crispatus* maintained viable colony forming units in the presence of *A. vaginae* and *L. gasseri* but not *L. crispatus* suppressed the epithelial colonization by *A. vaginae*. LG=*L. gasseri*, LC=*L. crispatus*, and AV=*A. vaginae*.
Figure 12:
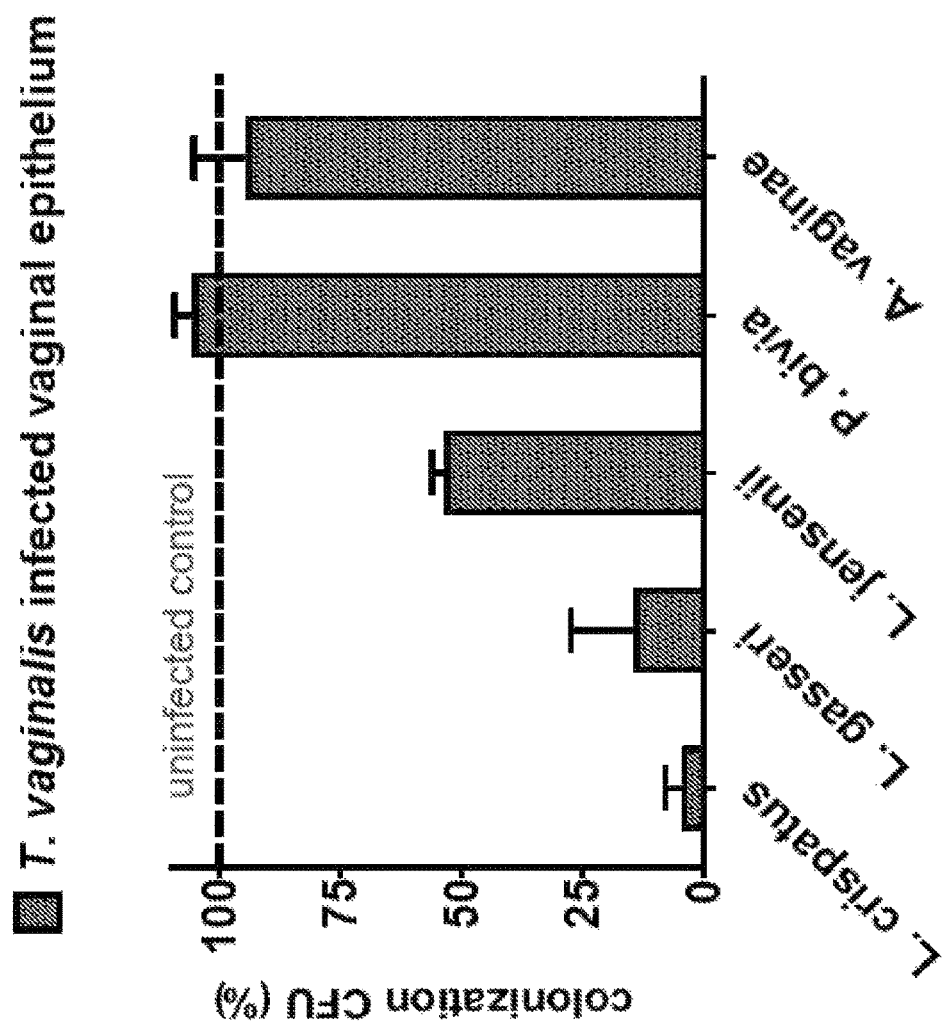
FIG. 12 shows that the effectiveness of individual microbes in treating infected *T. vaginalis* vaginal epithelium. *T. vaginalis* infection, which is the most common non-viral sexually transmitted pathogen and the most common cause of vaginitis, is associated with vaginal dysbiosis and frequently co-occurs with BV. When tested individually, *L. jensenii* was shown to be most resistant to the suppressive effects of *T. vaginalis*.
Figure 12:
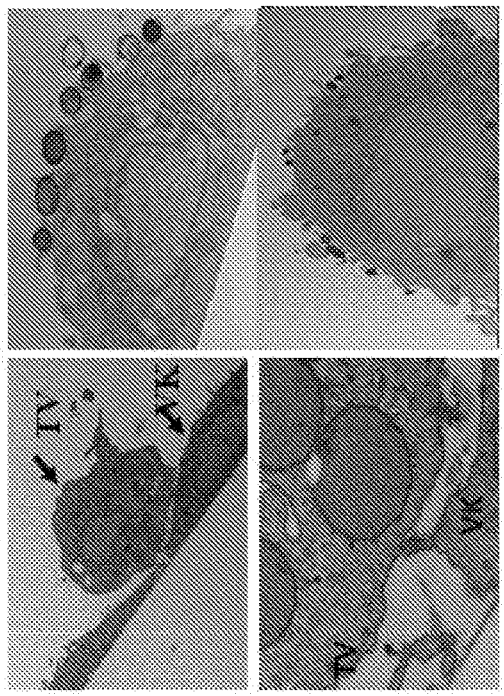

This model provided further rationale choosing a cocktail of bacterial species rather than a single species based medicinal product (FIGS. 10-12). When seeded alone in the absence of epithelial cells, the lactobacilli grew comparably in the presence or absence of BV-signature bacterium *A. vaginae* and even suppressed the growth of *A. vaginae* on agar (FIG. 10). However, when allowed to colonize epithelial cells, *L. gasseri* but not *L. crispatus* maintained viable colony forming units in the presence of *A. vaginae* and *L. gasseri* but not *L. crispatus* suppressed the epithelial colonization by *A. vaginae* (FIG. 11). These data indicated that in a therapeutic mix *L. gasseri* may assist *L. crispatus* in surviving in a BV environment. Furthermore, when tested individually, *Lactobacillus jensenii* was shown to be most resistant to the suppressive effects of *T. vaginalis*, a protozoan parasite that is the most common cause if vaginitis and frequent companion of BV (FIG. 12). These data supported our novel concept that a mix of the three species would be assisting *Lactobacillus* survival and competition against vaginal pathogens including BV bacteria and TV.

Figure 13A:
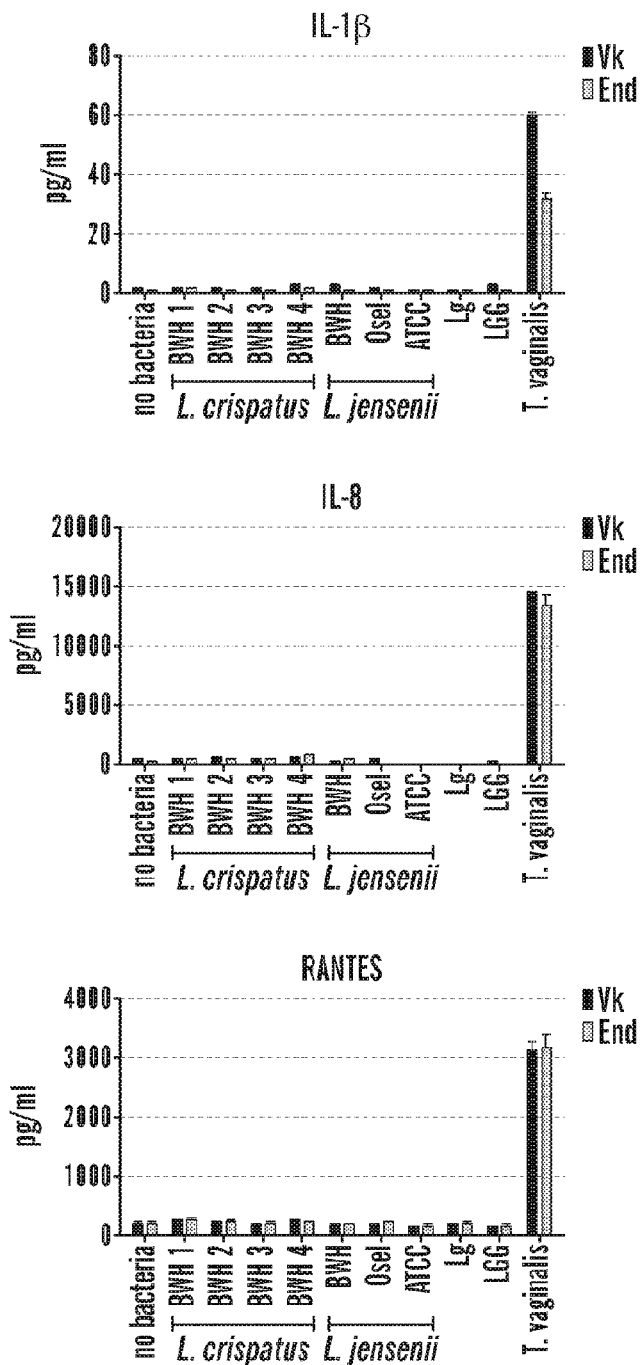
Figure 13A:
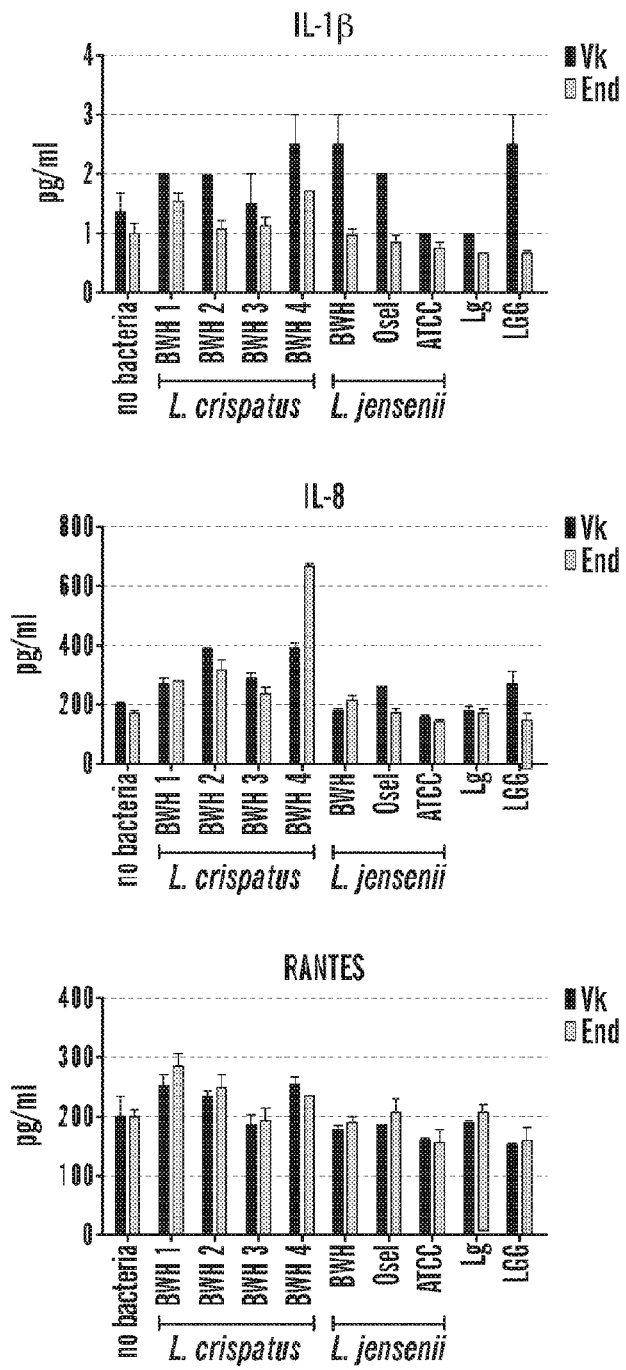
Figure 13B:
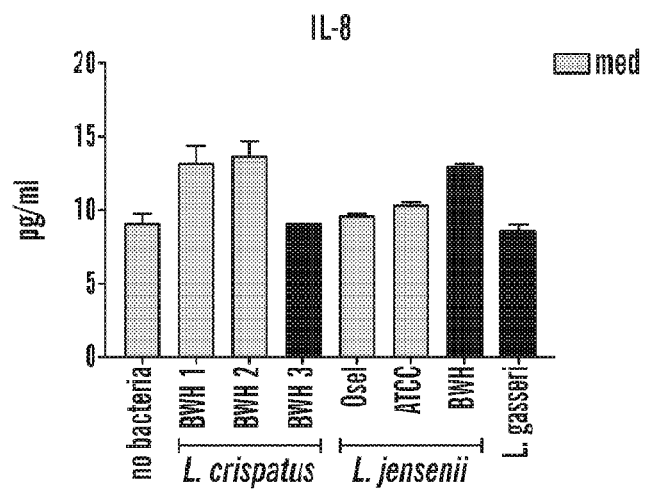
Figure 13B:
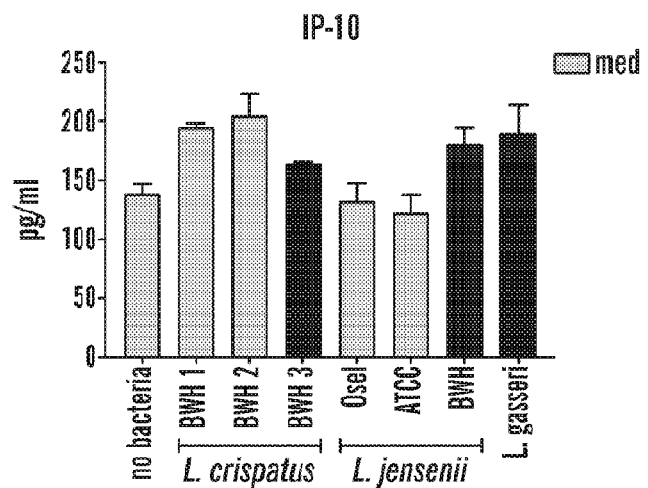
Figure 13B:
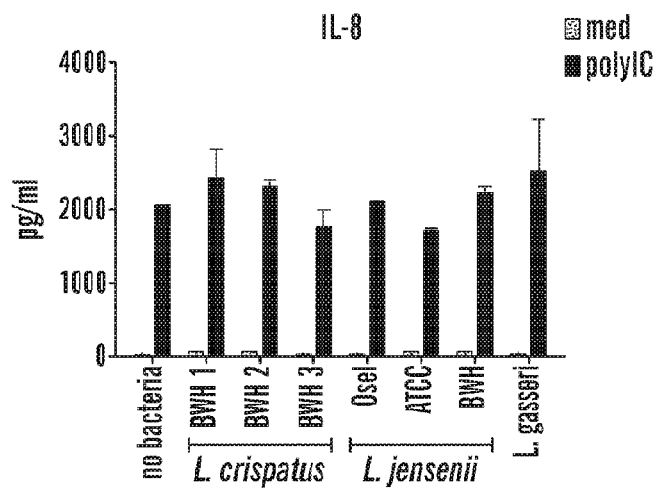
Figure 13B:
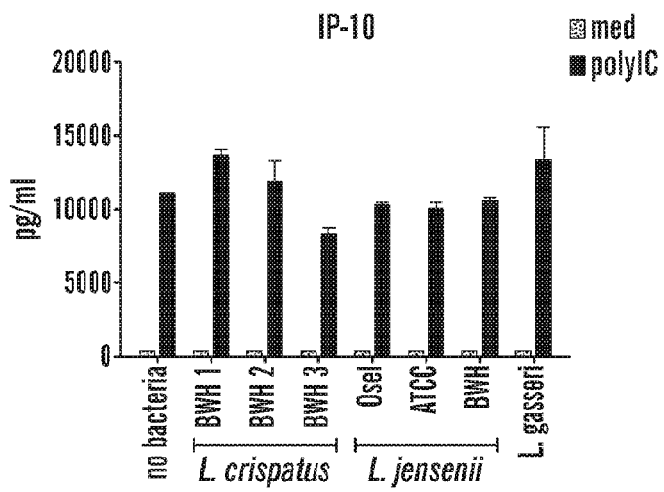
Figure 13B:
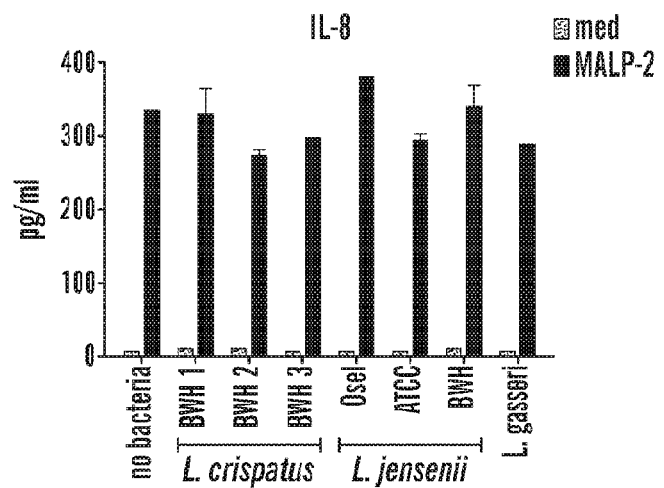
Figure 13B:
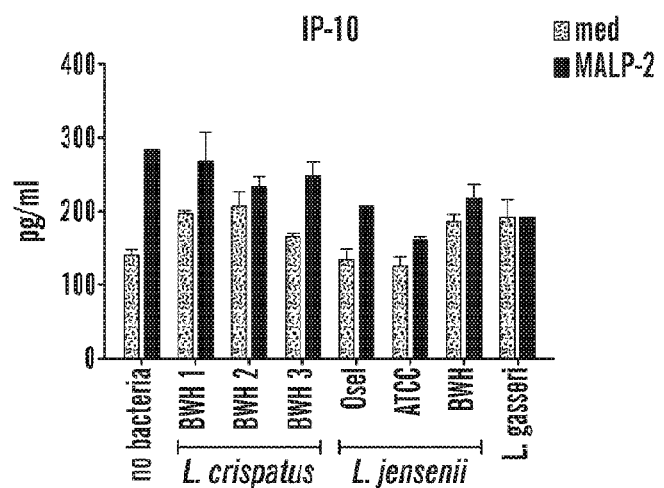
Figure 13B:
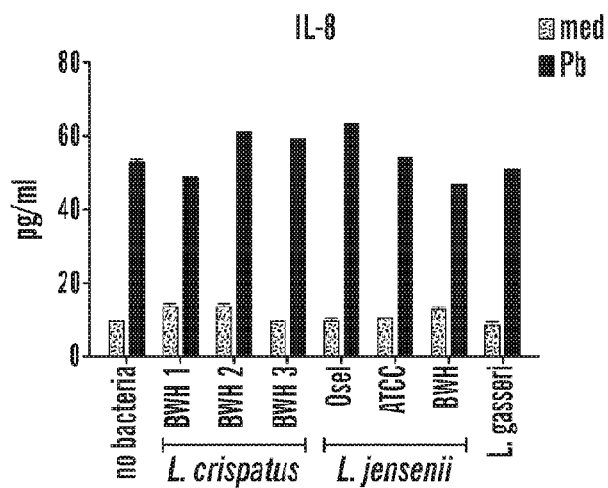
Figure 13B:
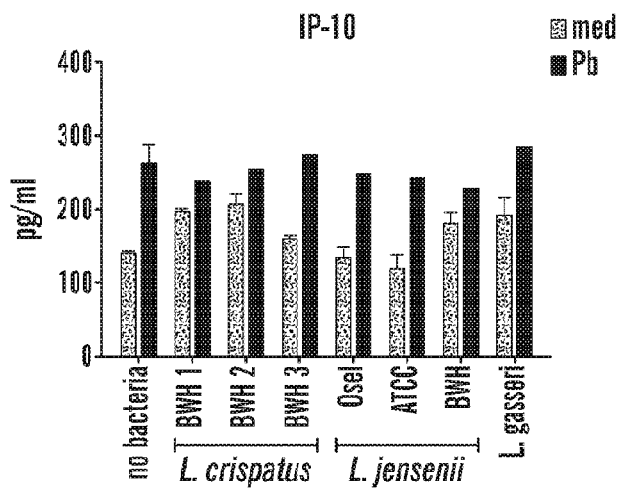
Figure 13B:
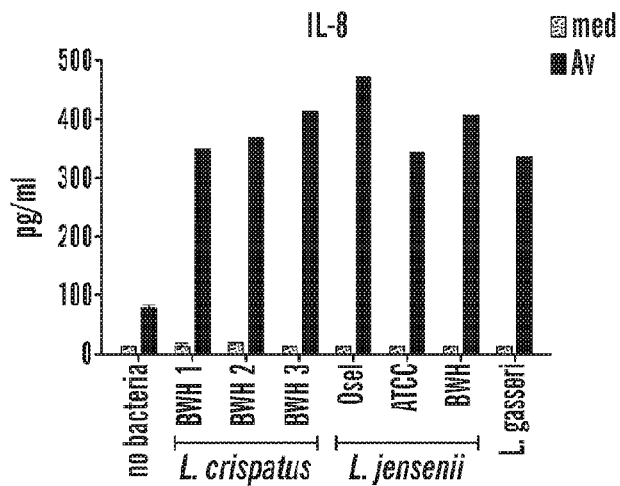
Figure 13B:
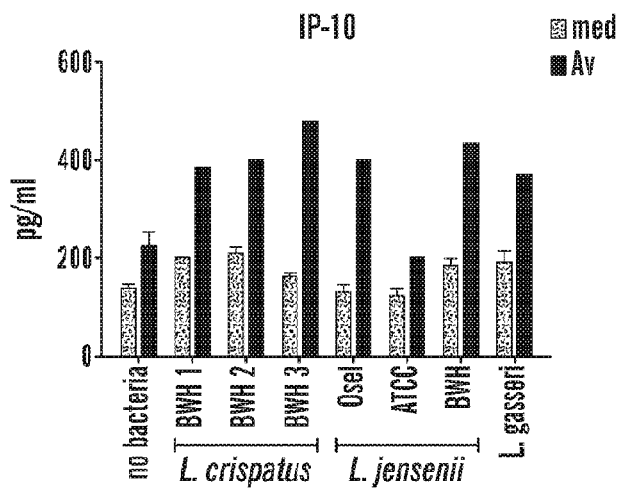
Figure 13B:
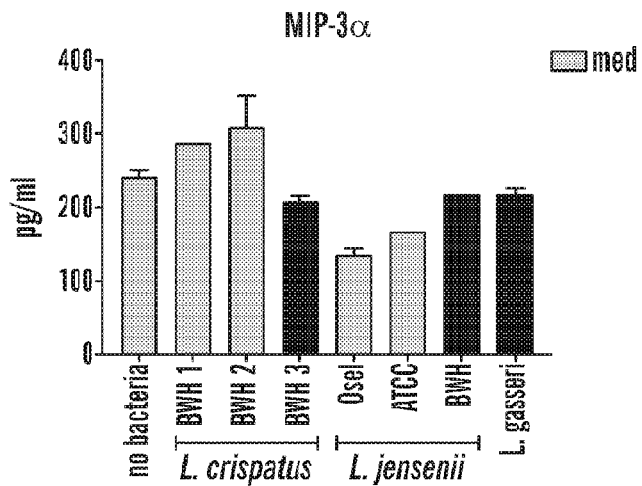
Figure 13B:
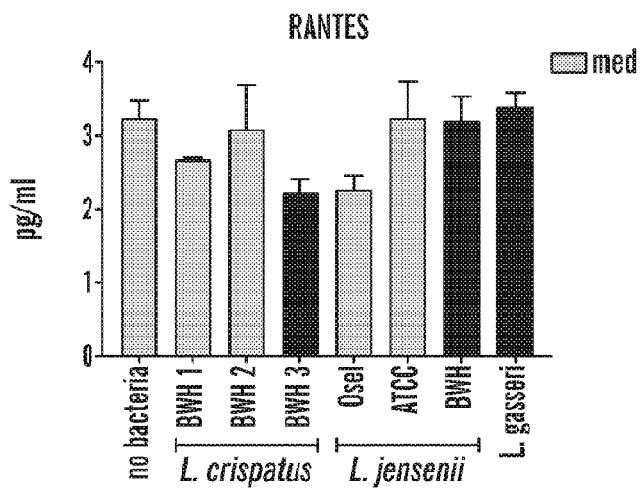
Figure 13B:
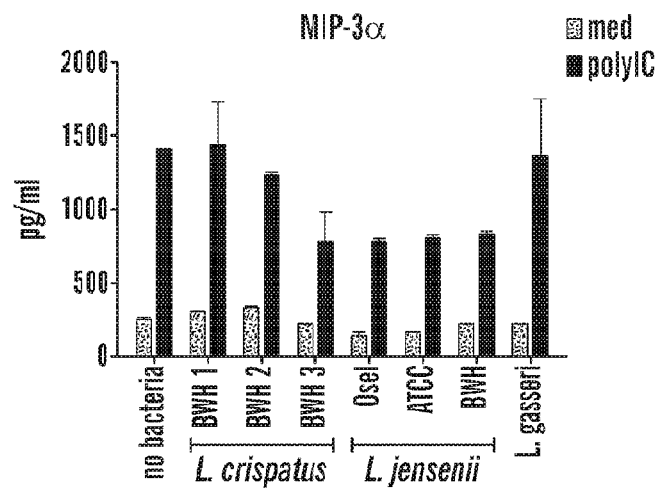
Figure 13B:
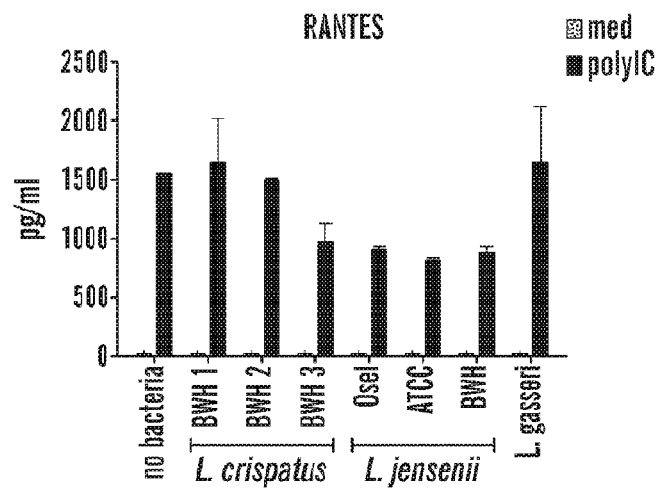
Figure 13B:
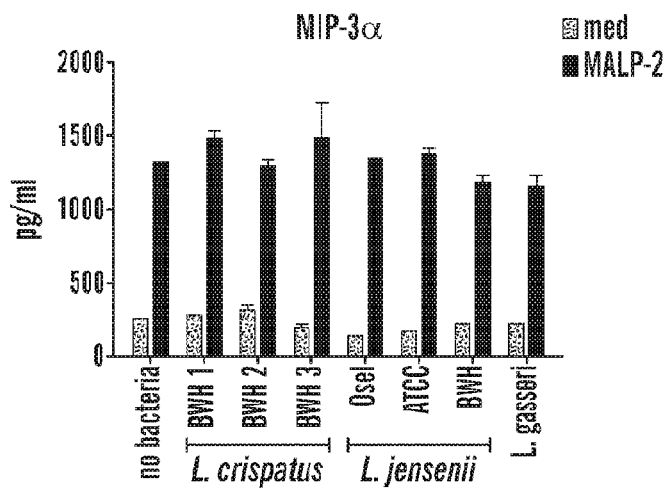
Figure 13B:
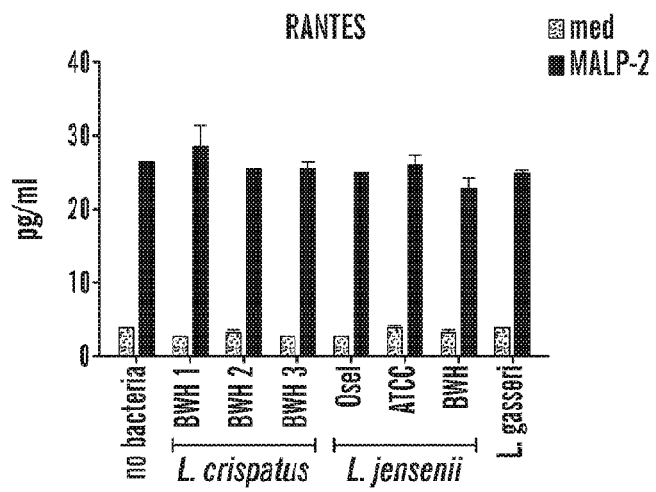
Figure 13B:
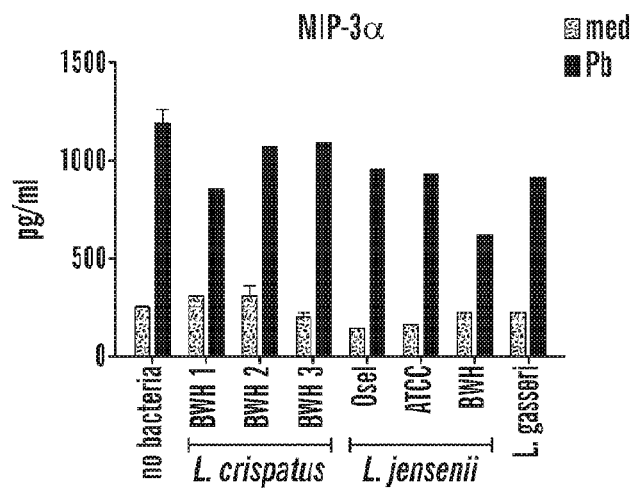
Figure 13B:
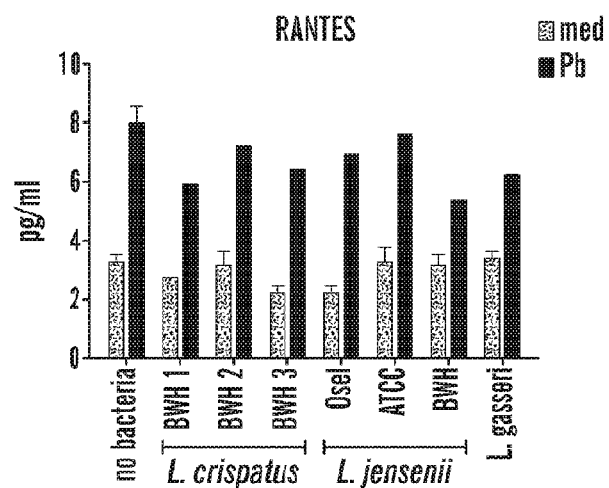
Figure 13B:
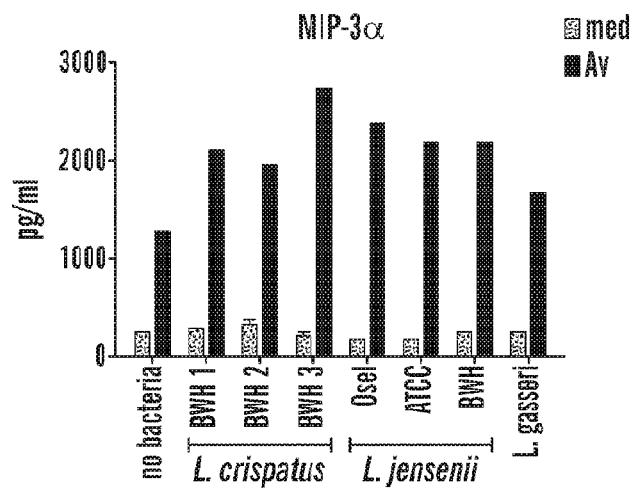
Figure 13B:
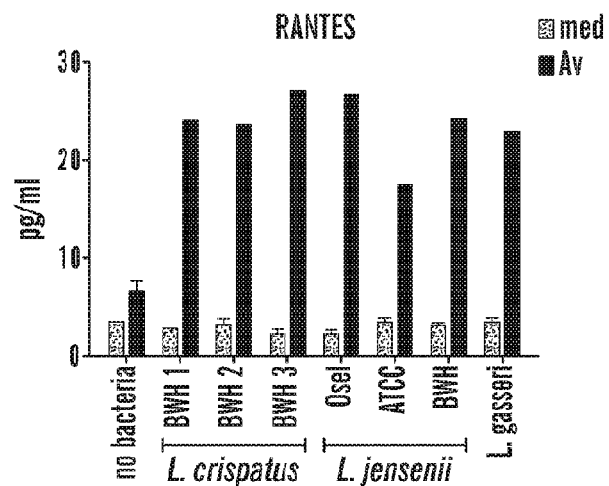

An important finding in the model is that no all *Lactobacillus* strains within a species are equal in their ability to maintain a homeostatic environment (FIG. 13A-13C). The strains differed by their immune properties measured by vaginal and cervical cytokines and chemokines (FIGS. 13A-13C). They could be ranked by levels of proinflammatory mediators included in current vaginal product safety algorithms due to their relevance to risk of viral infections, e.g. HIV and reproductive outcomes. *Lactobacillus* strains also differed by their ability to suppress colonization by the major BV biofilm forming organisms *G. vaginalis* (FIG. 13D). These findings confirmed the importance of choosing the right strains for the vaginal medicinal product.

Base on the findings reported herein, criteria for choosing the right bacterial strains for medicinal cocktail was established. The bacterial strain must meet the following criteria to be considered useful in treating BV: (1) was isolated from a healthy reproductive age woman or a pregnant woman with term delivery, (2) displays phenotypic and genetic proof of *Lactobacillus* species, (3) is distinct from commercially available strains, (4) has homeostatic immune properties, (5) can stably colonize the human vaginal epithelium, (6) displays competitive vaginal colonization in the presence of vaginal pathogens, and optionally (7) has in-vitro anti-microbial properties.

Medicinal Probiotic Cocktail

The cocktail is comprised of unique strains selected and combined in a specific manner through a unique combination of methods. The strains represent *Lactobacillus* crispatus, *Lactobacillus jensenii*, and *Lactobacillus* gasseri, which are dominant species in the vaginal microbiota of healthy women and associated with a healthy non-inflammatory vaginal microenvironment.

The bacterial isolates and the originating vaginal environment were phenotyped by a combination of established microbiological techniques including: Vaginal pH, Nugent Score, Whiff Test, API 20E system (BioMerieux, Inc. Durham, NC), API 20 C AUX system (BioMerieux, Inc. Durham, NC), Rapid ANA II system (REMEL Inc., Norcross, GA), Microbial Identification System (Microbial ID Inc., Newark, DE), Gas liquid chromatographic analysis of glucose fermentation products, Total anaerobe concentrations, Total aerobe concentrations, Enzymatic activity (Lipase), phospholipase A2 and phospholipase C, Hydrogen peroxide production.

Figure 14A:
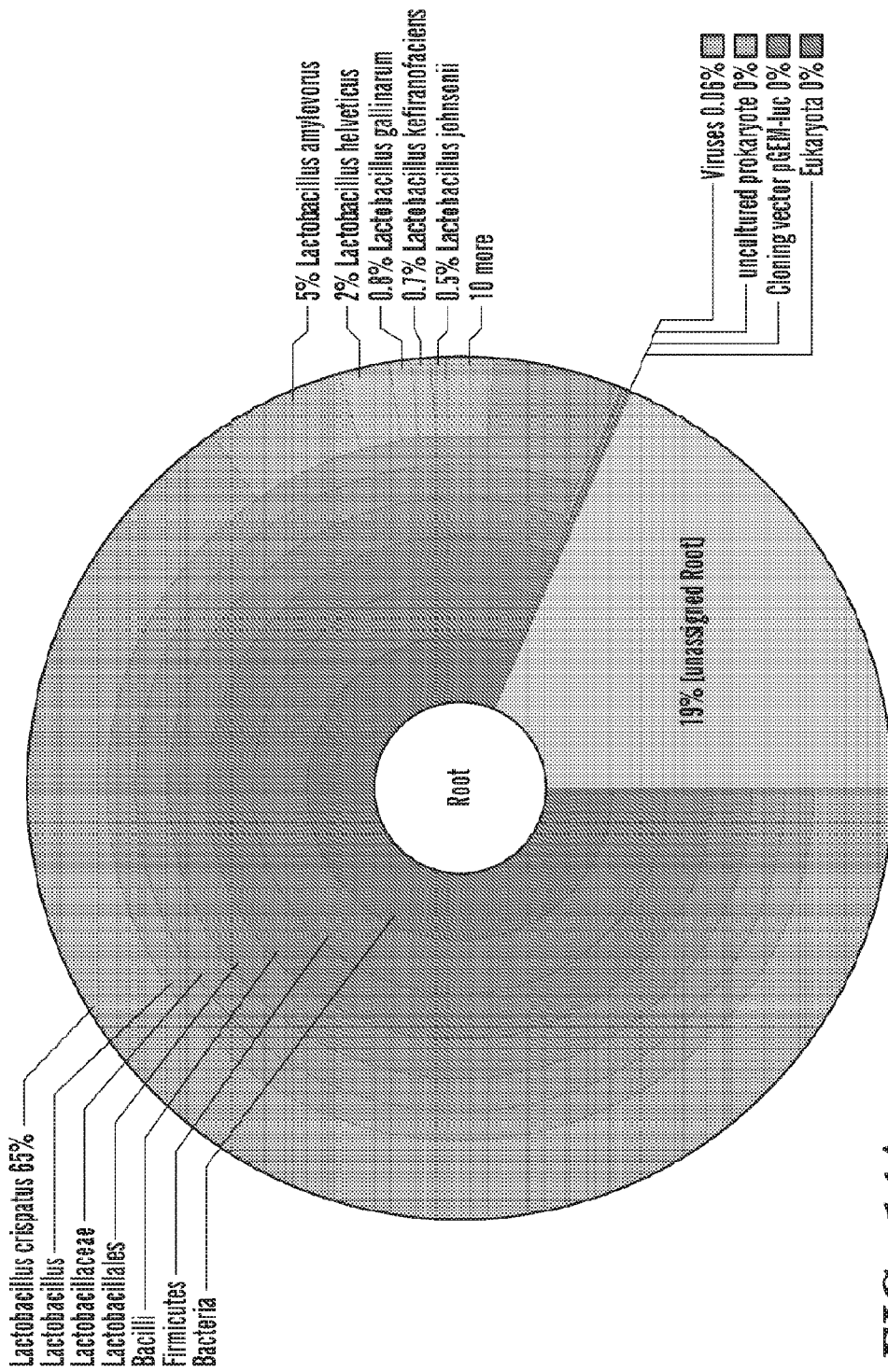
FIGS. 14A-14C shows a molecular analysis confirming species identity of isolated strains: (FIG. A). *L. crispatus*, (FIG. B). *L. jensenii*, (FIG. C) *L. gasseri*.
Figure 14B:
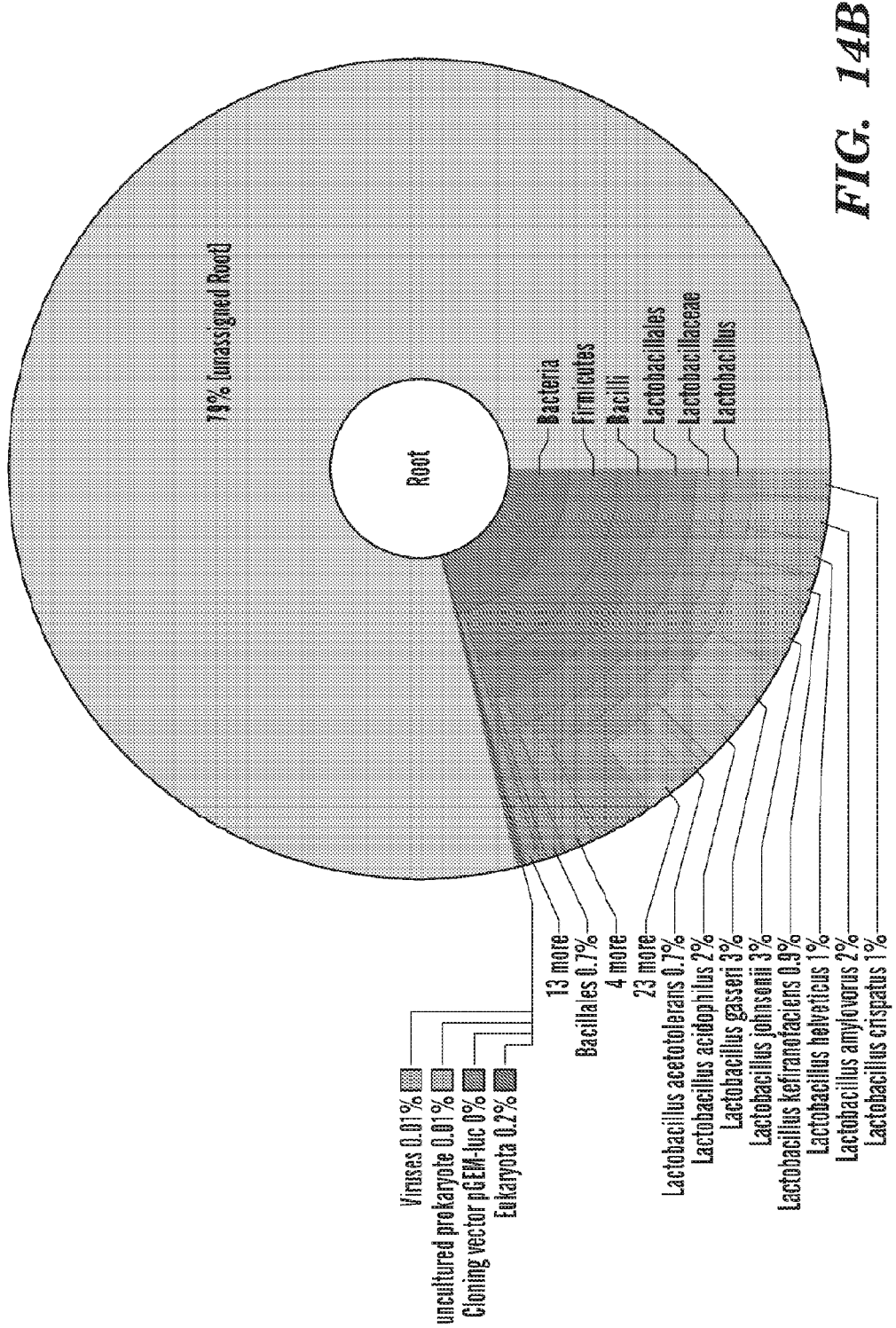
Figure 14C:
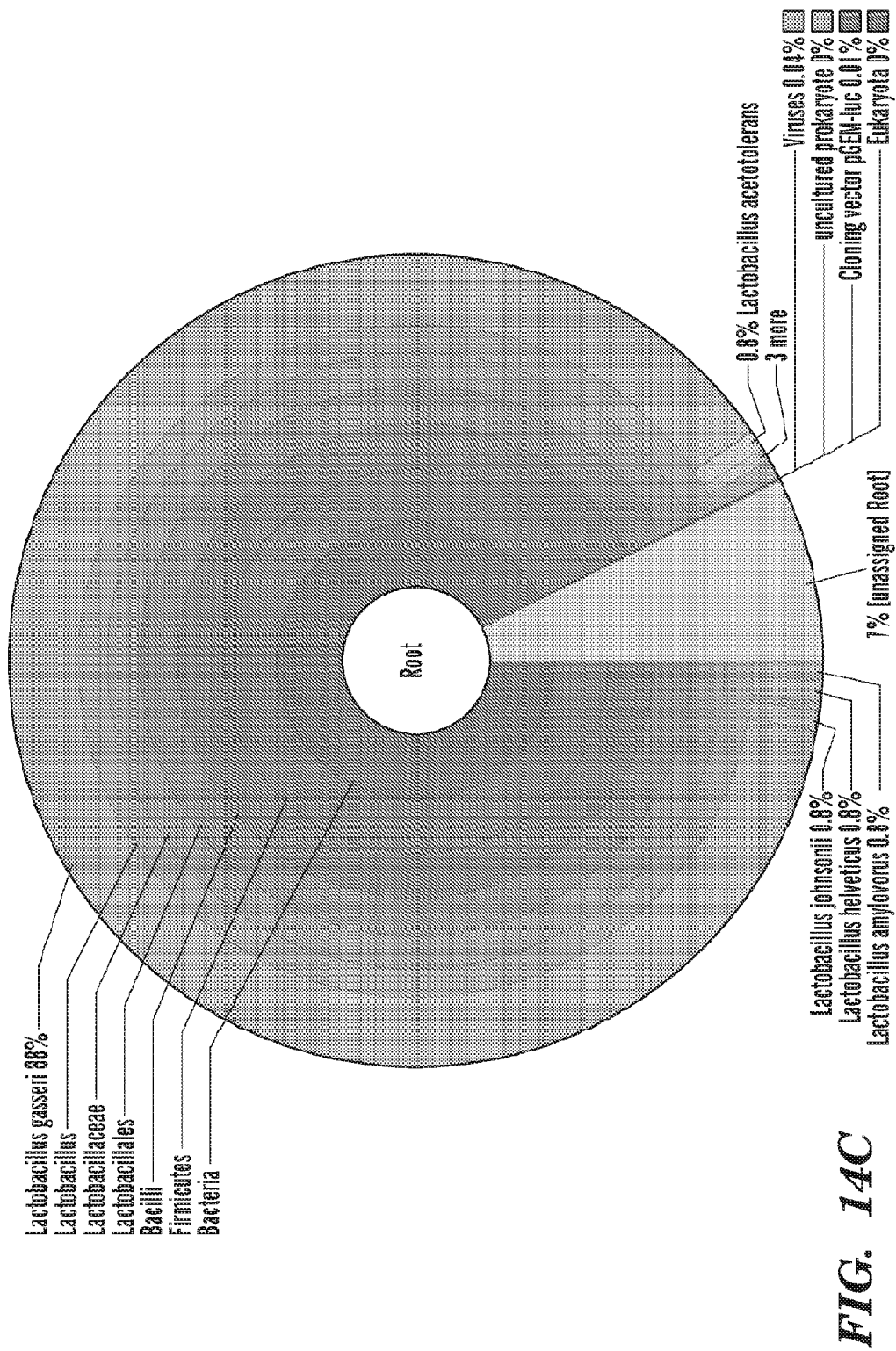
Figure 15:
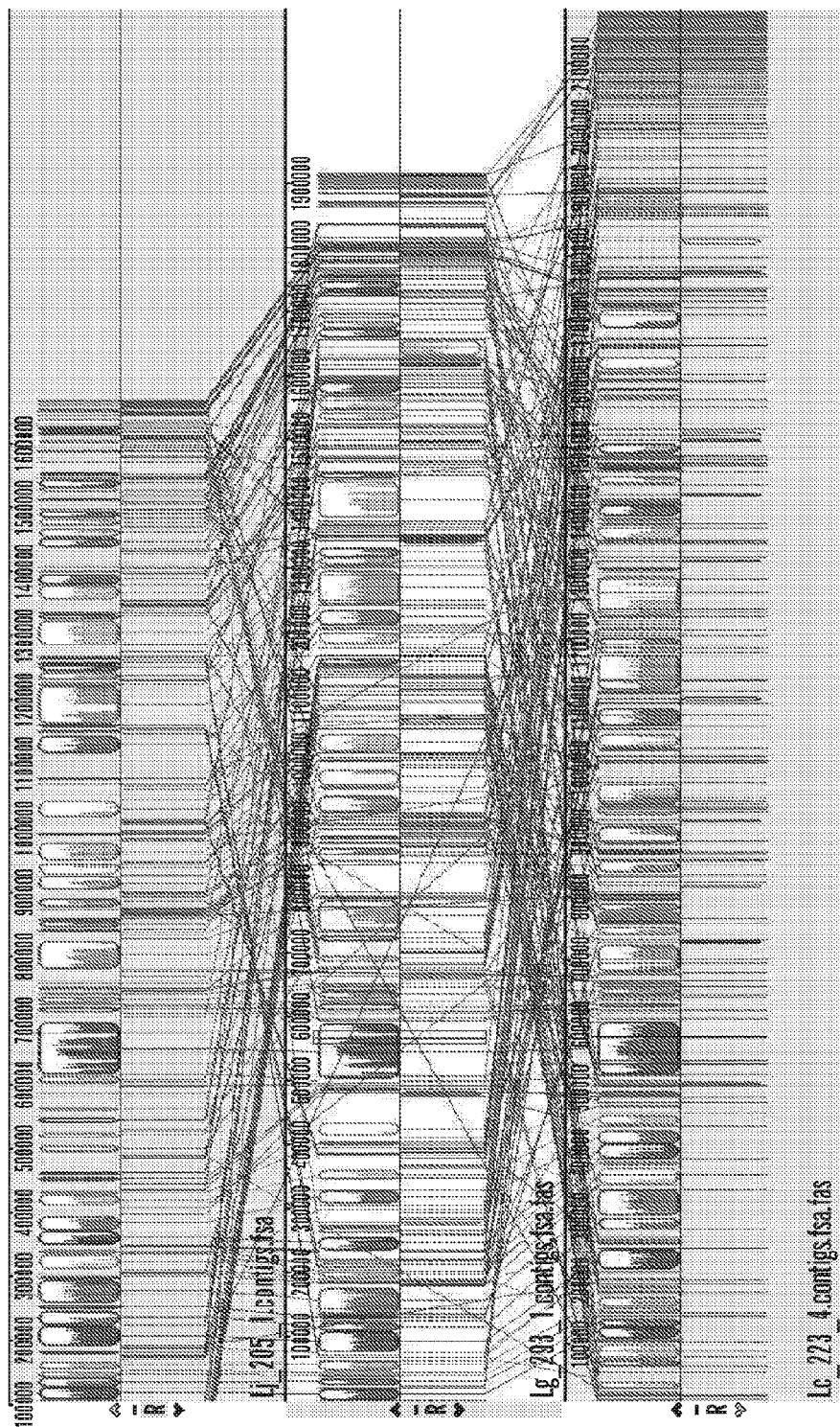
FIG. 15. Shows genome alignment of the three selected strains and known genomes. BLASTN search identified that the three sequenced genomes (Lc=*L. crispatus* 223310, Lj=*L. jensenii* 2054210, and Lg=*L. gasseri* 293-13) are quite divergent from each other, sharing less than about 80% nucleotide sequence identity.
Figure 16A:
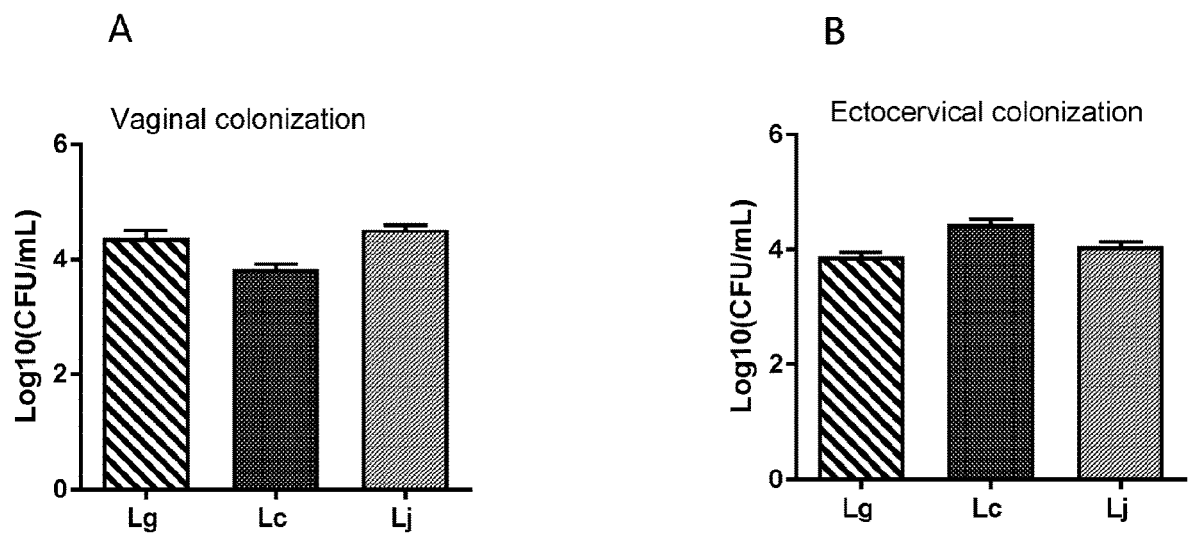
FIGS. 16A and 16B shows reproducible colonization activity of the three selected *Lactobacillus* strains (Lc=*L. crispatus* 223310, Lj=*L. jensenii* 2054210, and Lg=*L. gasseri* 29313). A steady recovery of colony forming units (CFU) from human vaginal (FIG. 16A) and ectocervical (FIG. 16B) epithelial cells was achieved upon 24 h exposure to the three selected strains in the absence of epithelial toxicity measured by no increase in cleaved caspase-3 and lack of change in total caspase levels by comparison to non-infected baseline and cells stimulated with pro-apoptotic agents e.g. staurosporin and a viral mimic poly(I:C) (FIG. 16B)
Figure 16B:
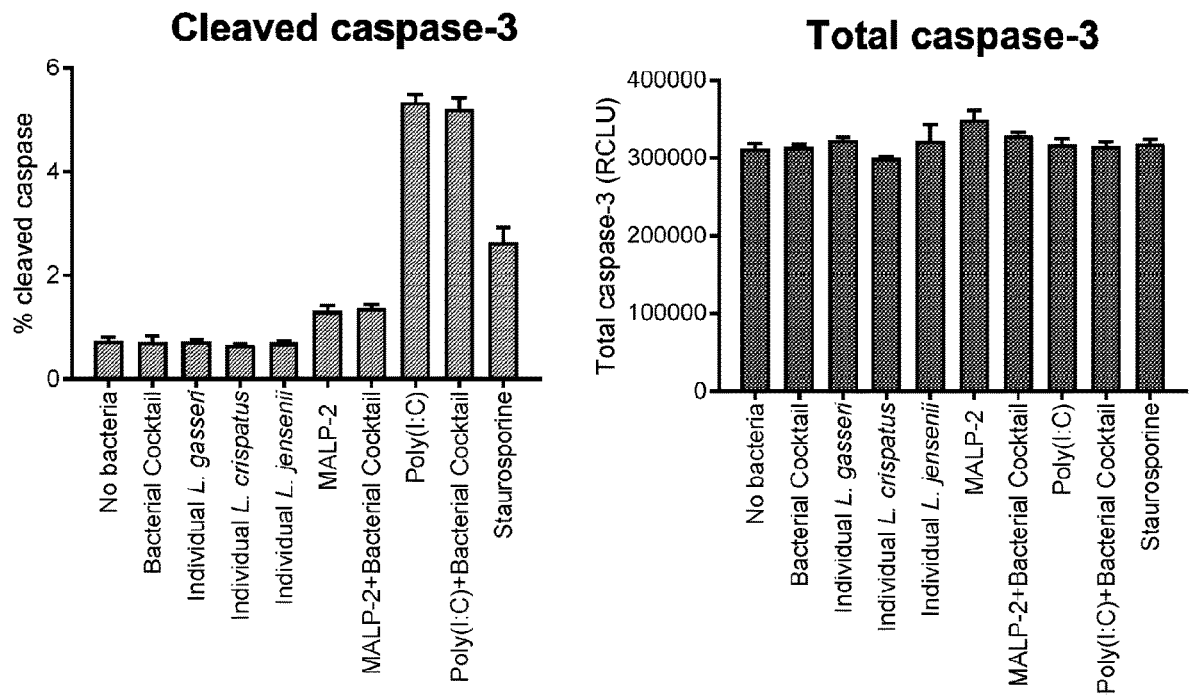
Figure 17A:
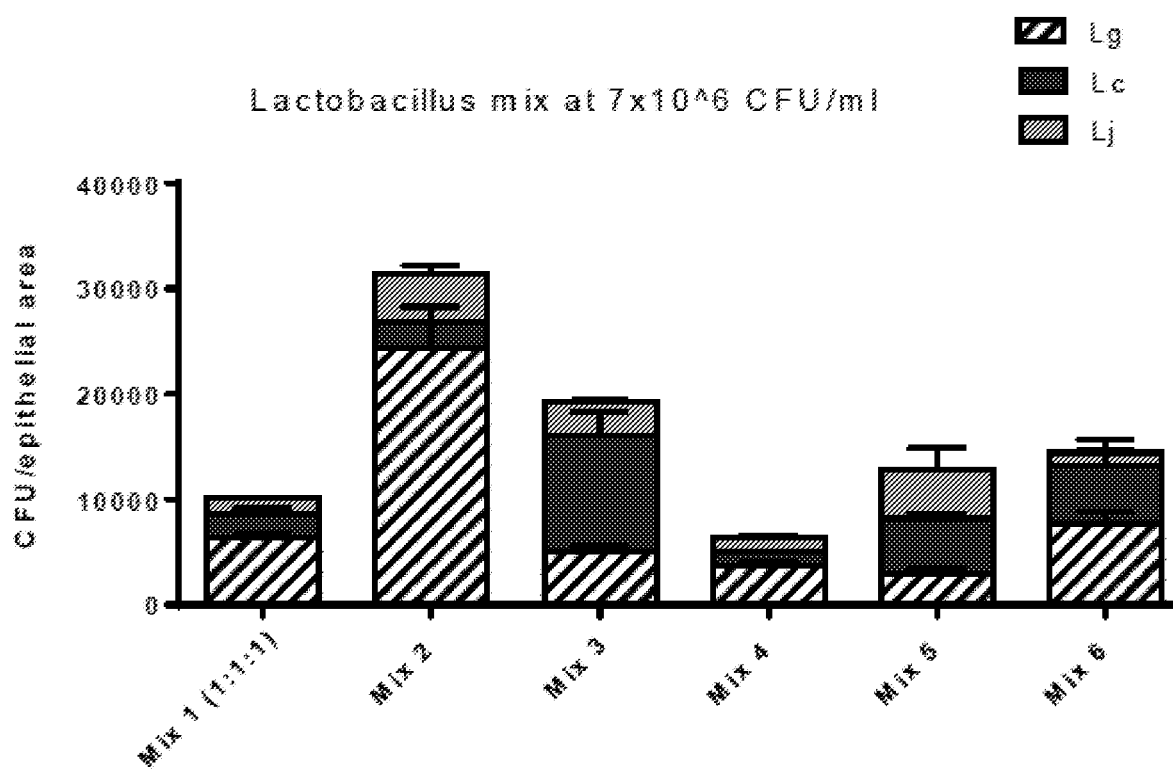
FIGS. 17A and 17B show the growth proportions of the indicated bacteria when colonized at differing ratios. The strains were applied at a total concentration of $7 \times 10^6$/ml (FIG. 17A) and later optimized to a total initial concentration of $7 \times 10^5$/ml (FIG. 17B) which resulted in a synergistic growth that exceeded total *Lactobacillus* colonization when the individual bacteria were applied alone at the same concentration. Based on these results formulas 2 and 4 were excluded from further testing). The bars represent duplicate cultures (mean and SEM) in at least 3 experiments with each formula tested side by side. (Lc=*L. crispatus* 223310, Lj=*L. jensenii* 2054210, and Lg=*L. gasseri* 29313).
Figure 17B:
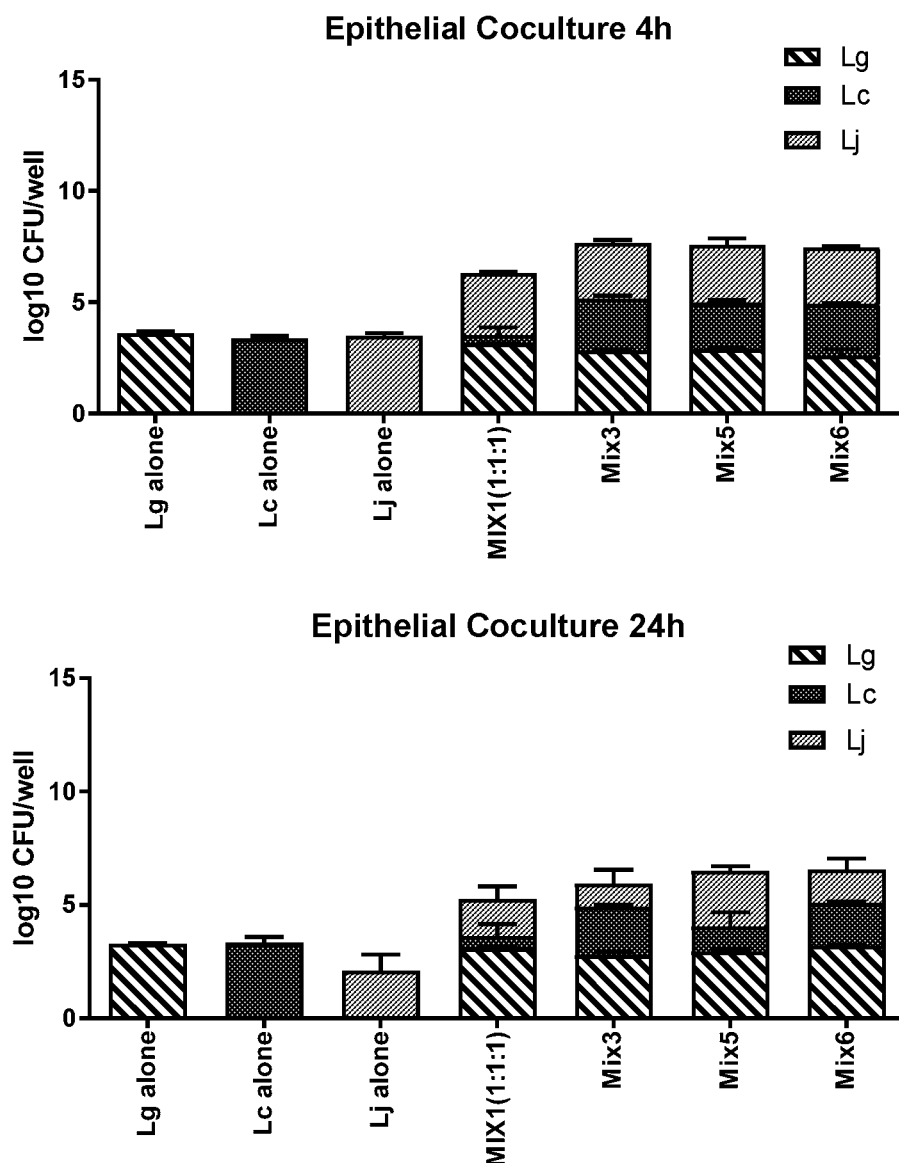
Figure 18:
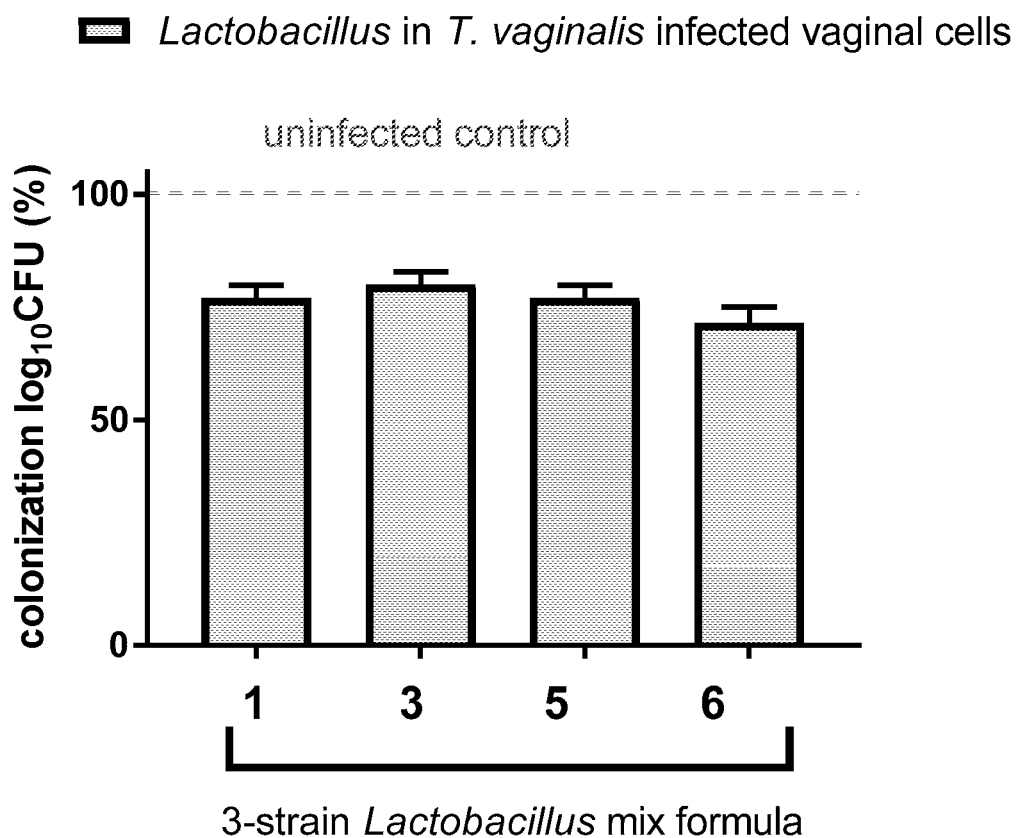
FIG. 18 shows the benefit of using a 3-strain formula in treating infected *T. vaginalis* vaginal epithelium. An unexpected finding was that when the infection was conducted in vaginal epithelium colonized with the 3-strain mix, the cumulative *Lactobacillus* colonization rate was higher compared to that of most individual strains, demonstrating resistance to the microbiome perturbations by *T. vaginalis*.
Figure 19A:
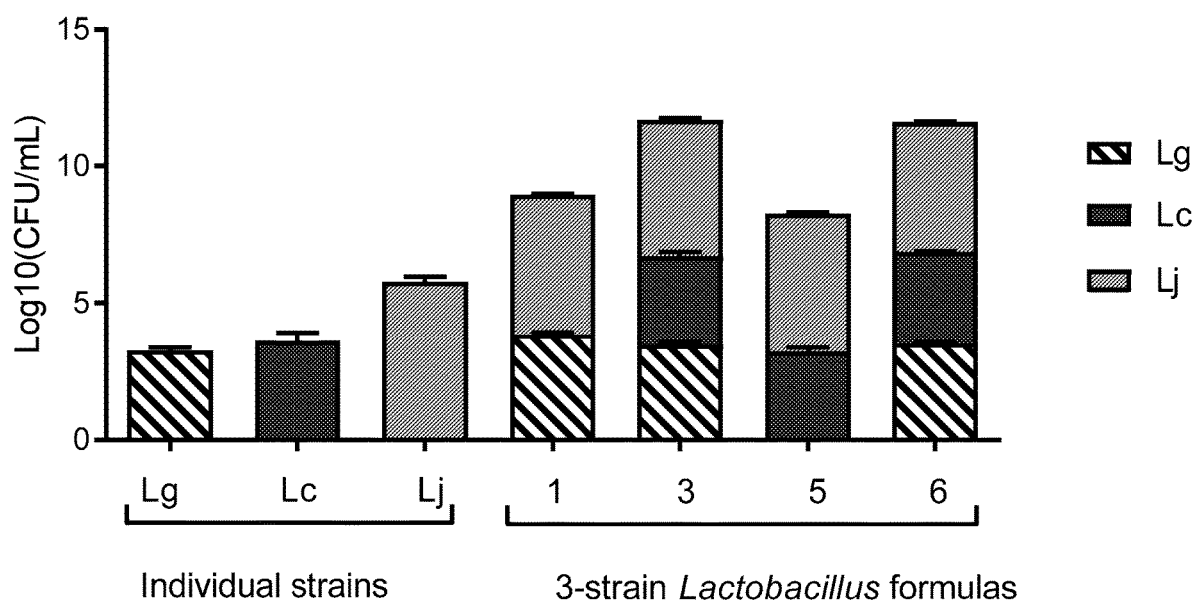
FIGS. 19A-19C shows the colonization benefit of combining the 3 select strains in terms of better survival in the presence of BV signature bacterium *A. vaginae*, *P. vivia*, and *G. vaginalis*. Ming the three selected strains *L. crispatus* 223310 (Lc), *L. jensenii* 2054210 (Lj) and *L. gasseri* 29313 (Lg) in an optimized mix formula resulted in about 2-fold better cumulative *Lactobacillus* colonization rate in the presence of *A. vaginae* (FIG. 19A) or *P. bivia* (FIG. 19B) compared to the same strains applied individually, and a better preservation of colonization by each individual *Lactobacillus* strain in the mix compared to an equal proportion 1:1:1 demonstrating a clear benefit and indication for using the optimal mix formula for restoring the healthy *Lactobacillus*-dominated microflora in patients with BV. All 3-strain mixes resulted in a better *Lactobacillus* colonization compared to individual strains in the presence of *G. vaginalis* (FIG. 19C).
Figure 19B:
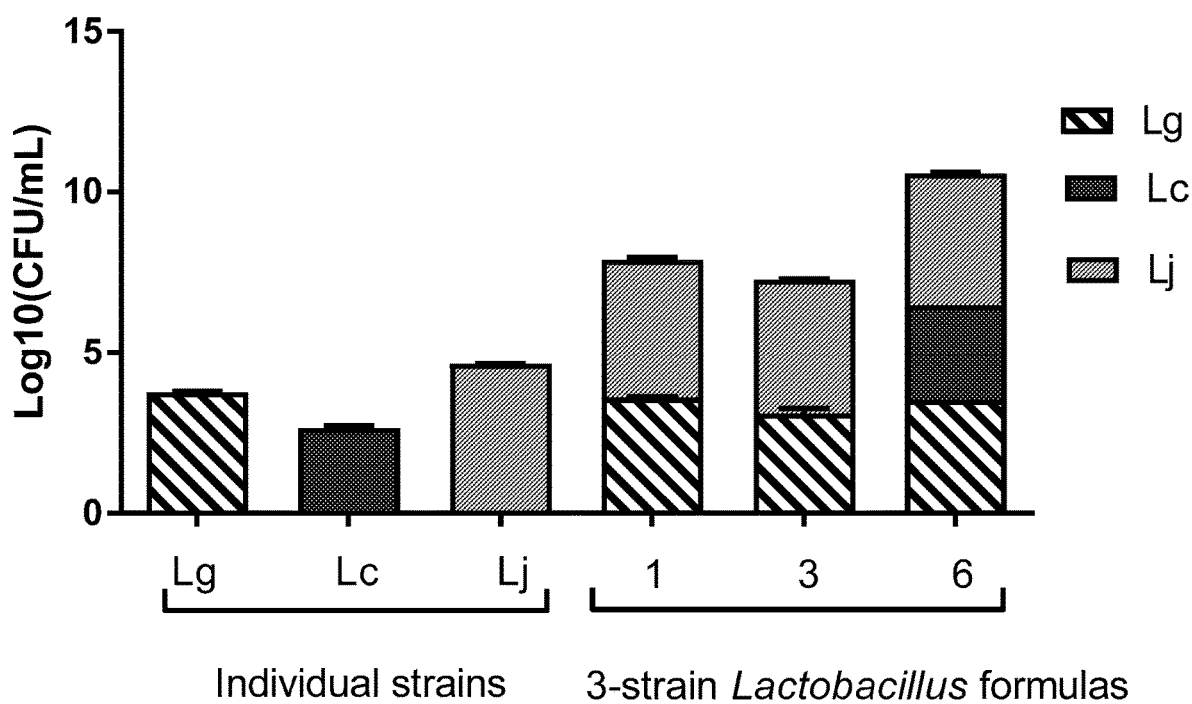
Figure 19C:
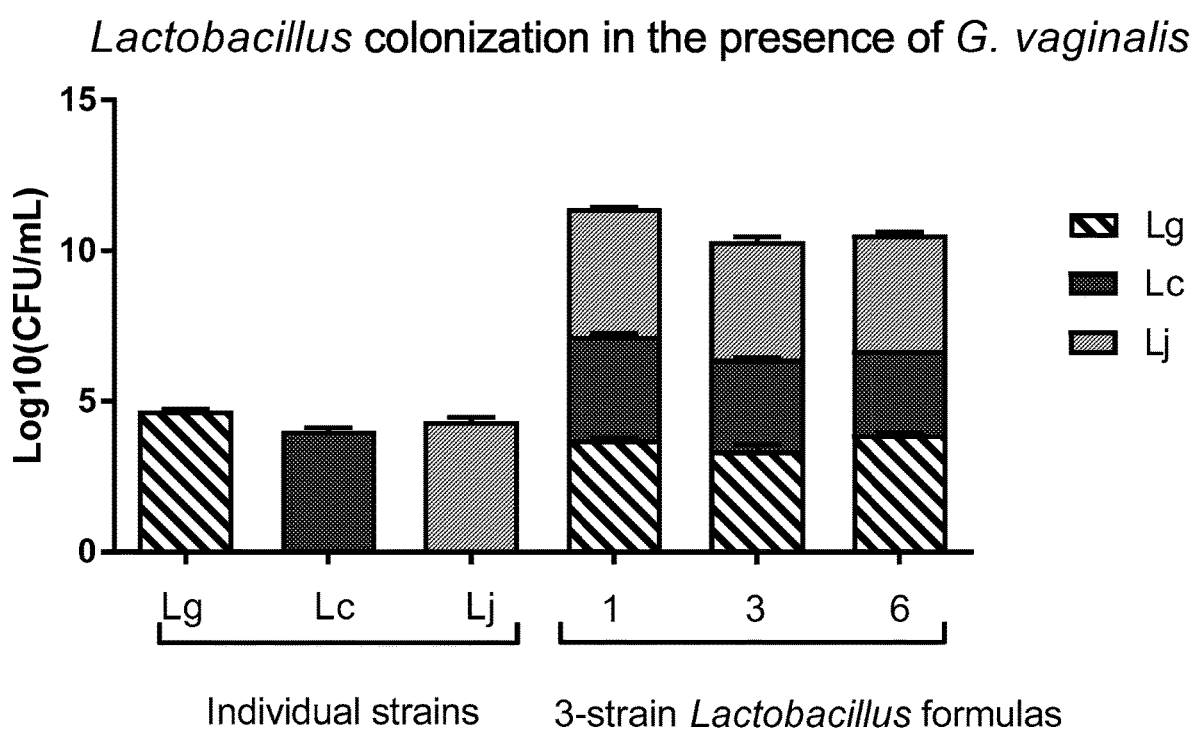
Figure 20:
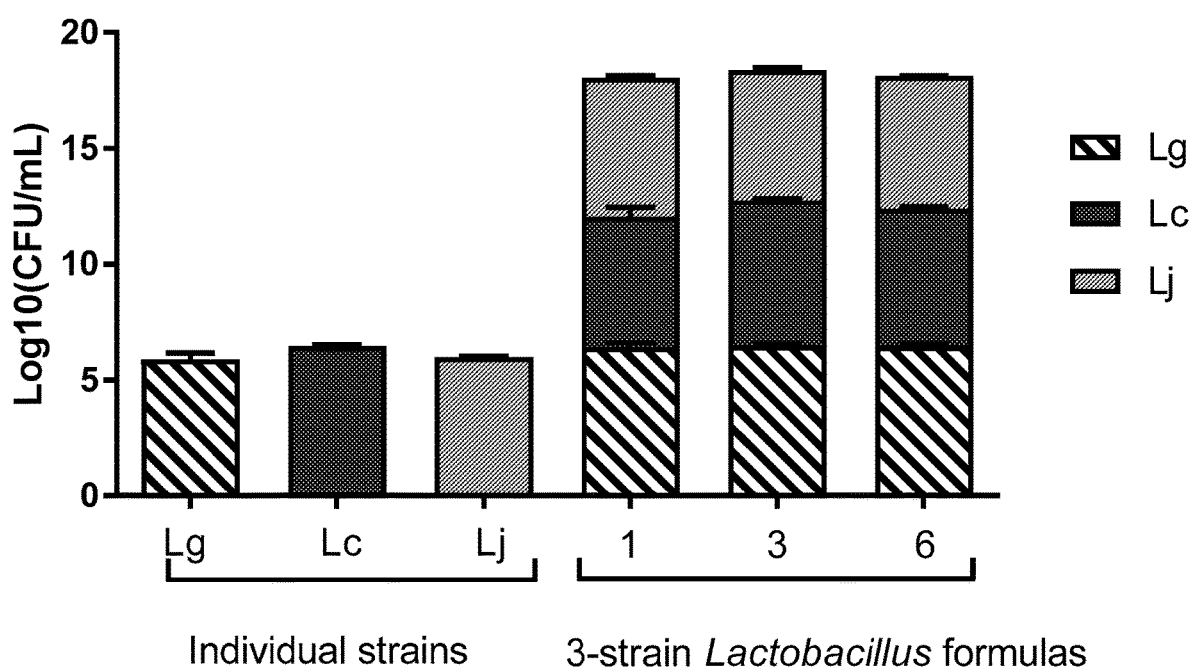
FIG. 20 shows reproducible colonization of bioengineered human cervicovaginal tissue (VEC100) by the three selected *Lactobacillus* strains (Lc=*L. crispatus* 223310, Lj=*L. jensenii* 2054210, and Lg=*L. gasseri* 29313) and an improved synergistic colonization by the 3-strain formulas indicated.
Figure 21:
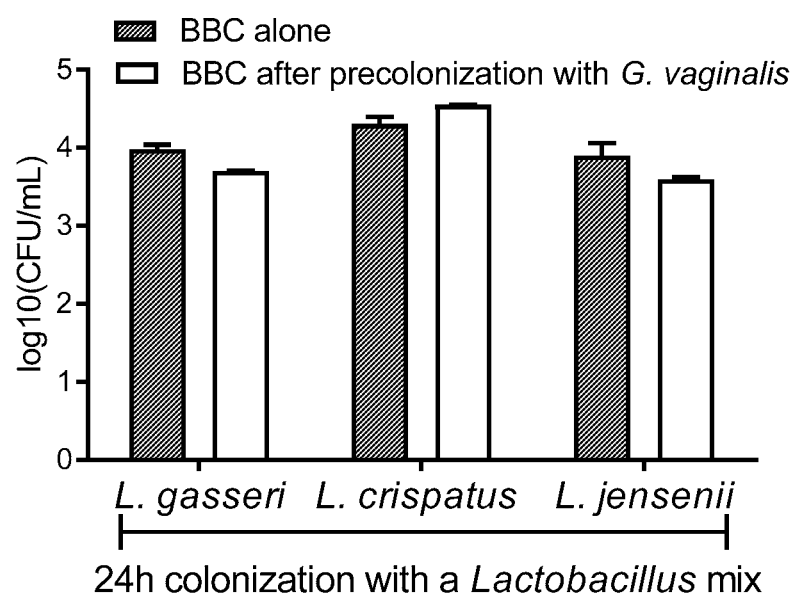
FIG. 21 shows the number of *L. crispatus*, *L. jensenii*, and *L. gasseri* CFU following colonization with BBC alone or with BBC following precolonization with *C. vaginalis*. Number of cells is assessed following 24 hour colonization with a *Lactobacillus* mixture.
Figure 22A:
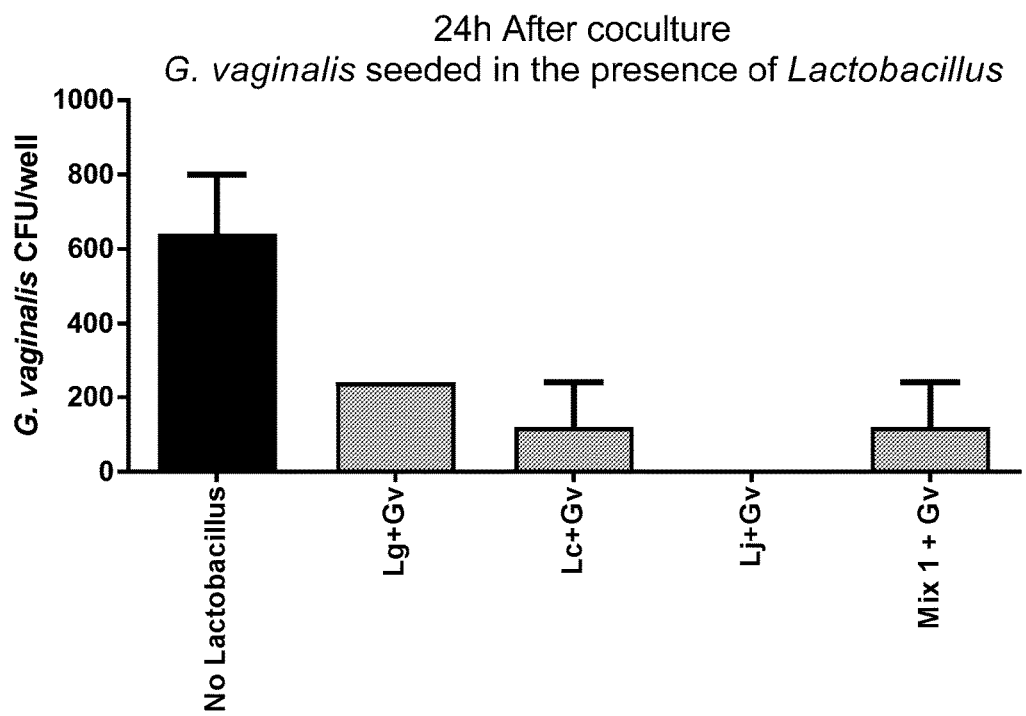
FIGS. 22A and 22B show the number of *G. vaginalis* CFU following colonization with the selected *Lactobacillus* strains alone or in mixes.
Figure 22B:
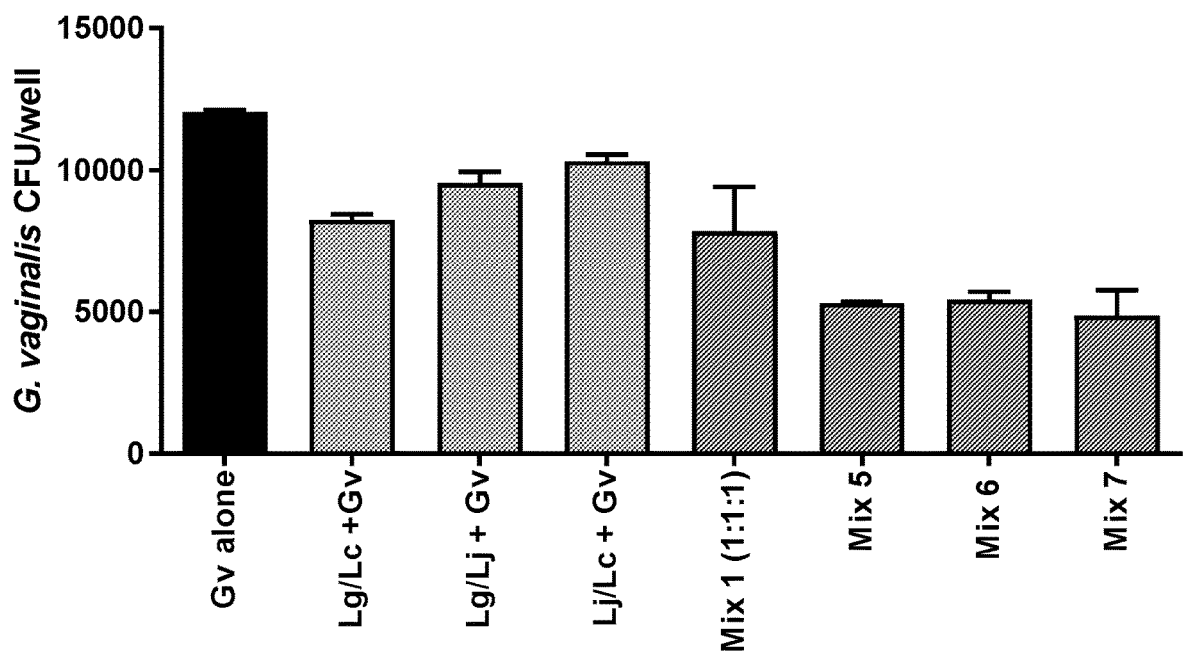
Figure 23A:
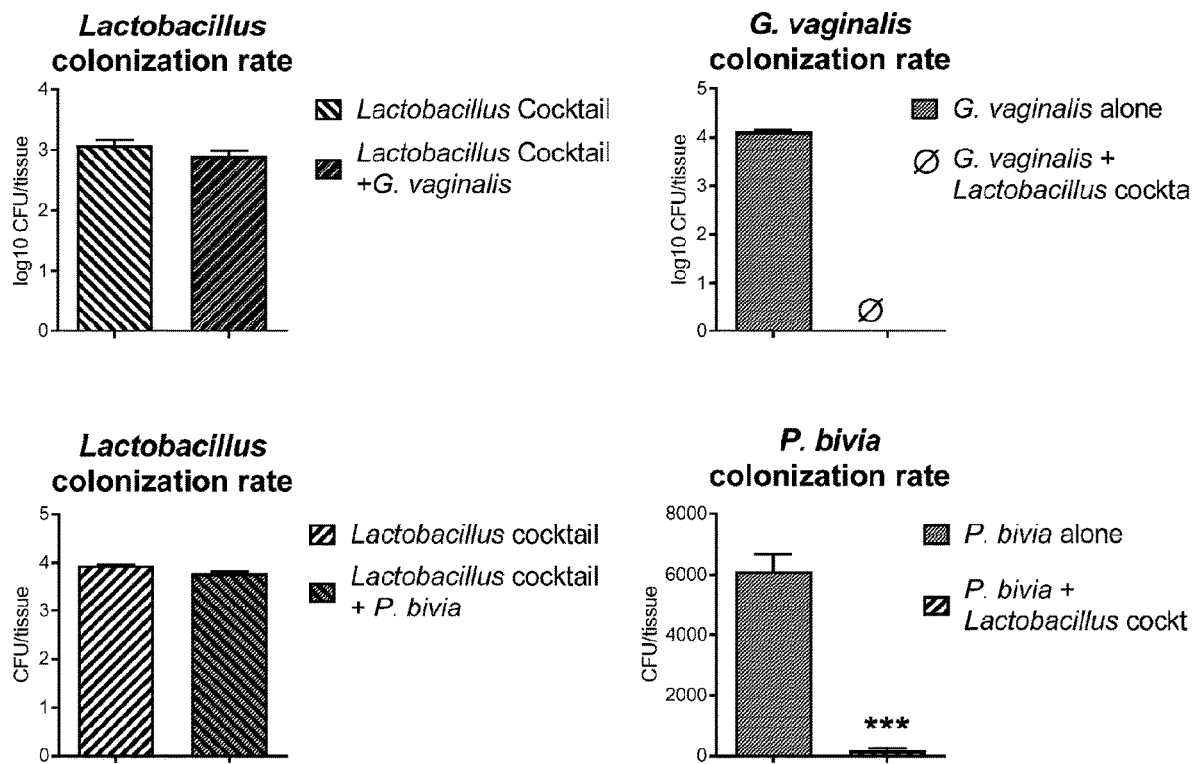
FIGS. 23A and 23B shows activities of a 3-strain cocktail against signature BV pathogens. The *Lactobacillus* mix maintained a reproducible colonization rate when applied to vaginal cells alone or when allowed to compete with equal numbers of *G. vaginalis* (iv) and *P. bivia* (Pb), isolated from women with BV (FIG. 23A, left panels). At the same time the BBC bacteria prevented Gv and Pb colonization (FIG. 23A, right panel) and suppressed the proinflammatory activities of both BV pathogens assessed by IL-8 levels (FIG. 23B). Total *Lactobacillus* CFU counts (*L. gasseri*, +*L. crispatus*+*L. jensenii*) are shown here for the cumulative colonization rates.
Figure 23B:
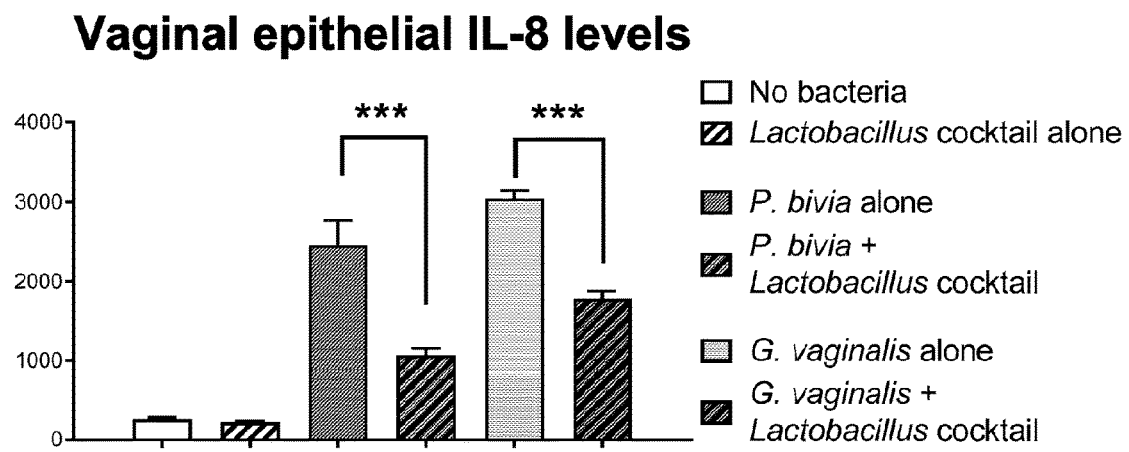
Figure 24:
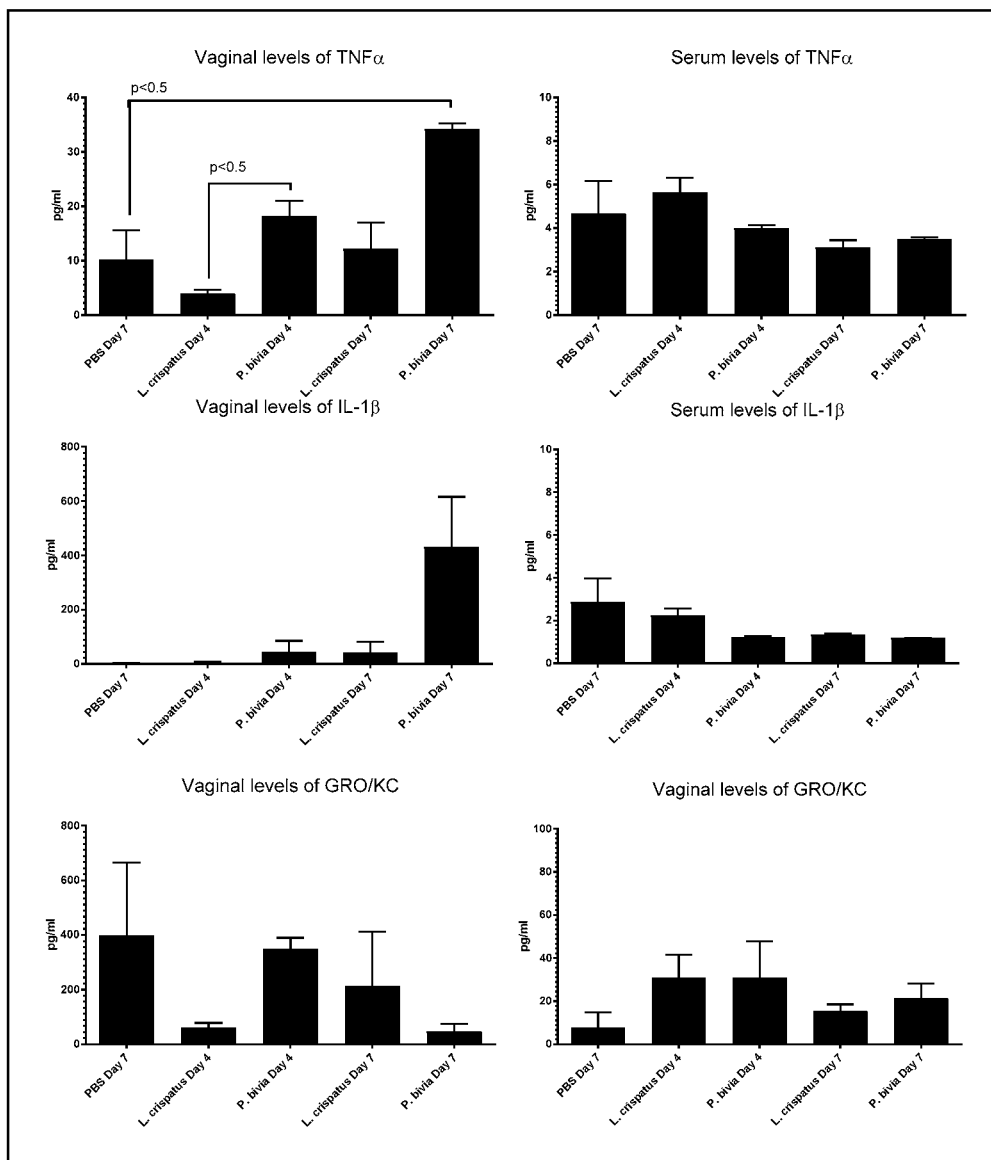
FIG. 24 shows cytokines and chemokines indicated measured in vaginal and serum samples from gnotobiotic mice exposed to beneficial bacteria (*L. crispatus*) and BV bacteria (*P. bivia*)

The species of strains identified was first confirmed by 16S-rRNA DNA sequencing on a selection of 43 bacterial isolates coming from a low risk healthy clinical environment. In addition, DNA deep sequencing library preparation of the three genomes and de novo genome assembly and Prokka annotation were completed. The molecular analysis confirmed species identity and identified unique features (FIGS. 14A-14C). Genome alignment of the three selected BBC strains and known genomes and BLASTN search identified that the three sequenced genomes are quite divergent from each other, sharing less than about 80% nucleotide sequence identity (FIG. 15). This is a highly desirable feature in that it supports the non-overlapping functional characteristic and functional genomics features as a basis of the strain synergisms. It is also desirable in there are many sites for strain/species-specific primers to allow PCR detection of the three strains in complex mixes in vivo, in animal safety and efficacy models and clinical trials. The functional properties of the chosen strains have been characterizes in a physiologic well-established in vitro model of the normal vaginal epithelium (FIGS. 13B-D, 16-22) and have obtained data from a gnotobiotic mouse model (FIG. 23). Endpoints of these observations were abilities of the strains to colonize the vaginal epithelial cells and to maintain a homeostatic immune environment. All three strains demonstrated stable and reproducible colonization by epithelial cells of the human female genital tract (FIG. 15A) without causing any epithelial damage (FIG. 15B). Gnotobiotic mouse model initially showed that no proinflammatory vaginal mucosal and systemic blood responses, measured by the major primary proinflammatory cytokines IL-1β and TNFα and the downstream effector chemokine GRO/KC, were induced by the selected strains applied vaginally by comparison of mock vaginal treatment, and vaginal inoculation of BV bacteria represented by the BV-signature bacterium *P. bivia* (FIG. 24). Findings in the in-vitro model indicated that none of the *Lactobacillus* isolates that were selected for the cocktail induce inflammation (FIG. 13B) and at the same time did not interfere significantly with the ability of the epithelial cells to respond to toll-like receptors stimulation by pathogen-associated patterns tested by classic tools e.g. synthetic ligands for TLR2/6 (mimic of bacterial lipoprotein) and TLR 3 (mimic of viral dsRNA) (FIG. 13B) Using novel methodology a formula that allows selection of the proportion of the three bacterial strains in a bacterial mix that allows a mutual support for growth and resistance to BV or activity against BV pathogens was established (FIGS. 17-23). The formula also allowed resistance to the microbiome perturbance caused by *Trichomonas vaginalis* (FIG. 18). The formula involves selection based on favorable growth (FIG. 17A-B) coupled with know-how to differentiate bacterial strains in a mix, and based on survival and steady colonization when seeded in a mix with BV pathogens (FIGS. 19A-19C) or following epithelial colonization by *G. vaginalis*, the microbe implicated in antibiotic-resistant BV biofilm formation[1] (FIG. 21). It was determined that the proportion of the bacteria in the cocktail matters for their survival in the epithelial cell context and have determined a few formulas of mixing the three selected BWH strains that yield an optimal proportion of colonization patterns (FIGS. 17A-17C). A synergistic colonization patter was observed resulting in a significantly higher *Lactobacillus* colonization rate achieved by the optimized 3-strain formulas as compared to the strains alone (FIG. 17B) and this phenomenon was confirmed in a bioengineered guman tissue mimicking the lower female human genital tract (FIG. 20) The same synergetic effect was observed when the bacterial mixes were applied to the vaginal epithelial cells in the presence of BV pathogens (FIGS. 19A-19C). We have determined that epithelial colonization by *G. vaginalis* is suppressed when *G. vaginalis* was introduced to the epithelial cells in a mix with our *Lactobacillus* strains (FIG. 22A). *G. vaginalis* was also suppressed by our selected cocktail mixes even when lactobacilli were added after the epithelial cells were pre-colonized with *G. vaginalis* indicating a potential for not only preventive but also therapeutic effects of the cocktail (FIG. 22B). An optimal 3-strain mix not only suppressed colonization by signature BV bacteria *G. vaginalis* and *P. bivia* (FIG. 22C) but also simultaneously mitigated associated inflammatory responses (FIG. 23).

The more favorable functional characteristic of the bacterial cocktail include: (1) comprises of isolates from healthy women at low risk of preterm delivery and prior to term delivery; (2) each strains demonstrates phenotypic and genetic proof of *Lactobacillus* species; (3) each strains is distinct from commercially available strains based on sequence analysis of data available in the public domain based on Prokka annotation; (4) in optimized formulas the cocktail of the three strains colonizes the vaginal epithelial cells in a reproducible fashion and outcompetes colonization by BV associated bacteria; (5) our initial results show homeostatic lack of local and systemic inflammatory activation in a gnotobiotic mouse model by comparison to mock treatment and colonization with BV bacteria (*P. bivia*); (6) vaginal epithelial cells colonized by these strains maintain the homeostatic balance of anti-inflammatory and proinflammatory mediators; and (7) in formulas the strains mitigated perturbances by BV pathogens and *Trichomonas vaginalis* but did not alter the ability of the vaginal epithelium to mount innate immune responses to pathogenic determinants.

Choice of Vaginal Delivery System

Figure 25A:
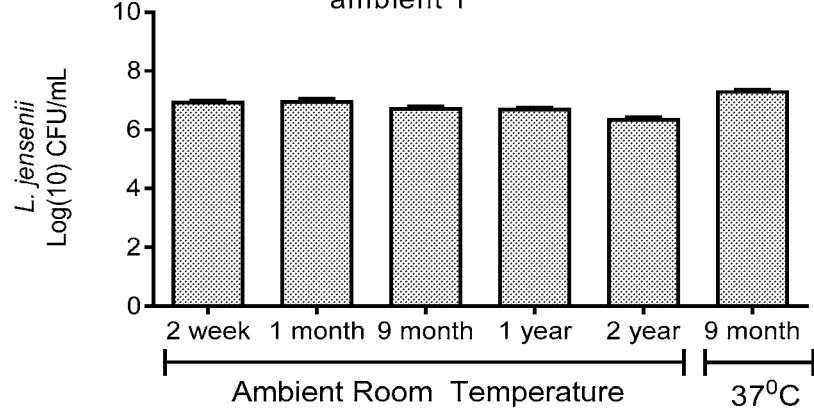
FIGS. 25A-25C show the stability of bacteria using preservation by vaporization (PBV).
Figure 25B:
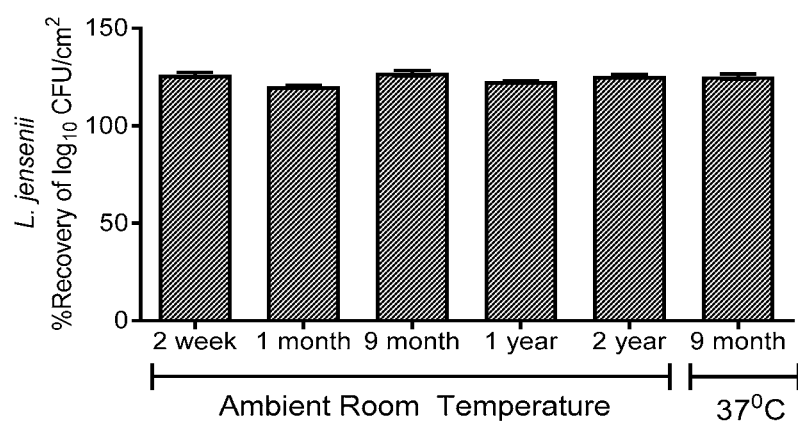
Figure 25C:
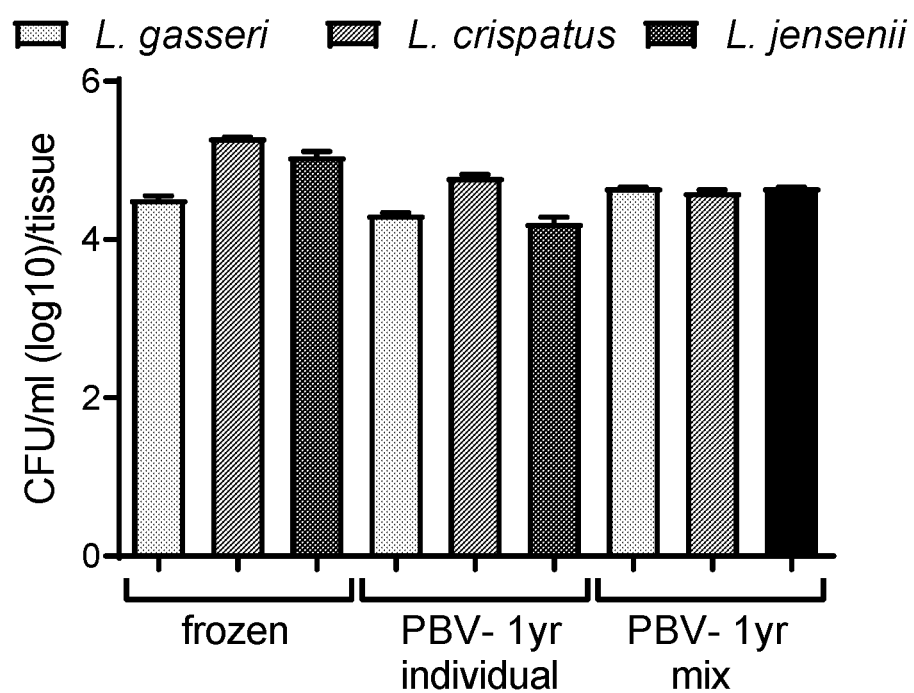

There are many potential types of formulations and delivery methods that can be used for the disclosed medicinal bacterial mix. These include vaginal tablets, capsules, suppository, creams, films and douches. In addition, preservation by evaporation (PBV) allows biologicals to be stable at higher temperatures for a prolonged period of time. It was demonstrated that PBV-preserved Lactobacilli can colonize the vaginal epithelium in a reproducible fashion and maintain this ability after long-term storage at RT and higher temperatures. A lack of toxicity was confirmed and proinflammatory activity of several placebo films and bacteria-loaded films and stability of the PBV bacteria maintained at RT for up to 2 years and 37° C. for up to 9 months (FIGS. 25A-25C).

All publications cited herein expressly incorporated herein by reference in their entireties.

REFERENCES FOR EXAMPLE 1

1. Onderdonk A B, Delaney M L, Fichorova R N. The Human Microbiome during Bacterial Vaginosis. Clin. Microbiol. Rev. Apr. 1, 2016 2016; 29(2):223-238.
2. Witkin S S. The vaginal microbiome, vaginal anti-microbial defence mechanisms and the clinical challenge of reducing infection-related preterm birth, BJOG: An International Journal of Obstetrics & Gynaecology. 2015:122(2):213-218.
3. Atashili J, Poole C. Ndumbe P M, Adimora A A, Smith J S. Bacterial vaginosis and HIV acquisition: a meta-analysis of published studies. AIDS, Jul. 31 2008; 22(12):1493-1501
4. Low A J, Konate I, Nagot N, et al. Cervicovaginal HIV-1 shedding in women taking antiretroviral therapy in Burkina Faso: a longitudinal study. Journal of acquired immune deficiency syndromes (1999). Feb. 1, 2014; 65(2):237-245.
5. Fichorova R N, Impact of *T. vaginalis* infection on innate immune responses and reproductive outcome, J. Reprod. Immunol. December 2009; 83(1-2):185-189.
6. Chang H H, Larson J, Blencowe H, et al. Preventing preterm births: analysis of trends and potential reductions with interventions in 39 countries with very high human development index. Lancet. Jan. 19, 2013; 381(9862):223-234.
7. Fichorova R N, Onderdonk A B, Yamamoto H. et al Maternal microbe-specific modulation of inflammatory response in extremely low-gestational-age newborns. mBio. 2011; 2(1):e00280-00210.
8. Fichorova R X, Beatty N, Sassi R R, et al. Systemic inflammation in the extremely low gestational age newborn following maternal genitourinary infections. Am. J. Reprod. Imnunol. February 2015; 73(2):162-174,
9. Lausten-honsen U, Olsen M, Greisen G, Selhmiegelow K. Inflammatory markers in umbilical cord blood from small-for-gestational-age newborns. Fetal and pediatric pathology. April 2014; 33(2):114-118.
10. McElrath T, Allred E N, Van Marter L, Fichorova R N. Leviton A, The ES1. Perinatal systemic inflammatory responses of growth-restricted preterm newborns. Acta paediatrica. Jul. 2, 2013.
11. O'Shea T M, Shah B, Allred E N, et al. Inflammation-initiating illnesses, inflammation-related proteins, and cognitive impairment in extremely preterm infants. Brain. Behav. Immun. March 2013; 29:104-112.
12. Leviton A, Fichorova R N, O'Shea T M, et al Two-hit model of brain damage in the very preterm newborn: small for gestational age and postnatal systemic inflammation. Pediatr. Res. March 2013; 73(3):362-370.
13. Bose C L, Laughon M M, Allred E N, et al. Systemic inflammation associated with mechanical ventilation among extremely preterm infants. Cytokine. January 2013; 61(1):315-322.
14. O'Shea T M, Allred E N, Kuban K C, et al. Elevated concentrations of inflammation-related proteins in postnatal blood predict severe developmental delay at 2 years of age in extremely preterm infants. J. Pediatr. March 2012; 160(3):395-401 e394.
15. Leviton A, Allred E N, Dammann O, et al. Systemic Inflammation, Intraventricular Hemorrhage, and White Matter injury. Journal of child neurology. Oct. 30, 2012.
16. McGrath M. Sullivan M. Birth weight, neonatal morbidities, and school age outcomes in full-term and preterm infants. Issues Compr Pediatr Nurs. October-December 2002; 25(4):231-254.
17. McGrath M M, Sullivan M, Devin J, et al. Early precursors of low attention and hyperactivity in a preterm sample at age four. Issues Compr Pediatr Nurs. January-March 2005; 28(1):1-15.
18. Sullivan M C, Hawes K, A decade comparison of preterm motor performance at age 4. Res Nurs Health, December 2007; 30(6):641-654.
19. Sullivan M C, Msall M E, Miller R J. 17-year outcome of preterm infants with diverse neonatal morbidities: Part 1—Impact on physical, neurological, and psychological health status. J Spec Pediatr Nurs. July 2012; 17(3):226-241.
20. Wu C S, Pedersen L H, Miller J E, et al. Risk of cerebral palsy and childhood epilepsy related to infections before or during pregnancy. PloS one. 2013; 8(2):e57552.
21. Miller J E, Pedersen L H, Streja E, et al. Maternal infections during pregnancy and cerebral palsy: a population-based cohort study. Paediatric and perinatal epidemiology. November 2013; 27(6):542-552.
22. Collier C H, Risnes K, Norwitz E R, Bracken M B, Illuzzi J L. Maternal infection in pregnancy and risk of asthma in offspring. Maternal and child health journal. December 2013; 17(10):1940-1950.
23. Brown A S Epidemiologic studies of exposure to prenatal infection and risk of schizophrenia and autism. Developmental neurobiology. October 2012; 72(10):1272-1276.
24. Khandaker G M, Zimbron J, Lewis G, Jones P B. Prenatal maternal infection, neurodevelopment and adult schizophrenia: a systematic review of population-based studies. Psychological medicine. February 2013; 43(2):239-257.
25. Sun Y, Christensen J, Olsen J. Childhood epilepsy and maternal antibodies to microbial and tissue antigens during pregnancy. Epilepsy research. November 2013; 107(1-2):61-74.
26. Camp B W, Broman S H, Nichols P L, Leff M. Maternal and neonatal risk factors for mental retardation: defining the 'at-risk' child. Early human development. Jan. 9, 1998; 50(2):159-173.
27. Leviton A, Allred E N, Kuban K C, et al. The Development of Extremely Preterm Infants Born to Women Who Had Genitourinary Infections During Pregnancy. Am. J. Epidemiol. Jan. 1, 2016; 183(1):28-35.
28. Leviton A. Allred E N, Fichorova R N, et al. Antecedents of inflammation biomarkers in preterm newborns on days 21 and 28. Acta Paediatr. March 2016; 105(3):274-280.
29. Leviton A, Allred E N, Fichorova R N, et al. Systemic inflammation on postnatal days 21 and 28 and indicators 29. ... of brain dysfunction 2 years later among children born before the 28th week of gestation. Early Hum. Dev. February 2016; 93:25-32.
30. Dammann O, Allred E N, Fichorova R N, et al. Duration of Systemic Inflammation in the First Postnatal Month Among Infants Born Before the 28th Week of Gestation. Inflammation. April 2016; 39(2):672-677.
31. Kuban K C, O'Shea T M, Allred E N, et al. The breadth and type of systemic inflammation and the risk of adverse neurological outcomes in extremely low gestation newborns. Pediatr. Neurol. January 2015; 52(1):42-48.
32. Korzeniewski S J, Allred E, Logan J W, et al. Elevated endogenous erythropoietin concentrations are associated with increased risk of brain damage in extremely preterm neonates. PloS one. 2015; 10(3):e0115083.
33. O'Shea T M, Joseph R M, Kuban K C, et al. Elevated blood levels of inflammation-related proteins are associated with an attention problem at age 24 mo in extremely preterm infants. Pediatr. Res. June 2014; 75(6):781-787.
34. Kuban K C, O'Shea T M, Allred E N, et al Systemic Inflammation and Cerebral Palsy Risk in Extremely Preterm Infants. J. Child Neurol. Mar. 18, 2014.
35. Korzeniewski S J Soto-Rivera C L, Fichorova R N, et al. Are preterm newborns who have relative hvperthyrotropinemia at increased risk of brain damage?J. Pediatr. Endocrinol. Metab. Nov. 1, 2014; 27(11-12):1077-1088.
36. McElrath T F, Allred E N, Van Marter L, Fichorova R N, Leviton A, Investigators E S. Perinatal systemic inflammatory responses of growth-restricted preterm newborns. Acta Paediatr. October 2013; 102(10):e439-442.
37. Martin C R, Bellomy M, Allred E N, Fichorova R N, Leviton A. Systemic inflammation associated with severe intestinal injury in extremely low gestational age newborns. Fetal Pediatr Pathol. Sep. 24, 2013; 32(3):222-234.
38. Leviton A, Allred E N, Dammann O, et al. Systemic inflammation, intraventricular hemorrhage, and white matter injury. J. Child Neurol. December 2013; 28(12):1637-1645.
39. Trivedi S. Joachim M, McElrath T, et al. Fetal-placental inflammation, but not adrenal activation, is associated with extreme preterm delivery. Am. J. Obstet. Gynecol. March 2012; 206(3):236 e231-238.
40. Leviton A. O'Shea T M, Bednarck F J, et al. Systemic responses of preterm newborns with presumed or documented bacteracmia. Act Pacdiatr. April 2012; 101(4):355-359.
41. McElrath T F, Fichorova R N, Allred E N, et al. Blood protein profiles of infants born before 28 weeks differ by pregnancy complication. Am. J. Obstet. Gynecol. May 2011; 204(5):418 e411-418 e412.
42. Leviton A. Kuban K C, Allred E N, et al. Early postnatal blood concentrations of inflammation-related proteins and microcephaly two years later in infants born before the 28th post-menstrual week. Early Hum. Dev. May 2011; 87(5):325-330.
43. Leviton A, Kuban K, O'Shea T M, et al. The relationship between early concentrations of 25 blood proteins and cerebral white matter injury in preterm newborns: the ELGAN study. J. Pediatr. June 2011; 158(6):897-903 e891-895.
44. Leviton A, Kuban K, Allred E, Fichorova R, O'Shea T, Paneth N. Preterm infants' early blood protein concentrations predict later microcephaly. Ann. Neurol. 2011; in press.
45. Leviton A, Hecht J L, Allred E N, Yamamoto H, Fichorova R N, Dammann O. Persistence after birth of systemic inflammation associated with umbilical cord inflammation. J. Reprod. Immunol. August 2011; 90(2):235-243.
46. Leviton A, Fichorova R, Yamamoto Y, et al. Inflammation-related proteins in the blood of extremely low gestational age newborns. The contribution of inflammation to the appearance of developmental regulation. Cytokine. January 2011; 53(1):66-73.
47. Leviton A, Allred E N, Kuban K C, et al. Blood protein concentrations in the first two postnatal weeks associated with early postnatal blood gas derangements among infants born before the 28th week of gestation. The ELGAN Study. Cytokine. November 2011; 56(2):392-398.
48. Hecht J L, Fichorova R N, Tang V F, Allred E N, McElrath T F, Leviton A. The relationship between neonatal blood protein profiles and placenta histologic characteristics in extremely low gestation age newborns. Pediatr. Res. Oct. 1, 2011; 69:68-73.
49. Fichorova R N, Onderdonk A B, Yamamoto H, et al. Maternal microbe-specific modulation of inflammatory response in extremely low-gestational-age newborns. mBio. 2011; 2(1):e00280-00210.
50. Bose C, Laughon M, Allred E N, et al. Blood protein concentrations in the first two postnatal weeks that predict bronchopulmonary dysplasia among infants born before the 28th week of gestation. Pediatr. Res. April 2011; 69(4):347-353.
51. Anahtar M N, Byrne E H, Doherty K E, et al. Cervicovaginal bacteria are a major modulator of host inflammatory responses in the female genital tract. Immunity. May 19, 2015; 42(5):965-976.
52. Fichorova R N, Tucker L D, Anderson D J. The molecular basis of nonoxynol-9-induced vaginal inflammation and its possible relevance to human immunodeficiency virus type 1 transmission. J. Infect. Dis. Aug. 15, 2001; 184(4):418-428.
53. Kyongo J K, Crucitti T, Menten J, et al. Cross-Sectional Analysis of Selected Genital Tract Immunological Markers and Molecular Vaginal Microbiota in Sub-Saharan African Women, with Relevance to HIV Risk and Prevention. Clinical and vaccine immunology: CVI. May 2015; 22(5):526-538.
54. Kyongo J K, Crucitti T, Menten J et al. Genital Tract Immunological Markers in Sub-Saharan African Women with Relevance to HIV Risk and Prevention. AIDS Res. Hum. Retroviruses. October 2014; 30 Suppl 1:A233.
55. Kyongo J K, Jespers V, Goovaerts O, et al. Searching for lower female genital tract soluble and cellular biomarkers: defining levels and predictors in a cohort of healthy caucasian women. PloS one. 20127(8):e43951.
56. Fichorova R N, Yamamoto H S, Delaney M L, Onderdonk A B, Doncel G F. Novel vaginal microflora colonization model providing new insight into microbicide mechanism of action. mBio. 2011; 2:6. e00168-00111.
57. Ravel J, Gajer P, Fu L, et al. Twice-daily application of HIV microbicides alter the vaginal microbiota, mBio. 2012; 3(6).

ADDITIONAL REFERENCES FOUND WITHIN SPECIFICATION

ADAMS, M., LI, Y., KHOT, H., DE KOCK, C., SMITH, P. J., LAND, K., CHIBALE, K. & SMITH, G. S. 2013. The synthesis and antiparasitic activity of aryl- and ferrocenyl-derived thiosemicarbazone ruthenium(II)-arene complexes. *Dalton Trans,* 42, 4677-85.

BUVE, A., JESPERS, V., CRUCITTI, T. & FICHOROVA, R. N. 2014. The vaginal microbiota and susceptibility to HIV. *AIDS*, 28, 2333-44.

DONCEL, G. F., CHANDRA, N. & FICHOROVA, R. N. 2004. Preclinical assessment of the proinflammatory potential of microbicide candidates. *J Acquir Immune Defic Syndr*, 37 Suppl 3, S174-80.

DORNBUSH, P. J., VAZQUEZ-ANAYA, G., SHOKAR, A., BENSON, S., RAPP, M., WNUK, S. F., WRISCHNIK, L. A. & LAND, K. M. 2010. AdoHcy hydrolase of *Trichomonas vaginalis*: studies of the effects of 5'-modified adenosine analogues and related 6-N-cyclopropyl derivatives. *Bioorg Med Chem Lett*, 20, 7466-8.

FICHOROVA, R. N. 2004. Guiding the vaginal microbicide trials with biomarkers of inflammation. *J Acquir Immune Defic Syndr*, 37 Suppl 3, S184-93.

FICHOROVA, R. N., BAJPAI, M., CHANDRA, N., HSIU, J. G., SPANGLER, M., RATNAM, V. & DONCEL, G. F. 2004. Interleukin (IL)-1, IL-6, and IL-8 predict mucosal toxicity of vaginal microbicidal contraceptives. *Biol Reprod*, 71, 761-9.

FICHOROVA, R. N., YAMAMOTO, H. S., DELANEY, M. L., ONDERDONK, A. B. & DONCEL, G. F. 2011. Novel vaginal microflora colonization model providing new insight into microbicide mechanism of action. *MBio*, 2, e00168-11.

HUPPERT, J. S., HUANG, B., CHEN, C., DAWOOD, H. Y. & FICHOROVA, R. N. 2013. Clinical evidence for the role of *Trichomonas vaginalis* in regulation of secretory leukocyte protease inhibitor in the female genital tract. *J Infect Dis*, 207, 1462-70.

KLEBANOFF, S. J. & COOMBS, R. W. 1991. Viricidal effect of *Lactobacillus acidophilus* on human immunodeficiency virus type 1: possible role in heterosexual transmission. *The Journal of Experimental Medicine*, 174, 289-292.

ONDERDONK, A. B., DELANEY, M. L. & FICHOROVA, R. N. 2016. The Human Microbiome during Bacterial Vaginosis. *Clin Microbiol Rev*, 29, 223-38.

ONDERDONK, A. B., ZAMARCHI, G. R., RODRIGUEZ, M. L., HIRSCH, M. L., MUNOZ, A. & KASS, E. H. 1987. Qualitative assessment of vaginal microflora during use of tampons of various compositions. *Appl Environ Microbiol*, 53, 2779-84.

RAJA, R., NAYAK, A. K., SHUKLA, A. K., RAO, K. S., GAUTAM, P., LAL, B., TRIPATHI, R., SHAHID, M., PANDA, B. B., KUMAR, A., BHATTACHARYYA, P., BARDHAN, G., GUPTA, S. & PATRA, D. K. 2015. Impairment of soil health due to fly ash-fugitive dust deposition from coal-fired thermal power plants. *Environ Monit Assess*, 187, 679.

SHOKAR, A., AU, A., AN, S. H., TONG, E., GARZA, G., ZAYAS, J., WNUK, S. F. & LAND, K. M. 2012. S-Adenosylhomocysteine hydrolase of the protozoan parasite *Trichomonas vaginalis*: potent inhibitory activity of 9-(2-deoxy-2-fluoro-beta,D-arabinofuranosyl)adenine. *Bioorg Med Chem Lett*, 22, 4203-5.

YAMAMOTO, H. S., XU, Q. & FICHOROVA, R. N. 2013. Homeostatic properties of Lactobacillusjensenii engineered as a live vaginal anti-HIV microbicide. *BMC Microbiol*, 13, 4.

Sequence Listing
(SEQ ID NO: 1):
TGCAGTCGAGCGAGCGGAACTAACAGATTTACTTCGGTAATGACGTTAGG

AAAGCGAGCGGCGGATGGGTGAGTAACACGTGGGGAACCTGCCCCATAGT

CTGGGATACCACTTGGAAACAGGTGCTAATACCGGATAAGAAAGCAgATC

GCATGATCAGCTTTTAAAAGGCGGCGTAAGCTGTCGCTATGGGATGGCCC

CGCGGTGCATTAGCTAGTTGGTAAGGTAAAGGCTTACCAAGGCGATGATG

CATAGCCgAgtTGAGAGACTGATCGGCCACATTGGGACTGAGACACGGCC

CAAACTCCTACGGGAGGCAGCAGTAGGGAATCTTCCACAATGGACGCAAG

TCTGATGGAGCAACGCCGCGTGAGTGAAGAAGGTTTTCGGATCGTAAAGC

TCTGTTGTTGGTGAAGAAGGATAGAGGTAGTAACTGGCCTTTATTTGACG

GTAATCAACCAGAAAGTCACGGCTAACT (SEQ ID NO: 2):
CGTCAATAAAGGCCAGTTACTACCTCTATCCTTCTTCACCAACAACAGAG

CTTTACGATCCGAAAACCTTCTTCACTCACGCGGCGTTGCTCCATCAGAC

TTGCGTCCATTGTGGAAGATTCCCTACTGCTGCCTCCCGTAGGAGTTTGG

GCCGTGTCTCAGTCCCAATGTGGCCGATCAGTCTCTCAACTCGGCTATGC

ATCATCGCCTTGGTAAGCCTTTACCTTACCAACTAGCTAATGCACCGCGG

GGCCATCCCATAGCGACAGCTTACGCCGCCTTTTAAAAGCTGATCATGCG

ATCTGCTTTCTTATCCGGTATTAGCACCTGTTTCCAAGTGGTATCCCAGA

CTATGGGGCAGGTTCCCCACGTGTTACTCACCCATCCGCCGCTCGCTTTC

CTAACGTCATTACCGAAGTAAATCTGTTAGTTCCGCTCGCTCGACTTGCA

TGTATTAGGCACGCCGCCAGCGTTC (SEQ ID NO: 3):
TGCAGTCGAGCGAGCTTGCCTATTGAAATTCTTCGGAATGGACATAGATA

CAAGCTAGCGGCGGATGGGTGAGTAACGCGTGGGTAACCTGCCCTTAAGT

CTGGGATACCATTTGGAAACAGATGCTAATACCGGATAAAAGCTACTTTC

GCATGAAAGAAGTTTAAAAGGCGGCGTAAGCTGTCGCTAAAGGATGGACC

TGCGATGCATTAGCTAGTTGGTAAGGTAACGGCTTACCAAGGCGATGATG

CATAGCCGAGTTGAGAGACTGATCGGCCACATTGGGACTGAGACACGGCC

CAAACTCCTACGGGAGGCAGCAGTAGGGAATCTTCCACAATGGACGCAAG

TCTGATGGAGCAACGCCGCGTGAGTGAAGAAGGTTTTCGGATCGTAAAGC

TCTGTTGTTGGTGAAGAAGGATAGAGGTAGTAACTGGCCTTTATTTGACG

GTAATCAACCAGAAAGTCACGGCTAACTACG (SEQ ID NO: 4):
CGTCAATAAAGGCCAGTTACTACCTCTATCCTTCTTCACCAACAACAGAG

CTTTACGATCCGAAAACCTTCTTCACTCACGCGGCGTTGCTCCATCAGAC

TTGCGTCCATTGTGGAAGATTCCCTACTGCTGCCTCCCGTAGGAGTTTGG

GCCGTGTCTCAGTCCCAATGTGGCCGATCAGTCTCTCAACTCGGCTATGC

ATCATCGCCTTGGTAAGCCGTTACCTTACCAACTAGCTAATGCATCGCAG

GTCCATCCTTTAGCGACAGCTTACGCCGCCTTTTAAACTTCTTTCATGCG

AAAGTAGCTTTTATCCGGTATTAGCATCTGTTTCCAAATGGTATCCCAGA

CTTAAGGGCAGGTTACCCACGCGTTACTCACCCATCCGCCGCTAGCTTGT

ATCTATGTCCATTCCGAAGAATTTCAATAGGCAAGCTCGCTCGACTTGCA

TGTATTAGGCACGCCGCCAGCGTTC (SEQ ID NO: 5):
TGCAGTCGAGCGAGCTTGCCTAGATGAATTTGGTGCTTGCACCAaATGAA
ACTAGATACAAGCGAGCGGCGGACGGGTGAGTAACACGTGGGTAACCTGC
CCAAGAGACTGGGATAACACCTGGAAACAGATGCTAATACCGGATAACAA
CACTAGACGCATGTCTAGAGTTTAAAAGATGGTTCTGCTATCACTCTTGG
ATGGACCTGCGGTGCATTAGCTAGTTGGTAAGGCAACGGCTTACCAAGGC
AATGATGCATAGCCGAGTTGAGAGACTGATCGGCCACATTGGGACTGAGA
CACGGCCCAAACTCCTACGGGAGGCAGCAGTAGGGAATCTTCCACAATGG
ACaCAAGTCTGATGGAGCAACGCCGCGTGAGTGAAGAAGGGTTTCGGCTC
GTAAAGCTCTGTTGGTAGTGAAGAAAGATAGAGGTAGTAACTGGCCTTTA
TTTGACGGTAATTACTTAGAAAGTCACGGCTAACTACGTGCC (SEQ ID NO: 6):
TATTACCGTCAATAAAGGCCAGTTACTACCTCTATCTTTCTTCACTACCA
ACAGAGCTTTACGAGCCGAAACCCTTCTTCACTCACGCGGCGTTGCTCCA
TCAGACTTGCGTCCATTGTGGAAGATTCCCTACTGCTGCCTCCCGTAGGA
GTTTGGGCCGTGTCTCAGTCCCAATGTGGCCGATCAGTCTCTCAACTCGG
CTATGCATCATTGCCTTGGTAAGCCGTTGCCTTACCAACTAGCTAATGCA
CCGCAGGTCCATCCAAGAGTGATAGCAGAACCATCTTTTAAACTCTAGAC
ATGCGTCTAGTGTTGTTATCCGGTATTAGCATCTGTTTCCAGGTGTTATC
CCAGTCTCTTGGGCAGGTTACCCACGTGTTACTCACCCGTCCGCCGCTCG
CTTGTATCTAGTTTCATtTGGTGCAAGCACCAAATTCATCTAGGCAAGCT
CGCTCGACTTGCATGTATTAGGCACGCCGCCAGCGTTCG

```
APPENDIX A
16S rRNA gene sequences of strains that failed the selection
algorithm
Primer sequences
1) 27F:
                                                         (SEQ ID NO: 49)
AGA GTT TGA TCM TGG CTC AG 2) 1492R:
                                                         (SEQ ID NO: 50)
CGG TTA CCT TGT TAC GAC TT 3) 529R:
                                                         (SEQ ID NO: 51)
CGC GGC TGC TGG CAC L. jensenii BWH #24624
27F
                                                         (SEQ ID NO: 7)
```
TGCAGTCGAGCGAGCTTGCCTATAGAAATTCTTCGGAATGGACATAGATACAAGCTA
GCGGCGGATGGGTGAGTAACGCGTGGGTAACCTGCCCTTAAGTCTGGGATACCATTT
GGAAACAGATGCTAATACCGGATAAAAGCTACTTTCGCATGAAAGAAGTTTAAAAG
GCGGCGTAAGCTGTCGCTAAAGGATGGACCTGCGATGCATTAGCTAGTTGGTAAGG
TAACGGCTTACCAAGGCGATGATGCATAGCCGAGTTGAGAGACTGATCGGCCACAT
TGGGACTGAGACACGGCCCAAACTCCTACGGGAGGCAGCAGTAGGGAATCTTCCAC
AATGGACGAAAGTCTGATGGAGCAACGCCGCGTGAGTGAAGAAGGTTTTCGGATCG
TAAAGCTCTGTTGTTGGTGAAGAAGGATAGAGGTAGTAACTGGCCTTTATTTGACGG
TAATCAACCAGAAAGTCACGGCTAACTACGTGCC 529R
                                                         (SEQ ID NO: 8)
CGTCaATAAAGGCCAGTTACTACCTCTATCCTTCTTCACCAACAACAGAGCTTTACGA
TCCGAAAACCTTCTTCACTCACGCGGCGTTGCTCCATCAGACTTTCGTCCATTGTGGA
AGATTCCCTACTGCTGCCTCCCGTAGGAGTTTGGGCCGTGTCTCAGTCCCAATGTGG
CCGATCAGTCTCTCAACTCGGCTATGCATCATCGCCTTGGTAAGCCGTTACCTTACC
AACTAGCTAATGCATCGCAGGTCCATCCTTTAGCGACAGCTTACGCCGCCTTTTAAA
CTTCTTTCATGCGAAAGTAGCTTTTATCCGGTATTAGCATCTGTTTCCAAATGGTATC
CCAGACTTAAGGGCAGGTTACCCACGCGTTACTCACCCATCCGCCGCTAGCTTGTAT
CTATGTCCATTCCGAAGAATTTCTATAGGCAAGCTCGCTCGACTTGCATGTATTAGG
CACGCCGCCAGCGTTC

*L. jensenii* BWH #564113
27F (SEQ ID NO: 9)
TGCAGTCGAGCGAGCTTGCCTATTGAAATTCTTCGGAATGGACATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACGGCTTACCAAGGCGATGATGCATAGCCGAGTTGAGAGACTGATCGGCCACAT

TGGGACTGAGACACGGCCCAAACTCCTACGGGAGGCAGCAGTAGGGAATCTTCCAC

AATGGACGCAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTAC

529R (SEQ ID NO: 10)
CGTCAATAAAGGCCAGTTACTACCTCTATCCTTCTTCACCAACAACAGAGCTTTACG

ATCCGAAAACCTTCTTCACTCACGCGGCGTTGCTCCATCAGACTTGCGTCCATTGTG

GAAGATTCCCTACTGCTGCCTCCCGTAGGAGTTTGGGCCGTGTCTCAGTCCCAATGT

GGCCGATCAGTCTCTCAACTCGGCTATGCATCATCGCCTTGGTAAGCCGTTACCTTA

CCAACTAGCTAATGCATCGCAGGTCCATCCTTTAGCGACAGCTTACGCCGCCTTTTA

AACTTCTTTCATGCGAAAGTAGCTTTTATCCGGTATTAGCATCTGTTTCCAAATGGTA

TCCCAGACTTAAGGGCAGGTTACCCACGCGTTACTCACCCATCCGCCGCTAGCTTGT

ATCTATGTCCATTCCGAAGAATTTCAATAGGCAAGCTCGCTCGACTTGCATGTATTA

GGCACGCCGCCAGCGTTC

*L. jensenii* BWH #1768213
27F (SEQ ID NO: 11)
TGCAGTCGAGCGAGCTTGCCTATTGAAATTCTTCGGAATGGACATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACGGCTTACCAAGGCGATGATGCATAGCCGAGTTGAGAGACTGATCGGCCACAT

TGGGACTGAGACACGGCCCAAACTCCTACGGGAGGCAGCAGTAGGGAATCTTCCAC

AATGGACGCAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTACGTGCCA

529R (SEQ ID NO: 12)
CGTCAATAAAGGCCAGTTACTACCTCTATCCTTCTTCACCAACAACAGAGCTTTACG

ATCCGAAAACCTTCTTCACTCACGCGGCGTTGCTCCATCAGACTTGCGTCCATTGTG

GAAGATTCCCTACTGCTGCCTCCCGTAGGAGTTTGGGCCGTGTCTCAGTCCCAATGT

GGCCGATCAGTCTCTCAACTCGGCTATGCATCATCGCCTTGGTAAGCCGTTACCTTA

CCAACTAGCTAATGCATCGCAGGTCCATCCTTTAGCGACAGCTTACGCCGCCTTTTA

AACTTCTTTCATGCGAAAGTAGCTTTTATCCGGTATTAGCATCTGTTTCCAAATGGTA

-continued

TCCCAGACTTAAGGGCAGGTTACCCACGCGTTACTCACCCATCCGCCGCTAGCTTGT

ATCTATGTCCATTCCGAAGAATTTCAATAGGCAAGCTCGCTCGACTTGCATGTATTA

GGCACGCCGCCAGCGTT

L. jensenii BWH #1949112
27F
(SEQ ID NO: 13)
CGAgCTTGcCTATAtaAtTTCTTCtGAATGGACaTaaTaCAAgCTAGCGGCGGATGGGTGA GTAACGCGTGaGTAACCTGcCCTTAAGTcGGGgATACCATTTGGAAACagATGCTAATA CCgGATAAAAGCTACTTTCcCATGAAAGAAgTTTAAAAGGCGGtgtAAgCTGtCgCTAAa gGATGGACCTGCGATGCATTAGCTAgtTGGTAAGGTAACGGCTTAcCaAGGcgATGATG CaTAcCCGAgTTGA 529R
(SEQ ID NO: 14)
CTTTACgAtCCgAAagccTTCTTCACTCACGCGGCGTgGCTCCATCagacttgcgcCCAT-
TGTG gAAGAtTCCCTACTGCTGCCTCCCGTAGGAGTtTGGgCCGTGTCTCAgTCCCAATGTGG CCGATCAGTCTCTCAaATCGGCTATGCATCATCGCCTTGGTAAGCCGTTACCTTACCA ACTAGCTAATGCATCGcAGGTCCATCCtatAGCGAcAGcTtAcgCCGtCTTTtAAACTTCTT TCATGcGaatgTAGcTTTTATgCgGTATTAGCATCTGTTTCCAAATGGtATCCCAGACTTA aGGGcAGGTTAcCtacGCGTTACTCACCCaTCCGCCGCT L. jensenii BWH #22448
27F
(SEQ ID NO: 15)
TGCAGTCGAGCGAGCTTGCCTATTGAAATTCTTCGGAATGGACATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACGGCTTACCAAGGCGATGATGCATAGCCGAGTTGAGAGACTGATCGGCCACAT

TGGGACTGAGACACGGCCCAAACTCCTACGGGAGGCAGCAGTAGGGAATCTTCCAC

AATGGACGCAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTAC 529R
(SEQ ID NO: 16)
CGTCAATAAAGGCCAGTTACTACCTCTATCCTTCTTCACCAACAACAGAGCTTTACG

ATCCGAAAACCTTCTTCACTCACGCGGCGTTGCTCCATCAGACTTGCGTCCATTGTG

GAAGATTCCCTACTGCTGCCTCCCGTAGGAGTTTGGGCCGTGTCTCAGTCCCAATGT

GGCCGATCAGTCTCTCAACTCGGCTATGCATCATCGCCTTGGTAAGCCGTTACCTTA

CCAACTAGCTAATGCATCGCAGGTCCATCCTTTAGCGACAGCTTACGCCGCCTTTTA

AACTTCTTTCATGCGAAAGTAGCTTTTATCCGGTATTAGCATCTGTTTCCAAATGGTA

TCCCAGACTTAAGGGCAGGTTACCCACGCGTTACTCACCCATCCGCCGCTAGCTTGT

ATCTATGTCCATTCCGAAGAATTTCAATAGGCAAGCTCGCTCGACTTGCATGTATTA

GGCACGCCGCCAGCGTTC

*L. jensenii* BWH #22410
27F (SEQ ID NO: 17)

TGCAGTCGAGCGAGCTTGCCTATTGAAATTCTTCGGAATGGACATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACGGCTTACCAAGGCGATGATGCATAGCCGAGTTGAGAGACTGATCGGCCACAT

TGGGACTGAGACACGGCCCAAACTCCTACGGGAGGCAGCAGTAGGGAATCTTCCAC

AATGGACGCAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTACGTGCCAG

529R (SEQ ID NO: 18)

CGTCaATAAAGGCCAGTTACTACCTCTATCCTTCTTCACCAACAACAGAGCTTTACGA

TCCGAAAACCTTCTTCACTCACGCGGCGTTGCTCCATCAGACTTGCGTCCATTGTGG

AAGATTCCCTACTGCTGCCTCCCGTAGGAGTTTGGGCCGTGTCTCAGTCCCAATGTG

GCCGATCAGTCTCTCAACTCGGCTATGCATCATCGCCTTGGTAAGCCGTTACCTTAC

CAACTAGCTAATGCATCGCAGGTCCATCCTTTAGCGACAGCTTACGCCGCCTTTTAA

ACTTCTTTCATGCGAAAGTAGCTTTTATCCGGTATTAGCATCTGTTTCCAAATGGTAT

CCCAGACTTAAGGGCAGGTTACCCACGCGTTACTCACCCATCCGCCGCTAGCTTGTA

TCTATGTCCATTCCGAAGAATTTCAATAGGCAAGCTCGCTCGACTTGCATGTATTAG

GCACGCCGCCAGCGT

*L. jensenii* ATCC #25258
27F (SEQ ID NO: 19)

GCAGTCGAGCGAGCTTGCCTATAGAAGTTCTTCGGAATGGAAATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACGGCTTACCAAGGCGATGATGCATAGCCGAGTTGAGAGACTGATCGGCCACAT

TGGGACTGAGACACGGCCCAAACTCCTACGGGAGGCAGCAGTAGGGAATCTTCCAC

AATGGACGAAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTACGTGCCAGCAGCCGCGGTAATACGTAGG

TGGCAAGCGTTGTCCGGATTTATTGGGCGTAAAGCGAGCGCAGGCGGATTGATAAG

TCTGATGTGAAAGCCTTCGGCTCAACCGAAGAACTGCATCAGAAACTGTCAATCTTG

AGTGCAGAAGAGGAGAGTGGAACTCCATGTGTAGCGGTGGAATGCGTAGATATATG

GAAGAACACCAGTGGCGAAGGCGGCTCTCTGGTCTGTAACTGACGCTGAGGCTCGA

AAGCATGGGTAGCGAACAGGATTAGATACCCTGGTAGTCCATGCCGTAAACGATGA

GTGCTAAGTGTTGGGAGGTTTCCGCCTCTCAGTGCTGCAGCTAACGCATTAAGCACT

CCGCC

-continued

1429R (SEQ ID NO: 20)
GCGGCTGGCTCCAAGGTTACCTCACCGACTTTGGGTGTTACAAACTCTCATGGTGTG

ACGGGCGGTGTGTACAAGGCCCGGGAACGTATTCACCGCGGCGTGCTGATCCGCGA

TTACTAGCGATTCCAGCTTCGTGTAGGCGAGTTGCAGCCTACAGTCCGAACTGAGAA

CAGCTTTAAGAGATCCGCTTGCCTTCACAGGTTCGCTTCTCGTTGTACTGCCCATTGT

AGCACGTGTGTAGCCCAGGTCATAAGGGGCATGATGACTTGACGTCATCCCCACCTT

CCTCCGGTTTGTCACCGGCAGTCTCAATAGAGTGCCCAACTTAATGCTGGCAACTAT

TAACAAGGGTTGCGCTCGTTGCGGGACTTAACCCAACATCTCACGACACGAGCTGA

CGACAGCCATGCACCACCTGTCTCTTTGTCCCCGAAGGGAAAACCTAATCTCTTAGG

TGGTCAAAGGATGTCAAGACCTGGTAAGGTTCTTCGCGTTGCTTCGAATTAAACCAC

ATGCTCCACCGCTTGTGCGGGCCCCCGTCAATTCCTTTGAGTTTCAACCTTGCGGTCG

TACTCCCCAGGCGGAGTGCTTAATGCGTTAGCTGCAGCACTGAGAGGCGGAAACCT

CCCAACACTTAGCACTCATCGTTTACGGCATGGACTACCAGGGTATCTAATCCTGTT

CGCTACCCATGCTTTCGAGCCTCAGCGTCAGTTACAGACCAGAGAGCCGCCTTCGCC

ACTGGTGTTCTTCCATATATCTACGCATTCCACCGCTACACATGGAGTTCCACTCTCC

TCTTCTGCACTCAAGATTGACAGTTTCTGATGCAGTTCTTCGGTTGAGCCGAAGGCTT

TCACATCAGACTTATCAATCCGCCTGCGCTCGCTTTACGCCC

*L. gasseri* BWH #117427
27F (SEQ ID NO: 21)
ATACcTGCAGTCGAGCGAGCTTGCCTAGATGAATTTGGTGCTTGCACCAgATGAAAC TaGATACAAGCGAGCGGCGGACGGGTGAGTAACACGTGGGTAACCTGCCCAAGAGA

CTGGGATAACACCTGGAAACAGATGCTAATACCGGATAACAACACTAGACGCATGT

CTAGAGTTTAAAAGATGGTTCTGCTATCACTCTTGGATGGACCTGCGGTGCATTAGC

TAGTTGGTAAGGCAACGGCTTACCAAGGCAATGATGCATAGCCGAGTTGAGAGACT

GATCGGCCACATTGGGACTGAGACACGGCCCAAACTCCTACGGGAGGCAGCAGTAG

GGAATCTTCCACAATGGACGCAAGTCTGATGGAGCAACGCCGCGTGAGTGAAGAAG

GGTTTCGGCTCGTAAAGCTCTGTTGGTAGTGAAGAAAGATAGAGGTAGTAACTGGC

CTTTATTTGACGGTAATTACTTAGAAAGTCACGGCTAACTACgTGC

529R (SEQ ID NO: 22)
TAGTATTACCGTCAATAAAGGCCAGTTACTACCTCTATCTTTCTTCACTACCAACAGA

GCTTTACGAGCCGAAACCCTTCTTCACTCACGCGGCGTTGCTCCATCAGACTTGCGT

CCATTGTGGAAGATTCCCTACTGCTGCCTCCCGTAGGAGTTTGGGCCGTGTCTCAGT

CCCAATGTGGCCGATCAGTCTCTCAACTCGGCTATGCATCATTGCCTTGGTAAGCCG

TTGCCTTACCAACTAGCTAATGCACCGCAGGTCCATCCAAGAGTGATAGCAGAACC

ATCTTTTAAACTCTAGACATGCGTCTAGTGTTGTTATCCGGTATTAGCATCTGTTTCC

AGGTGTTATCCCAGTCTCTTGGGCAGGTTACCCACGTGTTACTCACCCGTCCGCCGC

TCGCTTGTATCTAGTTTCATcTGGTGCAAGCACCAAATTCATCTAGGCAAGCTCGCTC

GACTTGCATGTATTAGGCACGCCGCCAGCGTTCGTCCTGA

-continued

L. gasseri BWH #217213
27F
(SEQ ID NO: 23)
ATAccTGCAGTCGAGCGAGCTTGCCTAGATGAATTTGGTGCTTGCACCAAATGAAAC

TAGATACAAGCGAGCGGCGGACGGGTGAGTAACACGTGGGTAACCTGCCCAAGAGA

CTGGGATAACACCTGGAAACAGATGCTAATACCGGATAACAACACTAGACGCATGT

CTAGAGTTTAAAAGATGGTTCTGCTATCACTCTTGGATGGACCTGCGGTGCATTAGC

TAGTTGGTAAGGTAACGGCTTACCAAGGCAATGATGCATAGCCGAGTTGAGAGACT

GATCGGCCACATTGGGACTGAGACACGGCCCAAACTCCTACGGGAGGCAGCAGTAG

GGAATCTTCCACAATGGACGCAAGTCTGATGGAGCAACGCCGCGTGAGTGAAGAAG

GGTTTCGGCTCGTAAAGCTCTGTTGGTAGTGAAGAAAGATAGAGGTAGTAACTGGC

CTTTATTTGACGGTAATTACTTAGAAAGTCACGGCTAACTACGTGCCA 529R
(SEQ ID NO: 24)
CTAGTATTACCGTCAATAAAGGCCAGTTACTACCTCTATCTTTCTTCACTACCAACAG

AGCTTTACGAGCCGAAACCCTTCTTCACTCACGCGGCGTTGCTCCATCAGACTTGCG

TCCATTGTGGAAGATTCCCTACTGCTGCCTCCCGTAGGAGTTTGGGCCGTGTCTCAGT

CCCAATGTGGCCGATCAGTCTCTCAACTCGGCTATGCATCATTGCCTTGGTAAGCCG

TTACCTTACCAACTAGCTAATGCACCGCAGGTCCATCCAAGAGTGATAGCAGAACC

ATCTTTTAAACTCTAGACATGCGTCTAGTGTTGTTATCCGGTATTAGCATCTGTTTCC

AGGTGTTATCCCAGTCTCTTGGGCAGGTTACCCACGTGTTACTCACCCGTCCGCCGC

TCGCTTGTATCTAGTTTCATTTGGTGCAAGCACCAAATTCATCTAGGCAAGCTCGCTC

GACTTGCATGTATTAGGCACGCCGCCAGCGTTCGTCCTGA

L. crispatus ATCC #3820
27F
(SEQ ID NO: 25)
GCGAGCGGAcTAACAGATTTACTTCGGTAATGACGTTAGGAAAGCGAGCGGCGGAT

GGGTGAGTAACACGTGGGGAACCTGCCCCATAGTCTGGGATACCACTTGGAAACAG

GTGCTAATACCGGATAAGAAAGCAGATCGCATGATCAGCTTTTAAAAGGCGGCGTA

AGCTGTCGCTATGGGATGGCCCCGCGGTGCATTAGCTAGTTGGTAAGGTAAAGGCTT

ACCAAGGCGATGATGCATAGCCGAGTTGAGAGACTGATCGGCCACATTGGGACTGA

GACACGGCCCAAACTCCTACGGGAGGCAGCAGTAGGGAATCTTCCACAATGGACGC

AAGTCTGATGGAGCAACGCCGCGTGAGTGAAGAAGGTTTTCGGATCGTAAAGCTCT

GTTGTTGGTGAAGAAGGATAGAGGTAGTAACTGGCCTTTATTTGACGGTAATCAACC

AGAAAGTCACGGCTAACTACGTGCCAGCAGCCGCGGTAATACGTAGGTGGCAAGCG

TTGTCCGGATTTATTGGGCGTAAAGCGAGCGCAGGCGGAAGAATAAGTCTGATGTG

AAAGCCCTCGGCTTAACCGAGGAACTGCATCGGAAACTGTTTTTCTTGAGTGCAGAA

GAcGAGAGTGGAACTCCATGTGTAGCGGTGGAATGCGTAGATATATGGAAGAACAC

CAGTGGCGAAgGCGGCTCTCTGGTCTGCAACTGACGCTGAGGCTCGAAAGCATGGGT

AGCGAACAGGATTAGATACCCTGGTAGTCCATGCCGTAAACGATGAgTGCTAAGTGT

TGGGAGG 1429R
(SEQ ID NO: 26)
GGTTAGGCCACCGGCTTTGGGCATTGCAGACTCCCATGGTGTGACGGGCGGTGTGTA

CAAGGCCCGGGAACGTATTCACCGCGGCGTGCTGATCCGCGATTACTAGCGATTCCA

```
                                         -continued
GCTTCGTGCAGTCGAGTTGCAGACTGCAGTCCGAACTGAGAACAGCTTTCAGAGATT

CGCTTGCCTTCGCAGGCTCGCTTCTCGTTGTACTGCCCATTGTAGCACGTGTGTAGCC

CAGGTCATAAGGGGCATGATGACTTGACGTCATCCCCACCTTCCTCCGGTTTGTCAC

CGGCAGTCTCATTAGAGTGCCCAACTTAATGCTGGCAACTAATAACAAGGGTTGCGC

TCGTTGCGGGACTTAACCCAACATCTCACGACACGAGCTGACGACAGCCATGCACC

ACCTGTCTTAGCGTCCCCGAAGGGAACTTTGTATCTCTACAAATGGCACTAGATGTC

AAGACCTGGTAAGGTTCTTCGCGTTGCTTCGAATTAAACCACATGCTCCACCGCTTG

TGCGGGCCCCCGTCAATTCCTTTGAGTTTCAACCTTGCGGTCGTACTCCCCAGGCGG

AGTGCTTAATGCGTTAGCTGCAGCACTGAGAGGCGGAAACCTCCCAACACTTAGCA

CTCATCGTTTACGGCATGGACTACCAGGGTATCTAATCCTGTTCGCTACCCATGCTTT

CGAGCCTCAGCGTCAGTTGCAGACCAGAGAGCCGCCTTCGCCACTGGTGTTCTTCCA

TATATCTACGCATTCCACGCTACACATGGAGTTCCACTCTCCTCTTCTGCACTCAAGA

AAAACAGTTTCCGATGCAGTTCCTCGGTTAAGCCGAGGGCTTTCACATCAAACTTAT

TCTTCCGCCTGCGCTCGCTTTACGCCCAATAAATCCGGA

L. crispatus Sh. Hillier
27F
                                                        (SEQ ID NO: 27)
TGCAGTCGAGCGAGCGGACTAACAGATTTACTTCGGTAATGACGTTAGGAAAGCGA

GCGGCGGATGGGTGAGTAACACGTGGGGAACCTGCCCCATAGTCTGGGATACCACT

TGGAAACAGGTGCTAATACCGGATAAGAAAGCAGATCGCATGATCAGCTTTTAAAA

GGCGGCGTAAGCTGTCGCTATGGGATGGCCCCGCGGTGCATTAGCTAGTTGGTAAG

GTAAAGGCTTACCAAGGCGATGATGCATAGCCGAGTTGAGAGACTGATCGGCCACA

TTGGGACTGAGACACGGCCAAACTCCTACGGGAGGCAGCAGTAGGGAATCTTCCAC

AATGGACGCAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTACGTGCCAGCAGCCGCGGTAATACGTAGG

TGGCAAGCGTTGTCCGGATTTATTGGGCGTAAAGCGAGCGCAGGCGGAAGAATAAG

TCTGATGTGAAAGCCCTCGGCTTAACCGAGGAACTGCATCGGAAACTGTTTTTCTTG

AGTGCAGAAGAGGAGAGTGGAACTCCATGTGCTCTCTGGTCTGCAACTGACGCTGA

GGCTCGAAAGCATGGGTAGCGAACAGGATAGATACCCTGGTAGTCCATGCCGTAAA

CGATGAGTGCTAAGTGTTGGGAGGTTTCCGCCTCTCAGTGCTGCAGCTAACGCATTA

AGCACTCCGCCGGGGAGTACGACCGC 1429R
                                                        (SEQ ID NO: 28)
AAGGTTAGGCCACCGGCTTTGGGCATTGCAGACTCCCATGGTGTGACGGGCGGTGTG

TACAAGGCCCGGGAACGTATTCACCGCGGCGTGCTGATCCGCGATTACTAGCGATTC

CAGCTTCGTGCAGTCGAGTTGCAGACTGCAGTCCGAACTGAGAACAGCTTTCAGAG

ATTCGCTTGCCTTCGCAGGCTCGCTTCTCGTTGTACTGCCCATTGTAGCACGTGTGTA

GCCCAGGTCATAAGGGGCATGATGACTTGACGTCATCCCCACCTTCCTCCGGTTTGT

CACCGGCAGTCTCATTAGAGTGCCCAACTTAATGCTGGCAACTAATAACAAGGGTTG

CGCTCGTTGCGCTGTCTTAGCGTCCCCGAAGGGAACTTTGTATCTCTACAAATGGCA

CTAGATGTCAAGACCTGGTAAGGTTCTTCGCGTTGCTTCGAATTAAACCACATGCTC

CACCGCTTGTGCGGGCCCCCGTCAATTCCTTTGAGTTTCAACCTTGCGGTCGTACTCC
```

-continued
CCAGGCGGAGTGCTTAATGCGTTAGCTGCAGCACTGAGAGGCGGAAACCTCCCAAC

ACTTAGCACTCATCGTTTACGGCATGGACTACCAGGGTATCTAATCCTGTTCGCTAC

CCATGCTTTCGAGCCTCAGCGTCAGTTGCAGACCAGAGAGCCGCCTTCGCCACTGGT

GTTCTTCCATATATCTACGCATTCCACCGCTACACATGGAGTTCCACTCTCCTCTTCT

GCACTCAAGAAAAACAGTTTCCGATGCAGTTCCTCGGTTAAGCCGAGGGCTTTCACA

TCAGACTTATTCTTCCGCCTGCGCTCGCTTTACGCCCAATAAATCCGGACAACG

L. crispatus BWH #101211
27F
(SEQ ID NO: 29)
TATGGgATGGCCCCGCGGTGCaTTAACTAgTTGGTAAGGTAAAGGCTTACCAAGGCG ATGATGCATAgCCgAGTTGAGAGACTGATCGGCCACATTGGGACTGAGACACGGCCC

AAACTCCTACGGGAGGCAGCAGTAGGGAATCTTCCACAATGGACGCAAGTCTGATG

GAGCAACGCCGCGTGAGTGAAGAAGGTTTTCGGATCGTAAAGCTCTGTTGTTGGTGA

AGAAGGATAGAGGTAGTAACTGGCCTTTATTTGACGGTAATCAACCAGAAAGTCAC

GGCTAACTACGTGCCAGCAGCCGCGGTAATACGTAGGTGGCAAGCGTTGTCCGGAT

TTATTGGGCGTAAAGCGAGCGCAGGCGGAAGAATAAGTCTGATGTGAAAGCCCTCG

GCTTAACCGAGGAACTGCATCGGAAACTGTTTTTCTTGAGTGCAGAAGAgGAGAGTG

GAACTCCATGTGTAGCGGTGGAATGCGTAGATATATGGAAgAACACCAGTGGCGAag gCGGCTCTCTGGTCTGCAACTGACGCTGAGGCTCGAAAGCATGGGTAGCGAa 1429R
(SEQ ID NO: 30)
GACTTGatGtCATCCCCaCCTTCCtCCCGGtTtGtCACCggcaGTCTCATTAgAGTGCCCAACT TAATGCTGGcAACtAAtAACAAGGGTTGCGCTCGTTGCGGGACTTAACCCAACATCTC ACGACACgAGCTGACGACAGCCATGCACCACCTGTCTTAgCGTCCCCGAAGGgAAcTT TGTATCTCTACaAATGGCACTAGATGTCAAGACCTGGTAAGGTTCTTCGCGTTGCTTC

GAATTAAACCACATGCTCCACCGCTTGTGCGGGCCCCCGTCAATTCCTTTGAGTTTC

AACCTTGCGGTCGTACTCCCCAgGCGGAgTGCTTAaTGCGTTAGCTGCAGCACTGAGa

GGCgGAAACCTCCcaACACTTAGCACTCATCG

APPENDIX B
Vaginal Lactobacillus strain candidates contemplated to be
beneficial in a medicinal bacterial mix (good clinical phenotype,
term pregnancy):
Primer sequences
1) 27F:
(SEQ ID NO: 49)
AGA GTT TGA TCM TGG CTC AG 2) 1492R:
(SEQ ID NO: 50)
CGG TTA CCT TGT TAC GAC TT 3) 529R:
(SEQ ID NO: 51)
CGC GGC TGC TGG CAC L. crispatus BWH #24629
27F
(SEQ ID NO: 31)
ATCgCATGATCAGgTTTTAaaaaGaaGcgTAaGCTGTCgCTATGGGATGGCCCCGCGGTGC

ATTAACTAGTTGGTAAGGTAAAGGCTTACCAAGGCGATGATGCATAGCCGAGTTGA

GAGACTGATCGGCCACATTGGGACTGAGACACGGCCCAAACTCCTACGGGAGGCAG

CAGTAGGGAATCTTCCACAATGGACGCAAGTCTGATGGAGCAACGCCGCGTGAGT

-continued

AAGAAGGTTTTCGGATCGTAAAGCTCTGTTGTTGGTGAAGAAGGATAGAGGTAGTA

ACTGGCCTTTATTTGACGGTAATCAACCAGAAAGTCACGGCTAACTACGTGCCAGCA

GCCGCGGTAATACGTAGGTGGCAAGCGTTGTCCGGATTTATTGGGCGTAAAGCGAG

CGCAGGCGGAAGAaTAAGTCTGATGTGAAAGCCCTCGGCTTAACCGAGGAACTGCA

TCGGAAACTGTTTTTCTTGAGTGCAGAAGAaGAgAGTGGAACTCCATGTGTAGCGGT

GGAATGCGTAgATATATGGAAGAAcACCAGTGgcGAAaGGcGGCTCTCTGGTCTGCAA

CTGAcGCTGAGGCTCGAAAGCATGGGTAGCGAACAGGATTAaATACCcTGG 1429R
(SEQ ID NO: 32)
GAtGACTTGtcGTCaTCCCCACCTtCCtCCGGtTtGacAcCgGcaGTCTCATTAgAGTGCCCAA

CTTAATGCTGGcAACTAATAACAAGGGTTGCGCTCGTTGCGGGACTTAACCCAACAT

CTCACGACACGAGCTGACGACAGCCATGCACCACCTGTCTTAGCGTCCCCGAAGGG

AACTTTGTATCTCTACAAATGGCACTAGATGTCAAGACCTGGTAAGGTTCTTCGCGT

TGCTTCGAATTAAACCACATGCTCCACCGCTTGTGCGGGCCCCCGTCAATTCCTTTG

AGTTTCAACCTTGCGGTCGTACTCCCCAGGCGGAgTGCTTAATGCGTTAGCTGCAGC

ACTGAGAGGCGGAAACCTCCCAACACTTAGCACTCATCGTTTACGGCATGGACTACC

AgGGTATCTAATCCTGTTCGCTACCCATGCTTTCGAGCCTCAGCGTCAGTTGCAGAcC

AGAGAGCCGCCtTCGCCACTGGTGTTCTtCCATATATCTACGCATTCCACCGCTACAC

ATGGAGTTccAcTCTCCTCTTCTGCACTCAAaAAAAACAGTTTcCGATGCAGTTCCTCG

GTTAAccCaAGGGCTTTcACATCAaAcT

*L. jensenii* BWH #2054211
27F
(SEQ ID NO: 33)
TGCAGTCGAGCGAGCTTGCCTATTGAAATTCTTCGGAATGGACATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACGGCTTACCAAGGCGATGATGCATAGCCGAGTTGAGAGACTGATCGGCCACAT

TGGGACTGAGACACGGCCCAAACTCCTACGGGAGGCAGCAGTAGGGAATCTTCCAC

AATGGACGCAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTACGTGCCA 529R
(SEQ ID NO: 34)
CGTCaATAAAGGCCAGTTACTACCTCTATCCTTCTTCACCAACAACAGAGCTTTACGA

TCCGAAAACCTTCTTCACTCACGCGGCGTTGCTCCATCAGACTTGCGTCCATTGTGG

AAGATTCCCTACTGCTGCCTCCCGTAGGAGTTTGGGCCGTGTCTCAGTCCCAATGTG

GCCGATCAGTCTCTCAACTCGGCTATGCATCATCGCCTTGGTAAGCCGTTACCTTAC

CAACTAGCTAATGCATCGCAGGTCCATCCTTTAGCGACAGCTTACGCCGCCTTTTAA

ACTTCTTTCATGCGAAAGTAGCTTTTATCCGGTATTAGCATCTGTTTCCAAATGGTAT

CCCAGACTTAAGGGCAGGTTACCCACGCGTTACTCACCCATCCGCCGCTAGCTTGTA

TCTATGTCCATTCCGAAGAATTTCAATAGGCAAGCTCGCTCGACTTGCATGTATTAG

GCACGCCGCCAGCGTTCGTCCTGA

*L. jensenii* BWH #285216
27F (SEQ ID NO: 35)
TGCAGTCGAGCGAGCTTGCCTATAGAAGTTCTTCGGAATGGACATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACGGCTTACCAAGGCGATGATGCATAGCCGAGTTGAGAGACTGATCGGCCACAT

TGGGACTGAGACACGGCCCAAACTCCTACGGGAGGCAGCAGTAGGGAATCTTCCAC

AATGGACGAAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTAC

529R (SEQ ID NO: 36)
CGTCAATAAAGGCCAGTTACTACCTCTATCCTTCTTCACCAACAACAGAGCTTTACG

ATCCGAAAACCTTCTTCACTCACGCGGCGTTGCTCCATCAGACTTTCGTCCATTGTGG

AAGATTCCCTACTGCTGCCTCCCGTAGGAGTTTGGGCCGTGTCTCAGTCCCAATGTG

GCCGATCAGTCTCTCAACTCGGCTATGCATCATCGCCTTGGTAAGCCGTTACCTTAC

CAACTAGCTAATGCATCGCAGGTCCATCCTTTAGCGACAGCTTACGCCGCCTTTTAA

ACTTCTTTCATGCGAAAGTAGCTTTTATCCGGTATTAGCATCTGTTTCCAAATGGTAT

CCCAGACTTAAGGGCAGGTTACCCACGCGTTACTCACCCATCCGCCGCTAGCTTGTA

TCTATGTCCATTCCGAAGAACTTCTATAGGCAAGCTCGCTCGACTTGCATGTATTAG

GCACGCCGCCAGCGTTC

*L. jensenii* BWH #174825
27F (SEQ ID NO: 37)
GCTTGCCTATAGAAGTTCTTCGGAATGGACATAGATACAAGCTAGCGGCGGATGGG TGaGTAACGCGTGGGTAACCTGCCCTTAAGTCTGGGATACCATTTGGAAACAGATGC

TAATACCGGATAAAAGCTACTTTCGCATGAAAGAAGTTTAAAAGGCGGCGTAAGCT

GTCGCTAAAGGATGGACCTGCGATGCATTAGCTAGTTGGTAAGGTAACGGCTTACCA

AGGCGATGATGCATAGCtgagtTGAGAGACTGATCGGCCACATTGGGACTGAGACACG

GCCCAAACTCCTACGGGAGGCAGCAGTAGGGAATCTTCCACAATGGACGAAAGTCT

GATGGAGCAACGCCGCGTGAGTGAAGAAGGTTTTCGGaTCGTAAAGCTCTGTTGTTG

GTGAAGAAGGATAGAGGTAGTAACTGGCCTTTATTTGACGGTAATCAACCAGAAAG

TCACGGCTAACTACGTGCC

529R (SEQ ID NO: 38)
ATAAAGGCCAGTTACTACCTCTATCCTTCTTCACCAACAACAGAGCTTTACGATCCG

AAAACCTTCTTCACTCACGCGGCGTTGCTCCATCAGACTTTCGTCCATTGTGGAAGA

TTCCCTACTGCTGCCTCCCGTAGGAGTTTGGGCCGTGTCTCAGTCCCAATGTGGCCG

ATCAGTCTCTCAACTCaGCTATGCATCATCGCCTTGGTAAGCCGTTACCTTACCAACT

AGCTAATGCATCGCAGGTCCATCCTTTAGCGACAGCTTACGCCGCCTTTTAAACTTCT

TTCATGCGAAAGTAGCTTTTATCCGGTATTAGCATCTGTTTCCAAATGGTATCCCAGA

-continued

CTTAAGGGCAGGTTACCCACGCGTTACTCACCCATCCGCCGCTAGCTTGTATCTATG

TCCATTCCGAAGAACTTCTATAGGCAAGCTCGCTCGACTTGCATGTATTAGGCACGC

CGCCAGCGTTCGTCCTGAGC

*L. jensenii* BWH #171928
27F
(SEQ ID NO: 39)
TGCAGTCGAGCGAGCTTGCCTATTGAAATTCTTCGGAATGGACATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACGGCTTACCAAGGCGATGATGCATAGCCGAGTTGAGAGACTGATCGGCCACAT

TGGGACTGAGACACGGCCCAAACTCCTACGGGAGGCAGCAGTAGGGAATCTTCCAC

AATGGACGCAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTACGTGCCA 529R
(SEQ ID NO: 40)
CGTCAATAAAGGCCAGTTACTACCTCTATCCTTCTTCACCAACAACAGAGCTTTACG

ATCCGAAAACCTTCTTCACTCACGCGGCGTTGCTCCATCAGACTTGCGTCCATTGTG

GAAGATTCCCTACTGCTGCCTCCCGTAGGAGTTTGGGCCGTGTCTCAGTCCCAATGT

GGCCGATCAGTCTCTCAACTCGGCTATGCATCATCGCCTTGGTAAGCCGTTACCTTA

CCAACTAGCTAATGCATCGCAGGTCCATCCTTTAGCGACAGCTTACGCCGCCTTTTA

AACTTCTTTCATGCGAAAGTAGCTTTTATCCGGTATTAGCATCTGTTTCCAAATGGTA

TCCCAGACTTAAGGGCAGGTTACCCACGCGTTACTCACCCATCCGCCGCTAGCTTGT

ATCTATGTCCATTCCGAAGAATTTCAATAGGCAAGCTCGCTCGACTTGCATGTATTA

GGCACGCCGCCAGCGTTCGTCCTGAGCC

*L. jensenii* BWH #22731
27F
(SEQ ID NO: 41)
TGCAGTCGAGCGAGCTTGCCTATTGAAATTCTTCGGAATGGACATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACGGCTTACCAAGGCGATGATGCATAGCCGAGTTGAGAGACTGATCGGCCACAT

TGGGACTGAGACACGGCCCAAACTCCTACGGGAGGCAGCAGTAGGGAATCTTCCAC

AATGGACGCAAGTCTGATGGAGCAACGCCGCGTGAGTGAAGAAGGTTTTCGGATCG

TAAAGCTCTGTTGTTGGTGAAGAAGGATAGAGGTAGTAACTGGCCTTTATTTGACGG

TAATCAACCAGAAAGTCACGGCTAACTAC 529R
(SEQ ID NO: 42)
CGTCaATAAAGGCCAGTTACTACCTCTATCCTTCTTCACCAACAACAGAGCTTTACGA

TCCGAAAACCTTCTTCACTCACGCGGCGTTGCTCCATCAGACTTGCGTCCATTGTGG

AAGATTCCCTACTGCTGCCTCCCGTAGGAGTTTGGGCCGTGTCTCAGTCCCAATGTG

GCCGATCAGTCTCTCAACTCGGCTATGCATCATCGCCTTGGTAAGCCGTTACCTTAC

CAACTAGCTAATGCATCGCAGGTCCATCCTTTAGCGACAGCTTACGCCGCCTTTTAA

-continued

ACTTCTTTCATGCGAAAGTAGCTTTTATCCGGTATTAGCATCTGTTTCCAAATGGTAT

CCCAGACTTAAGGGCAGGTTACCCACGCGTTACTCACCCATCCGCCGCTAGCTTGTA

TCTATGTCCATTCCGAAGAATTTCAATAGGCAAGCTCGCTCGACTTGCATGTATTAG

GCACGCCGCCAGCGTTCGTCCTGA

*L. jensenii* BWH #220613
27F
(SEQ ID NO: 43)
TGCAGTCGAGCGAGCTTGCCTATAGAAATTCTTCGGAATGGACATAGATACAAGCTA

GCGGCGGATGGGTGAGTAACGCGTGGGTAACCTGCCCTTAAGTCTGGGATACCATTT

GGAAACAGATGCTAATACCGGATAAAAGCTACTTTCGCATGAAAGAAGTTTAAAAG

GCGGCGTAAGCTGTCGCTAAAGGATGGACCTGCGATGCATTAGCTAGTTGGTAAGG

TAACgGCTTACCAAGGCGATGATGCATAGCCGAGTTGAGAGACTGATCGGCCACATT

GGGACTGAGACACGGCCCAAACTCCTACGGGAGGCAGCAGTAGGGAATCTTCCACA

ATGGACGAAAGTCTGATGGAGCAACGCCGCGTGAGTGAAGAAGGTTTTCGGATCGT

AAAGCTCTGTTGTTGGTGAAGAAGGATAGAGGTAGTAACTGGCCTTTATTTGACGGT

AATCAACCAGAAAGTCACGGCTAACTACGTGCCAGCAG 529R
(SEQ ID NO: 44)
CGTCaATAAAGGCCAGTTACTACCTCTATCCTTCTTCACCAACAACAGAGCTTTACGA

TCCGAAAACCTTCTTCACTCACGCGGCGTTGCTCCATCAGACTTTCGTCCATTGTGGA

AGATTCCCTACTGCTGCCTCCCGTAGGAGTTTGGGCCGTGTCTCAGTCCCAATGTGG

CCGATCAGTCTCTCAACTCGGCTATGCATCATCGCCTTGGTAAGCcGTTACCTTACCA

ACTAGCTAATGCATCGCAGGTCCATCCTTTAGCGACAGCTTACGCCGCCTTTTAAAC

TTCTTTCATGCGAAAGTAGCTTTTATCCGGTATTAGCATCTGTTTCCAAATGGTATCC

CAGACTTAAGGGCAGGTTACCCACGCGTTACTCACCCATCCGCCGCTAGCTTGTATC

TATGTCCATTCCGAAGAATTTCTATAGGCAAGCTCGCTCGACTTGCATGTATTAGGC

ACGCCGCCAGCGT

*L. gasseri* BWH #192712
27F
(SEQ ID NO: 45)
GAGCTTGCCTAGATGAATTTGGTGCTTGCACCAAATGAAACTAGATACAAGCGAGC GGCGGACGGGTGAGTAACACGTGGGTAACCTGCCCAagAgACTGGGATAACACCTGG

AAACAGATGCTAATACCGGATAACAACACTAGACGCATGTCTAGAGTTTAAAAGAT

GGTTCTGCTATCACTCTTGGATGGACCTGCGGTGCATTAGCTAGTTGGTAAGGTAAC

GGCTTACCAAGGCAATGATGCATAGCCgAgttGAGAGACTGATCGGCCACATTGGGAC

TGAGACACGGCCCAAACTCCTACGGGAGGCAGCAGTAGGGAATCTTCCACAATGGA

CGCAAGTCTGATGGAGCAACGCCGCGTGAGTGAAGAAGGGTTTCGGCTCGTAAAGC

TCTGTTGGTAGTGAAGAAAGATAGAGGTAGTAACTGGCCTTTATTTGACGGTAATTA

CTTAGAAgGTCACGGCTAACTACGTGCCA 529R
(SEQ ID NO: 46)
ACCGTCNATAAaGGCCaGTTACTACCTCTATCTTTCTTCaCTACCAACAGAGCTTTACG

AGCCGAAACCCTTCTTCACTCACGCGGCGTTGCTCCATCAGACTTGCGTCCATTGTG

GAAGATTCCCTACTGCTGCCTCCCGTAGGAGTTTGGGCCGTGTCTCAGTCCCAATGT

GGCCGATCAGTCTCTCAACTCGGCTATGCATCATTGCCTTGGTAAGCCGTTACCTTAC

CAACTAGCTAATGCACCGCAGGTCCATCCAAGAGTGATAGCAGAACCATCTTTTAAA

-continued

CTCTAGACATGCGTCTAGTGTTGTTATCCGGTATTAGCATCTGTTTCCAGGTGTTATC

CCAGTCTCTTGGGCAGGTTACCCACGTGTTACTCACCCGTCCGCCGCTCGCTTGTATC

TAGTTTCATTTGGTGCAAGCACCAAATTCATCTAGGCAAGCTCGCTCGACTTGCATG

TATTAGGCaCgCCGCC

L. gasseri BWH #203326
27F
(SEQ ID NO: 47)
TGCAGTCGAGCGAGCTTGCCTAGATGAATTTGGTGCTTGCACCAAATGAAACTAGAT

ACAAGCGAGCGGCGGACGGGTGAGTAACACGTGGGTAACCTGCCCAAGAGACTGG

GATAACACCTGGAAACAGATGCTAATACCGGATAACAACACTAGACGCATGTCTAG

AGTTTAAAAGATGGTTCTGCTATCACTCTTGGATGGACCTGCGGTGCATTAGCTAGT

TGGTAAGGCAACGGCTTACCAAGGCAATGATGCATAGCCGAGTTGAGAGACTGATC

GGCCACATTGGGACTGAGACACGGCCCAAACTCCTACGGGAGGCAGCAGTAGGGAA

TCTTCCACAATGGACGCAAGTCTGATGGAGCAACGCCGCGTGAGTGAAGAAGGGTT

TCGGCTCGTAAAGCTCTGTTGGTAGTGAAGAAAGATAGAGGTAGTAACTGGCCTTTA

TTTGACGGTAATTACTTAGAAAGTCACGGCTaACTACGTGCCAGCAGCC 529R
(SEQ ID NO: 48)
TATTACCGTCaaTAaGGCCAGTTACTACCTCTATCTTTCTTCaCTACCAACAGAGCTTT

ACGAGCCGAAACCCTTCTTCACTCACGCGGCGTTGCTCCATCAGACTTGCGTCCATT

GTGGAAGATTCCCTACTGCTGCCTCCCGTAGGAGTTTGGGCCGTGTCTCAGTCCCAA

TGTGGCCGATCAgTCTCTCAACTCGGCTATGCATCATTGCCTTGGTAAGCCGTTGCCT

TACCAACTAGCTAATGCACCGCAGGTCCATCCAAGAGTGATAGCAgAACCATCTTTT

AAACTCTAGACATGCGTCTAGTGTTGTTATCCGGTATTAGCATCTGTTTCCAGGTGTT

ATCCCAGTCTCTTGGGCAGGTTACCCACGTGTTACTCACCCGTCCGCCGCTCGCTTGT

ATCTAGTTTCATTTGGTGCAAGCACCAaATTCATCTAggCAAGCTCGCTCGACTTGCA

TGtATTAGGcacgcCGCC

APPENDIX C

| Phenotypic Characteristics of strains L. gasseri 29313, L. Crispatus 223310, L. jensenii 2054210 | | | |
|---|---|---|---|
| | L. gasseri 293-13/L. acidphilus 239-13 ATCC SD-7101 | L. jensenii 2054210 ATCC SD-7102 | L. crispatus 223310 ATCC S-6994; SD-7100 |
| Rapid ANA II System (R8311002) - Remel Inc., Lenexa KS Hydrolysis of the following | | | |
| Urea | Negative | Negative | Negative |
| Beta-D-disaccharide | Negative | Negative | Negative |
| Alpha-L-arabinoside | Negative | Negative | Negative |
| Beta-D-galactoside | Negative | Negative | Negative |
| Alpha-D-glucoside | Positive | Positive | Positive |
| Beta-D-glucoside | Positive | Positive | Positive |
| Alpha-D-galactoside | Negative | Negative | Negative |
| Alpha-L-fucoside | Negative | Negative | Negative |
| Beta-D-glucosaminide | Positive | Negative | Negative |
| Phosphate | Negative | Negative | Negative |
| Leucyl-glycine | Positive | Positive | Positive |
| Glycine | Positive | Positive | Positive |
| Proline | Positive | Positive | Negative |
| Phenylalanine | Positive | Positive | Positive |
| Arginine | Positive | Positive | Positive |
| Serine | Positive | Positive | Positive |
| Pyrrolidonyl | Positive | Negative | Negative |
| Formation of Indole | Negative | Negative | Negative |

APPENDIX C-continued

Phenotypic Characteristics of strains *L. gasseri* 29313, *L. Crispatus* 223310, *L. jensenii* 2054210

| | *L. gasseri* 293-13/*L. acidphilus* 239-13<br>ATCC SD-7101 | *L. jensenii* 2054210<br>ATCC SD-7102 | *L. crispatus* 223310<br>ATCC S-6994; SD-7100 |
|---|---|---|---|
| | PRAS - Anaerobe Systems, Morgan Hill CA<br>Fermentation of the following | | |
| Arabinose | Negative | Negative | Negative |
| Cellobiose | Positive | Positive | Positive |
| Esculin | Positive | Weak | Positive |
| Esculin hydrolysis | Positive | Positive | Positive |
| Glucose | Positive | Positive | Positive |
| Lactose | Positive | Negative | Positive |
| Maltose | Positive | Positive | Positive |
| Mannitol | Negative | Negative | Negative |
| Mannose | Positive | Positive | Positive |
| Raffinose | Negative | Positive | Positive |
| Rhamnose | Negative | Negative | Negative |
| Salicin | Positive | Positive | Positive |
| Sucrose | Positive | Positive | Positive |
| Trehalose | Positive | Positive | Positive |
| Xylose | Negative | Negative | Negative |
| | Maldi - TOF Mass Spectrometry (Biomerieux Inc., Durham, NC) | | |
| | *L. gasseri* 50%<br>*L. acidophilus* 50% | *L. jensenii* 99.9% | *L. crispatus* 99.9% |

The invention claimed is:

1. A composition for promoting a healthy human vaginal microbiota balance, the composition comprising a mixture of viable bacteria comprising *Lactobacillus crispatus, Lactobacillus jensenii*, and *Lactobacillus* gasseri;
   wherein one or two bacteria of the composition are selected from the group consisting of: *Lactobacillus crispatus* strain 223310 identified by ATCC deposit PTA-127090; *Lactobacillus jensenii* strain 2054210 identified by ATCC deposit PTA-127092; and *Lactobacillus* gasseri strain is 29313 identified by ATCC deposit PTA-127091, and
   wherein the composition is formulated for vaginal, oral, or rectal delivery, wherein the mixture of viable bacteria is in a glassy matrix, preserved by preservation by vaporization (PBV), or lyophilized.

2. The composition of claim 1, further comprising an agent that promotes bacterial growth, a low pH buffering agent, a prebiotic, an anti-microbial agent/preparation, 9-(2-deoxy-2-fluoro-β-Darabinofuranosyl) adenine (WF-50), at least one antibiotic, or at least one excipient.

3. The composition of claim 2, wherein the low pH buffering agent is boric acid, lactic acid, or ascorbic acid.

4. The composition of claim 2, wherein the prebiotic is sucrose.

5. The composition of claim 2, wherein the anti-microbial preparation comprises recombinant human soluble serine protease inhibitor (SLPI).

6. The composition of claim 2, wherein the at least one antibiotic is metronidazole or clindamycin.

7. The composition of claim 2, wherein the at least one excipient comprises a nonreducing monosaccharide, sugar alcohol, oligosaccharide, amino acid, polyvinylpyrrolodone, polyethylene glycol, branched hydrophilic polysaccharide, inulin, albumin, gelatin, whey proteins, and/or a polaxomer.

8. The composition of claim 1, wherein the composition is stable at room temperature for at least one year when preserved by PBV.

9. A method comprising administering a composition of claim 1 to a subject at risk of developing vaginal dysbiosis or having vaginal dysbiosis.

10. The method of claim 9, wherein the vaginal or cervical infection is:
   a. bacterial vaginosis;
   b. caused by the vaginal pathogen *Trichomonas vaginalis;*
   c. caused by the vaginal pathogen *Gardnerella vaginalis;*
   d. caused by the vaginal pathogen *Prevotella bivia;* or
   e. caused by the vaginal pathogen *Atopobium vaginae.*

11. The method of claim 9, further comprising selecting a subject at risk for or having been identified as having a vaginal infection.

12. The method of claim 9, wherein administering the composition restores a healthy vaginal flora.

13. A method of maintaining, establishing, or restoring a human vaginal microbiota balance, the method comprising administering a composition of claim 1 to a human subject in need thereof.

14. The composition of claim 1, wherein the *Lactobacillus crispatus* is strain 223310 identified by ATCC deposit PTA-127090.

15. The composition of claim 14, further comprising at least one of *Lactobacillus jensenii* strain 2054210 identified by ATCC deposit PTA-127092 and *Lactobacillus* gasseri strain is 29313 identified by ATCC deposit PTA-127091.

16. The composition of claim 1, further comprising an antibiotic.

17. The composition of claim 16, wherein the antibiotic treats a sexually transmitted and reproductive tract infection selected from bacterial vaginosis, *Chlamydia, Candida*, and *Trichomonas vaginalis*.

18. The method of claim 13, wherein the subject is pregnant or is not pregnant.

\* \* \* \* \*